United States Patent
Ise et al.

(10) Patent No.: US 7,118,811 B2
(45) Date of Patent: *Oct. 10, 2006

(54) MATERIALS FOR LIGHT EMITTING DEVICES CONSISTING OF NOVEL COMPOUNDS AND LIGHT EMITTING DEVICES USING THE SAME

(75) Inventors: Toshihiro Ise, Ashigara (JP); Hisashi Okada, Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 152 days.

This patent is subject to a terminal disclaimer.

(21) Appl. No.: 10/625,539

(22) Filed: Jul. 24, 2003

(65) Prior Publication Data

US 2004/0146745 A1 Jul. 29, 2004

Related U.S. Application Data

(62) Division of application No. 09/697,157, filed on Oct. 27, 2000, now Pat. No. 6,620,529.

(30) Foreign Application Priority Data

| Oct. 27, 1999 | (JP) | ............................... P.11-305733 |
| Mar. 7, 2000 | (JP) | ............................ P.2000-62472 |
| Mar. 28, 2000 | (JP) | ............................ P.2000-89632 |

(51) Int. Cl.
| H01L 51/54 | (2006.01) |
| H05B 33/14 | (2006.01) |
| C09K 11/06 | (2006.01) |
| C07D 401/00 | (2006.01) |
| C07D 403/00 | (2006.01) |
| C07D 405/00 | (2006.01) |
| C07D 409/00 | (2006.01) |
| C07D 413/00 | (2006.01) |
| C07D 417/00 | (2006.01) |
| C07D 421/00 | (2006.01) |

(52) U.S. Cl. ...................... 428/690; 428/917; 313/504; 313/506; 548/301.7; 548/304.4; 548/304.7; 548/306.1; 548/307.4; 548/309.7

(58) Field of Classification Search ................ 428/690, 428/917; 313/504, 506; 548/301.7, 304.4, 548/304.7, 306.1, 307.4, 309.7
See application file for complete search history.

(56) References Cited

U.S. PATENT DOCUMENTS

| 4,197,401 | A | 4/1980 | Gunther et al. | ............. 542/434 |
| 5,281,489 | A | 1/1994 | Mori et al. | ................ 428/690 |
| 5,766,779 | A | 6/1998 | Shi et al. | .................... 428/690 |
| 5,968,933 | A * | 10/1999 | Denny et al. | ............ 514/228.2 |
| 6,379,823 | B1 * | 4/2002 | Nii et al. | .................... 428/690 |
| 6,440,586 | B1 * | 8/2002 | Yanagi et al. | ................ 428/690 |
| 6,458,474 | B1 * | 10/2002 | Okada et al. | ................ 428/690 |
| 6,537,687 | B1 * | 3/2003 | Nii | .............................. 428/690 |

FOREIGN PATENT DOCUMENTS

| JP | 59-75257 | A | 4/1984 |
| JP | 4-298596 | A | 10/1992 |
| JP | 10-092578 | A | 4/1998 |

OTHER PUBLICATIONS

1983:34527 HCAPLUS (for Krasovitskii et al., Khimiya Geterotsiklicheskikh Soedinenii, 1982).*
1984:6392 HCAPLUS (for Krasovitskii et al., Zhurnal Vsesoyuznogo Khimicheskogo Obshchestva im. D. I. Mendeleeva, 1983).*

(Continued)

Primary Examiner—Marie Yamnitzky
(74) Attorney, Agent, or Firm—Sughrue Mion, PLLC

(57) ABSTRACT

A compound represented by formula (IA) or (IIA):

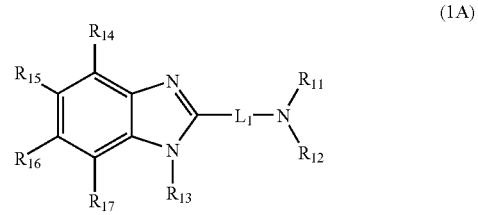

(IA)

wherein $R_{11}$, $R_{12}$ and $R_{13}$ each represents a hydrogen atom, an aliphatic hydrocarbon group, an aryl group or a heterocyclic group; $L_1$ represents a connecting group; $R_{11}$ and $R_{12}$, $R_{11}$ and $L_1$ and $R_{12}$ and $L_1$ may each combine with each other to form a ring when possible; $R_{14}$, $R_{15}$, $R_{16}$ and $R_{17}$ each represents a hydrogen atom or a substituent; and $R_{13}$ to $R_{17}$ may each combine with each of $R_{11}$ to $R_{17}$ or $L_1$ to form a ring when possible;

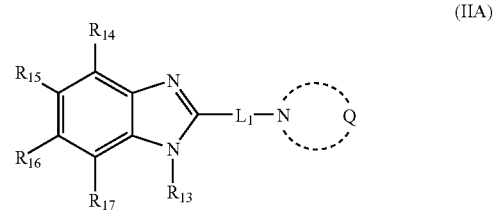

(IIA)

wherein $R_{13}$ to $R_{17}$ and $L_1$ have the same meaning as in formula (IA); Q represents an atomic group necessary for forming a 5-, 6- or 7-membered ring with N; and $R_{13}$, $R_{14}$, $R_{15}$, $R_{16}$ and $R_{17}$ may each combine with each of $R_{13}$ to $R_{17}$, the connecting group $L_1$ or the atomic group Q to form a ring.

18 Claims, No Drawings

OTHER PUBLICATIONS

1999:723021 HCAPLUS (for Nagasawa et al., WO 99/57103, Nov. 1999).

1988: 112331 HCAPLUS (for Yutilov et al., Khimiya Geterotsiklicheskikh Soedinenii, 1987).

1982: 68900 HCAPLUS (for Yutilov et al., VINITI 5441-80, 1980).

E. Fasani et al., "Hydrogen Bonding, Protonation and Twisting in the Singlet Excited State of some 2-(4-Aminophenyl)pyrido-oxa, -thia-, and -imidazoles", J. Heterocyclic Chem., vol. 30, pp. 1041-1044 (Jul.-Sep. 1993).

* cited by examiner

US 7,118,811 B2

MATERIALS FOR LIGHT EMITTING DEVICES CONSISTING OF NOVEL COMPOUNDS AND LIGHT EMITTING DEVICES USING THE SAME

CROSS REFERENCE TO RELATED APPLICATION

This is a Divisional Application of prior application Ser. No. 09/697,157 filed Oct. 27, 2000; now U.S. Pat. No. 6,620,529 the disclosure of which is incorporated herein by reference.

FIELD OF THE INVENTION

The present invention relates to novel compounds suitable for use as dyes for filters, color conversion filters, photographic material dyes, sensitizing dyes, dyes for dying pulp, laser dyes, fluorescent drugs for medical diagnoses and materials for light emitting devices, and light emitting devices using them.

BACKGROUND OF THE INVENTION

The promising uses of organic electroluminescence (EL) devices as solid light-emission type, low-priced, large-area, full color display devices result in many developments. In general, a light emitting device is composed of a light emitting layer and a pair of counter electrodes between which the light emitting layer intervenes. When an electric field is applied to between both electrodes, electrons are injected from a cathode, and holes are injected from an anode. Further, the electrons and the positive holes are recombined with each other at the light emitting layer to produce an excited state. When this excited state returns to a ground state, energy is released as light, thereby obtaining luminescence.

The conventional light emitting devices have been high in driving voltage, and low in light emitting luminance and light emitting efficiency. Further, they have also been significantly deteriorated in characteristics, so that they have not come in practice. In recent years, a light emitting device in which thin films containing an organic compound having high quantum efficiency and emitting light at a low voltage of 10 V or less are laminated with each other has been reported (*Applied Physics Letters*, 51, 913 (1987)), and an interest is centered around it. In this device, a metal chelate complex is used as an electron transfer and light emitting material, and laminated with a hole transfer material (amine compound), thereby obtaining green luminescence of high luminance. The luminance reaches thousands of candelas per centimeter square at a voltage of 6–7 V in d.c. However, when considering a practical device, the development of a light emitting device having higher luminance and efficiency has been desired. Further, when considering the utilization thereof as a full color display or a light source, it is practically necessary to give the three primary colors or white. In the above-mentioned device, an aluminum complex of 8-quinolinol (Alq) is used as the light emitting material, so that the light emitting color is green. Accordingly, the development of light emitting materials giving other light emitting colors has been desired. Various light emitting materials emitting colors other than green have hitherto been developed. However, they have the problems of low light emitting luminance and efficiency, and poor durability.

Further, the conventional devices good in color purity and high in light emitting efficiency are ones in which charge transfer materials are doped with fluorescent dyes in slight amounts, and have the problems with regard to the reproducibility of device characteristics from the production point of view, and that the long-term use thereof causes a reduction in luminance and changes in color because of low durability of the dyes. As means for solving the problems, the development of materials having both the charge transfer function and the luminescent function has been desired. However, the materials that have hitherto been developed have the problem that the use of fluorescent dyes at high concentrations leads to a reduction in luminance by association.

On the other hand, organic light emitting devices realizing luminescence of high luminance are devices laminated with organic materials by vapor deposition. The fabrication of the devices by coating is preferred from the viewpoints of simplification of manufacturing processes, processability and enlargement of area. However, the devices fabricated by the conventional coating systems are inferior in light emitting luminance and light emitting efficiency to the devices fabricated by vapor deposition. It has been therefore a great problem to make it possible to emit light of high luminance at high efficiency.

Further, recently, various substances having fluorescence have been used for dyes for filters, color conversion filters, photographic material dyes, sensitizing dyes, dyes for dying pulp, laser dyes, fluorescent drugs for medical diagnoses and materials for light emitting devices have been used, and the demand has increased for them. However, there are not so many compounds high in color purity of blue and strong in fluorescent intensity, so that the development of new materials has been desired.

SUMMARY OF THE INVENITON

It is therefore a primary object of the invention to provide materials for light emitting devices and the light emitting devices, in which luminescence of high luminance and efficiency is possible by driving at low voltage, and excellent in stability in repeated use thereof.

A secondary object of the invention is to provide light emitting devices excellent in color purity, and materials for the light emitting devices making it possible.

A third object of the invention is to provide blue light emitting materials excellent in color purity.

A fourth object of the invention is to provide compounds strong in fluorescent intensity and exhibiting blue fluorescent luminescence.

The above-mentioned objects have been attained by the following means:

(1) A material for a light emitting device consisting of a compound represented by the following general formula (IA):

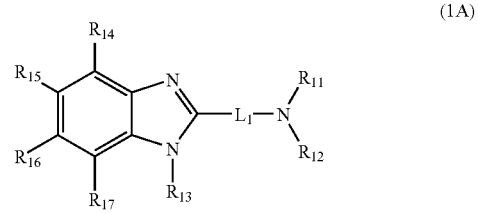

wherein $R_{11}$, $R_{12}$ and $R_{13}$ each represents a hydrogen atom, an aliphatic hydrocarbon group, an aryl group or a heterocyclic group; $L_1$ represents a connecting group; $R_{11}$ and $R_{12}$, $R_{11}$ and $L_1$, and $R_{12}$ and $L_1$ may each combine with each other to form a ring when possible; $R_{14}$, $R_{15}$, $R_{16}$ and $R_{17}$ each represents a hydrogen atom or a substituent; and $R_{13}$ to $R_{17}$ may each combine with each of $R_{11}$ to $R_{17}$ or $L_1$ to form a ring when possible;

(2) A compound represented by the following general formula (IIA):

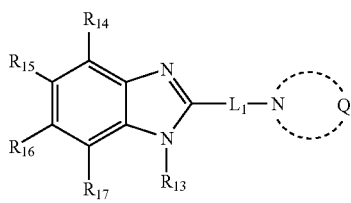

(IIA)

wherein $R_{13}$ represents a hydrogen atom, an aliphatic hydrocarbon group, an aryl group or a heterocyclic group; $L_1$ represents a connecting group; Q represents an atomic group necessary for forming a 5-, 6- or 7-membered ring with N; $R_{14}$, $R_{15}$, $R_{16}$ and $R_{17}$ each represents a hydrogen atom or a substituent; and $R_{13}$, $R_{14}$, $R_{15}$, $R_{16}$ and $R_{17}$ may each combine with each of $R_{14}$ to $R_{17}$, the connecting group $L_1$ or the atomic group Q to form a ring;

(3) A light emitting device comprising a light emitting layer or a plurality of thin organic compound layers containing a light emitting layer formed between a pair of electrodes, wherein at least one layer is a layer containing at least one of the compounds represented by general formulas (IA) and (IIA) described in (1) and (2), respectively;

(4) A light emitting device comprising a light emitting layer or a plurality of thin organic compound layers containing a light emitting layer formed between a pair of electrodes, wherein at least one layer is a layer in which at least one of the compounds represented by general formulas (IA) and (IIA) described in (1) and (2), respectively, is dispersed in a polymer;

(5) A material for a light emitting device consisting of a compound represented by the following general formula (IB):

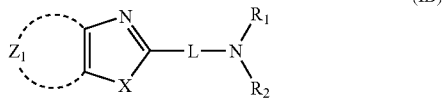

(IB)

wherein $R_1$ and $R_2$ each represents a hydrogen atom, an aliphatic hydrocarbon group, an aryl group or a heterocyclic group; $Z_1$ represents an atomic group necessary to form a heterocycle; L represents a connecting group; and X represents O, S, Se, Te or N—R, wherein R represents a hydrogen atom, an aliphatic hydrocarbon group, an aryl group or a heterocyclic group;

(6) A material for a light emitting device consisting of a compound represented by the following general formula (IIB):

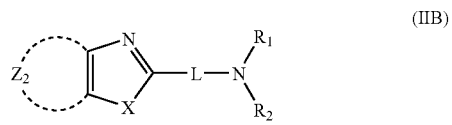

(IIB)

wherein $R_1$ and $R_2$ each represents a hydrogen atom, an aliphatic hydrocarbon group, an aryl group or a heterocyclic group; $Z_2$ represents an atomic group necessary to form an aromatic heterocycle; L represents a connecting group; and X represents O, S, Se, Te or N—R, wherein R represents a hydrogen atom, an aliphatic hydrocarbon group, an aryl group or a heterocyclic group;

(7) A material for a light emitting device consisting of a compound represented by the following general formula (III):

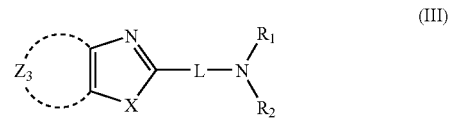

(III)

wherein $R_1$ and $R_2$ each represents a hydrogen atom, an aliphatic hydrocarbon group, an aryl group or a heterocyclic group; $Z_3$ represents an atomic group necessary to form a nitrogen-containing aromatic heterocycle; L represents a connecting group; and X represents O, S, Se, Te or N—R, wherein R represents a hydrogen atom, an aliphatic hydrocarbon group, an aryl group or a heterocyclic group;

(8) A material for a light emitting device consisting of a compound represented by the following general formula (IV):

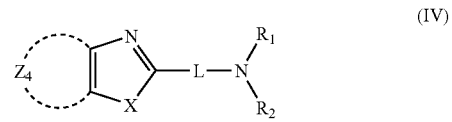

(IV)

wherein $R_1$ and $R_2$ each represents a hydrogen atom, an aliphatic hydrocarbon group, an aryl group or a heterocyclic group; $Z_4$ represents an atomic group necessary to form a 6-membered nitrogen-containing aromatic heterocycle; L represents a connecting group; and X represents O, S, Se, Te or N—R, wherein R represents a hydrogen atom, an aliphatic hydrocarbon group, an aryl group or a heterocyclic group;

(9) A material for a light emitting device consisting of a compound represented by the following general formula (V):

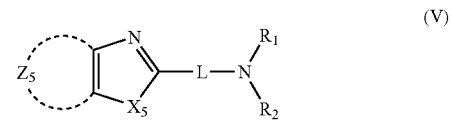

(V)

wherein $R_1$ and $R_2$ each represents a hydrogen atom, an aliphatic hydrocarbon group, an aryl group or a heterocyclic group; $Z_5$ represents an atomic group necessary to form a 6-membered nitrogen-containing aromatic heterocycle; L represents a connecting group; and $X_5$ represents O, S or N—R, wherein R represents a hydrogen atom, an aliphatic hydrocarbon group, an aryl group or a heterocyclic group;

(10) A material for a light emitting device consisting of a compound represented by the following general formula (VI):

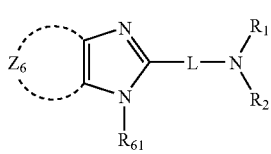

wherein $R_1$, $R_2$ and $R_{61}$ each represents a hydrogen atom, an aliphatic hydrocarbon group, an aryl group or a heterocyclic group; $Z_6$ represents an atomic group necessary to form a 6-membered nitrogen-containing aromatic heterocycle; and L represents a connecting group;

(11) A material for a light emitting device consisting of a compound represented by the following general formula (VII):

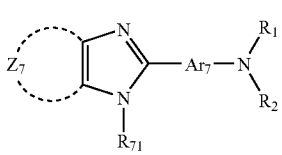

wherein $R_1$, $R_2$ and $R_{71}$ each represents a hydrogen atom, an aliphatic hydrocarbon group, an aryl group or a heterocyclic group; $Z_7$ represents an atomic group necessary to form a 6-membered nitrogen-containing aromatic heterocycle; and $Ar_7$ represents arylene or a divalent aromatic heterocycle;

(12) A compound represented by the following general formula (VIII):

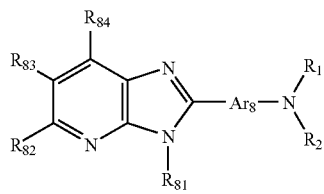

wherein $R_1$, $R_2$ and $R_{81}$ each represents a hydrogen atom, an aliphatic hydrocarbon group, an aryl group or a heterocyclic group; $R_{82}$, $R_{83}$ and $R_{84}$ each represents a hydrogen atom or a substituent, and $Ar_8$ represents arylene or a divalent aromatic heterocycle;

(13) A material for a light emitting device consisting of a compound represented by the following general formula (VIII):

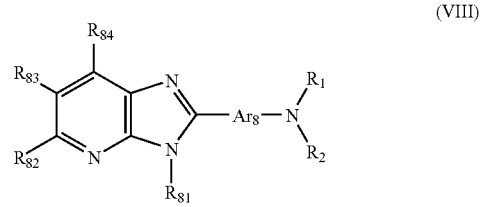

wherein $R_1$, $R_2$ and $R_{81}$ each represents a hydrogen atom, an aliphatic hydrocarbon group, an aryl group or a heterocyclic group; $R_{82}$, $R_{83}$ and $R_{84}$ each represents a hydrogen atom or a substituent, and $Ar_8$ represents arylene or a divalent aromatic heterocycle;

(14) A compound represented by the following general formula (IX):

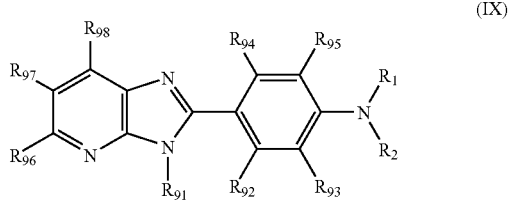

wherein $R_1$, $R_2$ and $R_{91}$ each represents a hydrogen atom, an aliphatic hydrocarbon group, an aryl group or a heterocyclic group; and $R_{92}$, $R_{93}$, $R_{94}$, $R_{95}$, $R_{96}$, $R_{97}$ and $R_{98}$ each represents a hydrogen atom or a substituent;

(15) A material for a light emitting device consisting of a compound represented by the following general formula (IX):

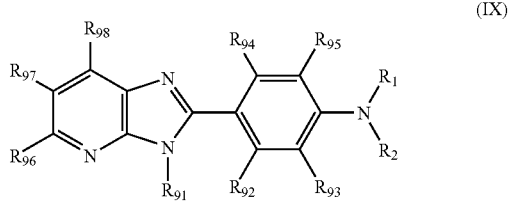

wherein $R_1$, $R_2$ and $R_{91}$ each represents a hydrogen atom, an aliphatic hydrocarbon group, an aryl group or a heterocyclic group; and $R_{92}$, $R_{93}$, $R_{94}$, $R_{95}$, $R_{96}$, $R_{97}$ and $R_{98}$ each represents a hydrogen atom or a substituent;

(16) A compound represented by the following general formula (X):

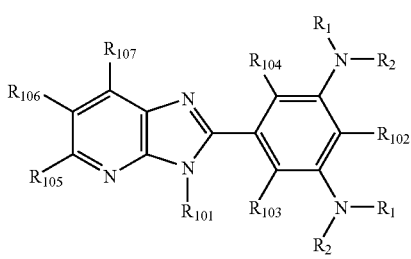

wherein $R_1$, $R_2$ and $R_{101}$ each represents a hydrogen atom, an aliphatic hydrocarbon group, an aryl group or a heterocyclic group; and $R_{102}$, $R_{103}$, $R_{104}$, $R_{105}$, $R_{106}$ and $R_{107}$ each represents a hydrogen atom or a substituent;

(17) A material for a light emitting device consisting of a compound represented by the following general formula (X):

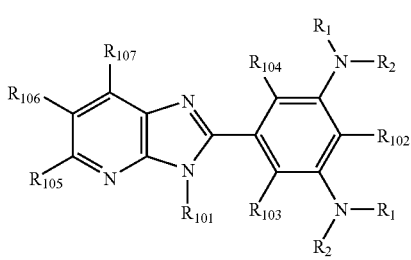

wherein $R_1$, $R_2$ and $R_{101}$ each represents a hydrogen atom, an aliphatic hydrocarbon group, an aryl group or a heterocyclic group; and $R_{102}$, $R_{103}$, $R_{104}$, $R_{105}$, $R_{106}$ and $R_{107}$ each represents a hydrogen atom or a substituent;

(18) A compound represented by the following general formula (XI):

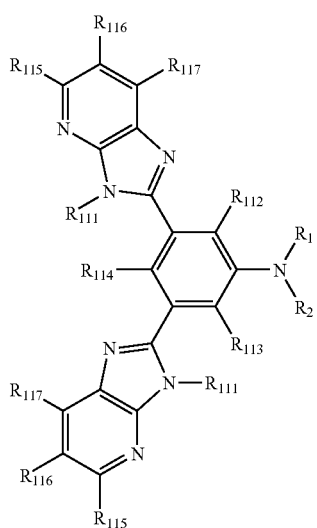

wherein $R_1$, $R_2$ and $R_{111}$ each represents a hydrogen atom, an aliphatic hydrocarbon group, an aryl group or a heterocyclic group; and $R_{112}$, $R_{113}$, $R_{114}$, $R_{115}$, $R_{116}$ and $R_{117}$ each represents a hydrogen atom or a substituent;

(19) A material for a light emitting device consisting of a compound represented by the following general formula (XI):

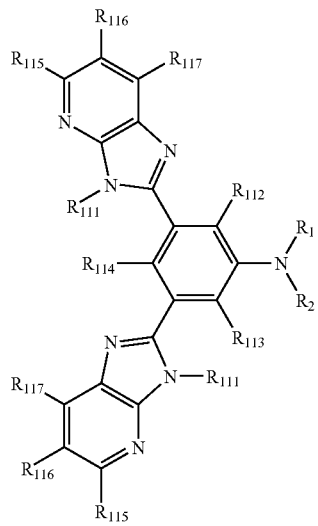

wherein $R_1$, $R_2$ and $R_{111}$ each represents a hydrogen atom, an aliphatic hydrocarbon group, an aryl group or a heterocyclic group; and $R_{112}$, $R_{113}$, $R_{114}$, $R_{115}$, $R_{116}$ and $R_{117}$ each represents a hydrogen atom or a substituent;

(20) A light emitting device comprising a light emitting layer or a plurality of thin organic compound layers containing a light emitting layer formed between a pair of electrodes, wherein at least one layer is a layer containing at least one of the compounds represented by general formulas (IB), (IIB) and (III) to (XI) described in (5) to (19), respectively; and

(21) A light emitting device comprising a light emitting layer or a plurality of thin organic compound layers containing a light emitting layer formed between a pair of electrodes, wherein at least one layer is a layer in which at least one of the compounds represented by general formulas (IB), (IIB) and (III) to (XI) described in (5) to (19), respectively, is dispersed in a polymer.

DETAILED DESCRIPTION OF THE INVENTION

The invention will be described in detail below.

First, the compounds of the invention represented by general formula (IA) will be described.

$R_{11}$ and $R_{12}$, which may the same or different, each represents a hydrogen atom, an aliphatic hydrocarbon group, an aryl group or a heterocyclic group. Further, $R_{11}$ and $R_{12}$, $R_{11}$ and $L_1$, and $R_{12}$ and $L_1$ may each combine with each other to form a ring when possible.

The aliphatic hydrocarbon groups represented by $R_{11}$ and $R_{12}$ include a straight-chain, branched or cyclic alkyl group (having preferably from 1 to 30 carbon atoms, more preferably from 1 to 20 carbon atoms, and still more preferably from 1 to 12 carbon atoms, e.g., methyl, ethyl, iso-propyl, n-butyl, tert-butyl, n-octyl, n-decyl, n-hexadecyl, cyclopropyl, cyclopentyl or cyclohexyl), an alkenyl group (having preferably from 2 to 30 carbon atoms, more preferably from 2 to 20 carbon atoms, and still more preferably from 2 to 12 carbon atoms, e.g., vinyl, allyl, 2-butenyl or 3-pentenyl) and an alkynyl group (having preferably from 2 to 30 carbon atoms, more preferably from 2 to 20 carbon atoms, and still more preferably from 2 to 12 carbon atoms, e.g., propargyl or 3-pentynyl). Preferred are the alkyl group and the alkenyl group, and more preferred is methyl, ethyl, propyl, butyl, allyl or a condensed ring formed by bonding of $R_{11}$ and $R_{12}$ with $L_1$ (e.g., a julolidine ring).

The aryl groups represented by $R_{11}$ and $R_{12}$ are preferably monocyclic or bicyclic aryl groups each having from 6 to 30 carbon atoms (e.g., phenyl and naphthyl). More preferred are phenyl having from 6 to 20 carbon atoms and naphthyl having from 10 to 24 carbon atoms, and still more preferred are phenyl having from 6 to 12 carbon atoms and naphthyl having from 10 to 16 carbon atoms.

The heterocyclic groups represented by $R_{11}$ and $R_{12}$ are 3- to 10-membered saturated or unsaturated heterocyclic groups each having at least one of N, O and S atoms. They may be monocyclic or may form condensed rings with other rings.

The heterocyclic groups are preferably 5- to 10-membered aromatic heterocyclic groups each having at least one of nitrogen, oxygen, sulfur and selenium atoms, more preferably 5- or 6-membered aromatic heterocyclic groups, and still more preferably 5- or 6-membered aromatic heterocyclic groups each having an N atom or an S atom.

Specific examples of the heterocyclic groups include pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzthiazole, benzotriazole and tetraazaindene. Preferred are thiophene, triazole, oxazole, pyridine, triazine and quinoline, more preferred are thiophene, pyridine, triazine and quinoline, and still more preferred is thiophene.

The aliphatic hydrocarbon groups, aryl groups and heterocyclic groups represented by $R_{11}$ and $R_{12}$ may have substituents. Examples of the substituents include an alkyl group (having preferably from 1 to 20 carbon atoms, more preferably from 1 to 12 carbon atoms, and particularly preferably from 1 to 8 carbon atoms, e.g., methyl, ethyl, iso-propyl, tert-butyl, n-octyl, n-decyl, n-hexadecyl, cyclopropyl, cyclopentyl or cyclohexyl), an alkenyl group (having preferably from 2 to 20 carbon atoms, more preferably from 2 to 12 carbon atoms, and particularly preferably from 2 to 8 carbon atoms, e.g., vinyl, allyl, 2-butenyl or 3-pentenyl), an alkynyl group (having preferably from 2 to 20 carbon atoms, more preferably from 2 to 12 carbon atoms, and particularly preferably from 2 to 8 carbon atoms, e.g., propargyl or 3-pentynyl), an aryl group (having preferably from 6 to 30 carbon atoms, more preferably from 6 to 20 carbon atoms, and particularly preferably from 6 to 12 carbon atoms, e.g., phenyl, p-methylphenyl or naphthyl), an amino group (having preferably from 0 to 20 carbon atoms, more preferably from 0 to 12 carbon atoms, and particularly preferably from 0 to 6 carbon atoms, e.g., amino, methylamino, dimethylamino, diethylamino, diphenylamino or dibenzylamino), an alkoxyl group (having preferably from 1 to 20 carbon atoms, more preferably from 1 to 12 carbon atoms, and particularly preferably from 1 to 8 carbon atoms, e.g., methoxy, ethoxy or butoxy), an aryloxy group (having preferably from 6 to 20 carbon atoms, more preferably from 6 to 16 carbon atoms, and particularly preferably from 6 to 12 carbon atoms, e.g., phenyloxy or 2-naphtyloxy), an acyl group (having preferably from 1 to 20 carbon atoms, more preferably from 1 to 16 carbon atoms, and particularly preferably from 1 to 12 carbon atoms, e.g., acetyl, benzoyl, formyl or pivaloyl), an alkoxycarbonyl groups (having preferably from 2 to 20 carbon atoms, more preferably from 2 to 16 carbon atoms, and particularly preferably from 2 to 12 carbon atoms, e.g., methoxycarbonyl or ethoxycarbonyl), an aryloxycarbonyl group (having preferably from 7 to 20 carbon atoms, more preferably from 7 to 16 carbon atoms, and particularly preferably from 7 to 10 carbon atoms, e.g., phenyloxycarbonyl), an acyloxy group (having preferably from 2 to 20 carbon atoms, more preferably from 2 to 16 carbon atoms, and particularly preferably from 2 to 10 carbon atoms, e.g., acetoxy or benzoyloxy), an acylamino group (having preferably from 2 to 20 carbon atoms, more preferably from 2 to 16 carbon atoms, and particularly preferably from 2 to 10 carbon atoms, e.g., acetylamio or benzoylamino), an alkoxycarbonylamino group (having preferably from 2 to 20 carbon atoms, more preferably from 2 to 16 carbon atoms, and particularly preferably from 2 to 12 carbon atoms, e.g., methoxy-carbonylamino), an aryloxycarbonylamino group (having preferably from 7 to 20 carbon atoms, more preferably from 7 to 16 carbon atoms, and particularly preferably from 7 to 12 carbon atoms, e.g., phenyloxycarbonylamino), a sulfonylamino group (having preferably from 1 to 20 carbon atoms, more preferably from 1 to 16 carbon atoms, and particularly preferably from 1 to 12 carbon atoms, e.g., methanesulfonylamino or benzenesulfonylamino), a sulfamoyl group (having preferably from 0 to 20 carbon atoms, more preferably from 0 to 16 carbon atoms, and particularly preferably from 0 to 12 carbon atoms, e.g., sulfamoyl, methylsulfamoyl, dimethylsulfamoyl or phenylsulfamoyl), a carbamoyl group (having preferably from 1 to 20 carbon atoms, more preferably from 1 to 16 carbon atoms, and particularly preferably from 1 to 12 carbon atoms, e.g., carbamoyl, methylcarbamoyl, diethylcarbamoyl or phenylcarbamoyl), an alkylthio group (having preferably from 1 to 20 carbon atoms, more preferably from 1 to 16 carbon atoms, and particularly preferably from 1 to 12 carbon atoms, e.g., methylthio or ethylthio), an arylthio group (having preferably from 6 to 20 carbon atoms, more preferably from 6 to 16 carbon atoms, and particularly preferably from 6 to 12 carbon atoms, e.g., phenylthio), a sulfonyl group (having preferably from 1 to 20 carbon atoms, more preferably from 1 to 16 carbon atoms, and particularly preferably from 1 to 12 carbon atoms, e.g., mesyl or tosyl), a sulfinyl group (having preferably from 1 to 20 carbon atoms, more preferably from 1 to 16 carbon atoms, and particularly preferably from 1 to 12 carbon atoms, e.g., methanesulfinyl or benzenesulfinyl), a ureido group (having preferably from 1 to 20 carbon atoms, more preferably from 1 to 16 carbon atoms, and particularly preferably from 1 to 12 carbon atoms, e.g., ureido, methylureido or phenylureido), a phosphoric acid amide group (having preferably from 1 to 20 carbon atoms, more preferably from 1 to 16 carbon atoms, and particularly preferably from 1 to 12 carbon atoms, e.g., diethylphosphoric acid amide or phenylphosphoric acid amide), a hydroxyl group, a mercapto group, a halogen atom (e.g., fluorine, chlorine, bromine or iodine), a cyano group, a sulfo group, a carboxyl group, a nitro group, a hydroxamic acid group, a sulfino group, a hydrazine group, an imino group, a heterocyclic group (having preferably from 1 to 30 carbon atoms, and more preferably from 1 to 12 carbon atoms, having a heteroatom, e.g., nitrogen, oxygen or sulfur, and specifically including imidazolyl, pyridyl, quinolyl, furyl, thienyl, piperidyl, morpholino, benzoxazolyl, benzimidazolyl or benzthiazolyl), and a silyl group (having preferably from 3 to 40 carbon atoms, more preferably from 3 to 30 carbon atoms, and particularly preferably from 3 to 24 carbon atoms, e.g., trimethylsilyl or triphenylsilyl). These substituents may be further substituted. When there are two or more substituents, they may be the same or different. Further, they may combine with each other to form a ring when possible.

$R_{11}$ and $R_{12}$ are each preferably a hydrogen atom, an alkyl group, an aryl group and an aromatic heterocyclic group. When the compounds are used as charge transfer materials and concurrently light emitting materials (non-dope type), $R_{11}$ and $R_{12}$ are each preferably an aryl group and an aromatic heterocyclic group, and more preferably an aryl group (preferably a monocyclic or bicyclic aryl group having from 6 to 30 carbon atoms, more preferably phenyl or naphthyl having from 6 to 20 carbon atoms, and still more preferably phenyl or naphthyl having from 6 to 12 carbon atoms). When the compounds are used as dope type light emitting materials, $R_{11}$ and $R_{12}$ are each preferably a hydrogen atom, an alkyl group or an alkylene group combining with $L_1$ to form a ring, more preferably an alkyl group or an alkylene group combining with $L_1$ to form a ring, and still more preferably an alkyl group having from 1 to 8 carbon toms or an alkylene group combining with $L_1$ to form a 6-membered ring. Particularly preferred are methyl, ethyl and the alkylene group combining with $L_1$ to form a 6-membered ring (e.g., trimethylene and 3,3-dimethyltrimethylene).

$R_{13}$ represents a hydrogen atom, an aliphatic hydrocarbon group, an aryl group or a heterocyclic group. The aliphatic hydrocarbon group represented by $R_{13}$ is preferably an alkyl group (having preferably from 1 to 20 carbon atoms, more preferably from 1 to 12 carbon atoms, and particularly preferably from 1 to 8 carbon atoms, e.g., methyl, ethyl, iso-propyl, tert-butyl, n-octyl, n-decyl, n-hexadecyl, cyclopropyl, cyclopentyl or cyclohexyl), an alkenyl group (having preferably from 2 to 20 carbon atoms, more preferably from 2 to 12 carbon atoms, and particularly preferably from 2 to 8 carbon atoms, e.g., vinyl, allyl, 2-butenyl or 3-pentenyl), or an alkynyl group (having preferably from 2 to 20 carbon atoms, more preferably from 2 to 12 carbon atoms, and still more preferably from 2 to 8 carbon atoms, e.g., propargyl or 3-pentynyl), and more preferably an alkyl group.

The aryl group represented by $R_{13}$ has from 6 to 30 carbon atoms, more preferably from 6 to 20 carbon atoms, and particularly preferably from 6 to 12 carbon atoms. Examples thereof include phenyl, p-methylphenyl, m-methylphenyl, o-methylphenyl, p-phenylphenyl, m-phenylphenyl, o-phenylphenyl, p-methoxyphenyl, m-methoxyphenyl, o-methoxyphenyl, 2,6-dimethylphenyl, 2,6-diphenylphenyl, 2,4,6-trimethylphenyl, m-trifluoromethylphenyl, pentafluorophenyl, 1-naphthyl and 2-naphthyl.

The heterocyclic group represented by $R_{13}$ is a monocyclic or condensed heterocyclic group (a heterocyclic group having from 1 to 20 carbon atoms, more preferably from 1 to 12 carbon atoms, and still more preferably from 2 to 10 carbon atoms), and preferably an aromatic heterocyclic group containing at least one of nitrogen, oxygen, sulfur and selenium atoms. Specific examples of the heterocyclic group represented by $R_{13}$ include pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzthiazole, benzotriazole and tetraazaindene. Preferred are furan thiophene, pyridine, pyrazine, pyrimidine, pyridazine, triazine, quinoline, phthalazine, naphthyridine, quinoxaline, and quinazoline, and more preferred are furan, thiophene, pyridine and quinoline.

The aliphatic hydrocarbon groups, aryl groups and heterocyclic groups group represented by $R_{13}$ may have substituents. As the substituents, the substituents described above for the groups represented by $R_{11}$ and $R_{12}$ can be applied, and preferred substituents are also the same as given therefor.

$R_{13}$ is preferably an alkyl group, an aryl group or an aromatic heterocyclic group, more preferably an aryl group or an aromatic heterocyclic group, and still more preferably an aryl group or an aromatic azole group.

$R_{14}$, $R_{15}$, $R_{16}$ and $R_{17}$ each represents a hydrogen atom or a substituent. As the substituents, the substituents described above for $R_{11}$ and $R_{12}$ in general formula (IA) can be applied, and preferred examples of $R_{14}$, $R_{15}$, $R_{16}$ and $R_{17}$ include a hydrogen atom, an alkyl group, an alkenyl group, an alkynyl group, an aryl group, an alkoxyl group, an aryloxy group, an acyl group, a halogen atom, a cyano group, a heterocyclic group and a silyl group. More preferred are a hydrogen atom, an alkyl group, an alkenyl group, an alkynyl group, an aryl group, an alkoxyl group, an aryloxy group, a halogen atom, a cyano group and an aromatic heterocyclic group, still more preferred are a hydrogen atom, an alkyl group, an aryl group and an aromatic heterocyclic group, and particularly preferred is a hydrogen atom. Further, the substituents may combine with each other, or the substituent may combine with the connecting group $L_1$ to form a ring when possible.

$L_1$ represents a connecting group. The connecting group represented by $L_1$ is preferably a connecting group formed by a single bond, C, N, O, S, Se, Te, Si or Ge, more preferably a group comprising a single bond, alkylene, alkenylene, alkynylene, arylene, a divalent heterocycle (preferably an aromatic heterocycle, and more preferably an aromatic heterocycle formed by an azole, thiophene or furan ring) or a combination thereof with N, and still more preferably a group comprising arylene, a divalent aromatic heterocycle or a combination thereof with N. Yet still more preferred is a group comprising a phenylene group, a thenylene group or a combination thereof with N, and particularly preferred is a phenylene group. Further, $L_1$ may combine with $R_{11}$ to $R_{17}$ to form a ring.

Specific examples of the connecting groups represented by $L_1$ include the following groups as well as a single bond.

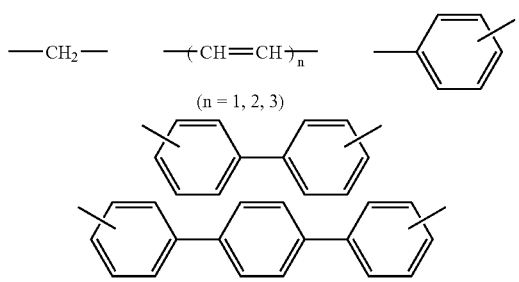

-continued
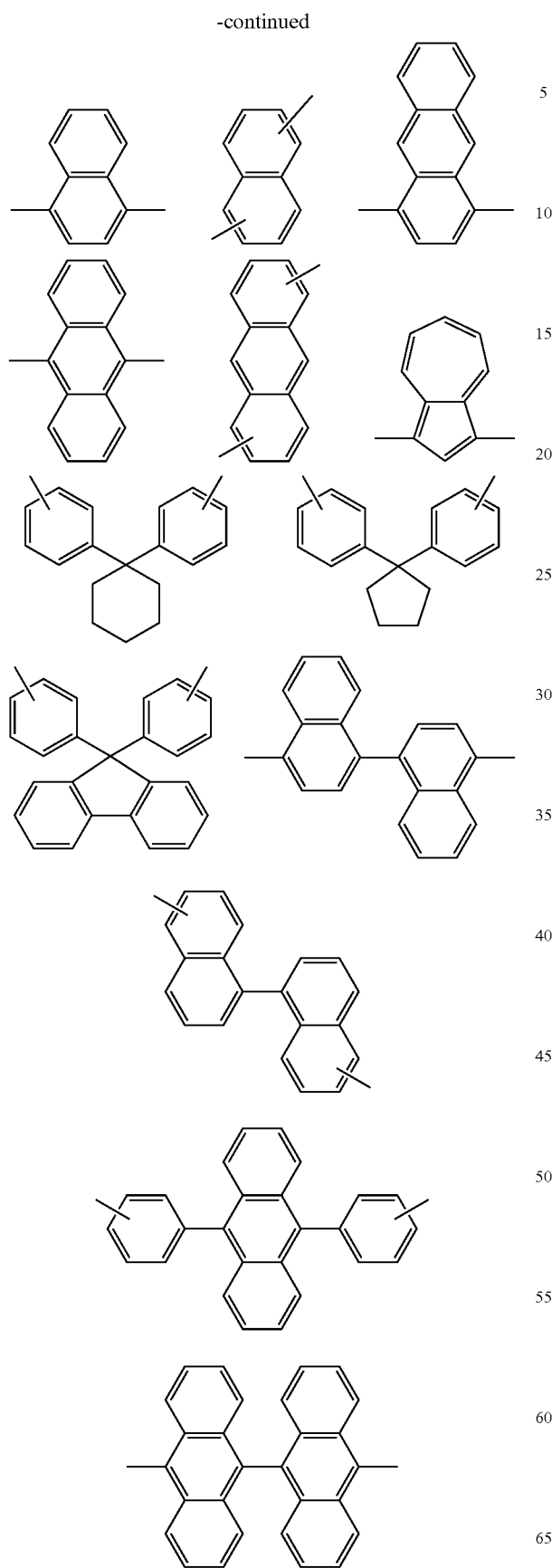
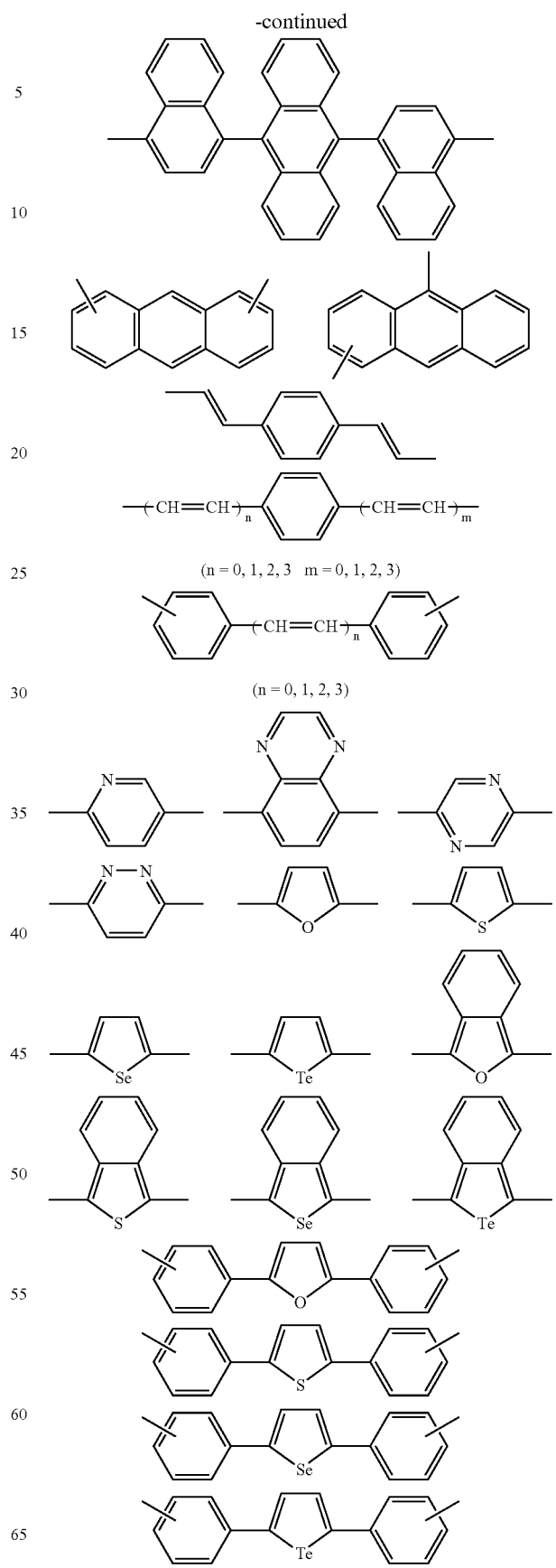
(n = 0, 1, 2, 3   m = 0, 1, 2, 3)
(n = 0, 1, 2, 3)

-continued
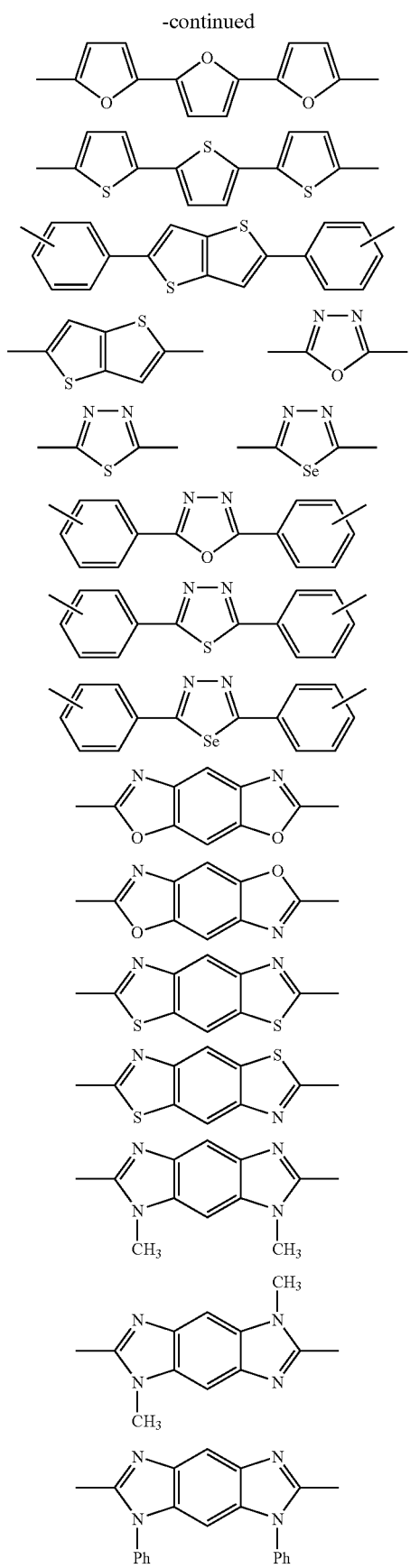
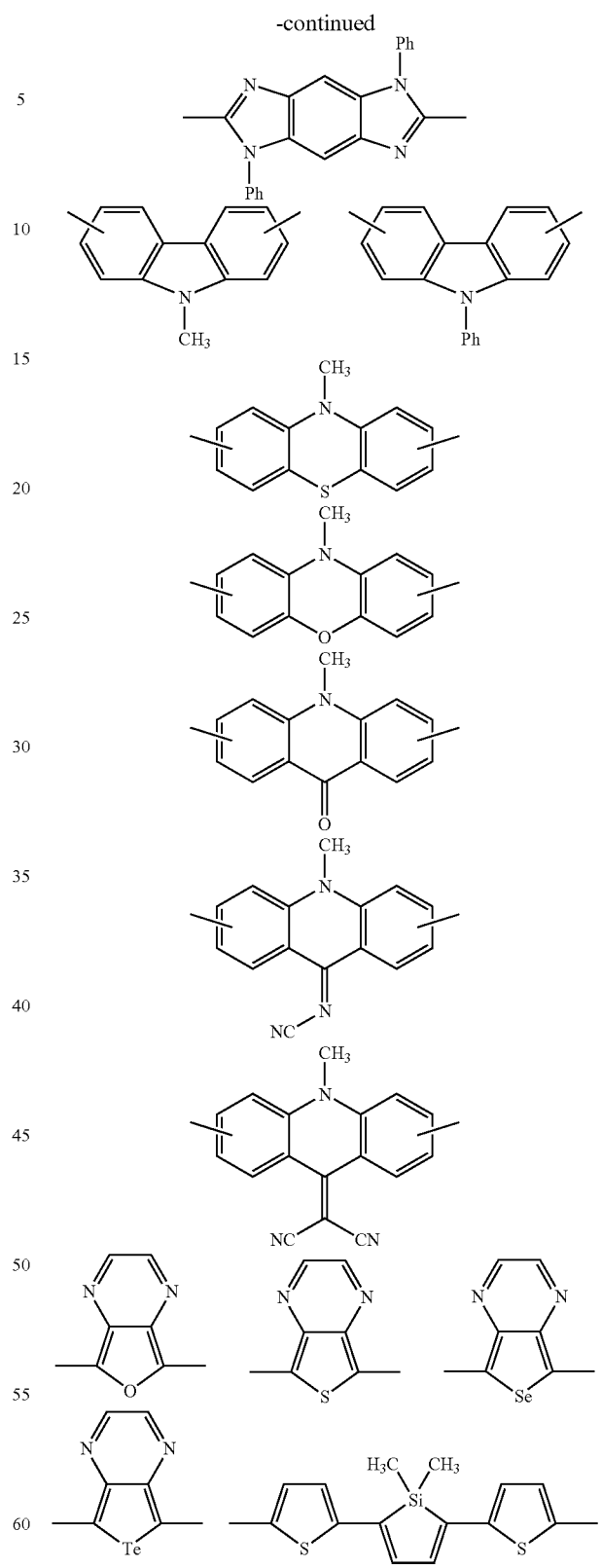
The connecting groups represented by $L_1$ may have substituents. As the substituents, for example, the substituents described above for the groups represented by $R_{11}$ and $R_{12}$ can be applied. Preferred examples of the substituents for $L_1$ include an alkyl group, an alkenyl group, an alkynyl group, an aryl group, an alkoxyl group, an aryloxy group, an acyl group, a halogen atom, a cyano group, a heterocyclic group and a silyl group. More preferred are an alkyl group, an alkenyl group, an alkynyl group, an aryl group, an alkoxyl group, an aryloxy group, a halogen atom, a cyano group and an aromatic heterocyclic group, and still more preferred are an alkyl group, an aryl group and an aromatic heterocyclic group.

Of the compounds represented by general formula (IA), compounds represented by the following general formula (IIA) are preferred.

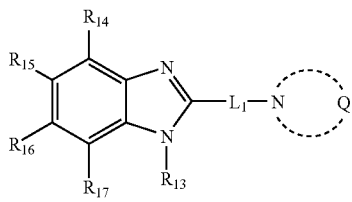

(IIA)

$R_{13}$, $R_{14}$, $R_{15}$, $R_{16}$, $R_{17}$ and $L_1$ each has the same meaning as given for general formula (IA), and each preferred range is also the same as given therefor.

Q represents an atomic group necessary to form a 5-, 6- or 7-membered nitrogen-containing heterocycle by combining with N.

The 5- to 7-membered nitrogen-containing heterocycles formed by Q and N include a pyrrole ring, an azepine ring, a piperidine ring, a pyrrolidine ring, a piperazine ring, a morpholine ring, a thiomorpholine ring and a hexamethyleneimine ring, and preferred are a pyrrole ring and an azepine ring.

The 5- to 7-membered nitrogen-containing heterocycles formed by Q and N may further combine with other rings to form condensed rings, and may also have substituents. The condensed rings include, for example, a benzene ring, a thiophene ring, a pyrrole ring, a furan ring, a selenophene ring, a pyridine ring, a pyrazine ring, a pyrimidine ring, a pyridazine ring, an imidazole ring, an oxazole ring and a thiazole ring. Preferred are a benzene ring, a thiophene ring, a pyridine ring and a pyrazine ring, more preferred are a benzene ring and a thiophene ring, and particularly preferred is a benzene ring. As the substituents, for example, the substituents described above for the groups represented by $R_{11}$ and $R_{12}$ can be applied. Preferred examples of the substituents for Q include an alkyl group, an alkenyl group, an alkynyl group, an aryl group, an amino group, an alkoxyl group, an aryloxy group, an acyl group, a alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group and a heterocyclic group. More preferred are an alkyl group, an alkenyl group, an aryl group, an alkoxyl group, an aryloxy group, a halogen atom, a cyano group and a heterocyclic group, still more preferred are an alkyl group, an aryl group, an alkoxyl group, an aryloxy group and an aromatic heterocyclic group, and particularly preferred are an alkyl group, an aryl group, an alkoxyl group and an aromatic heterocyclic group.

Specific examples of the 5- to 7-membered rings formed by Q and N include, for example, the following.

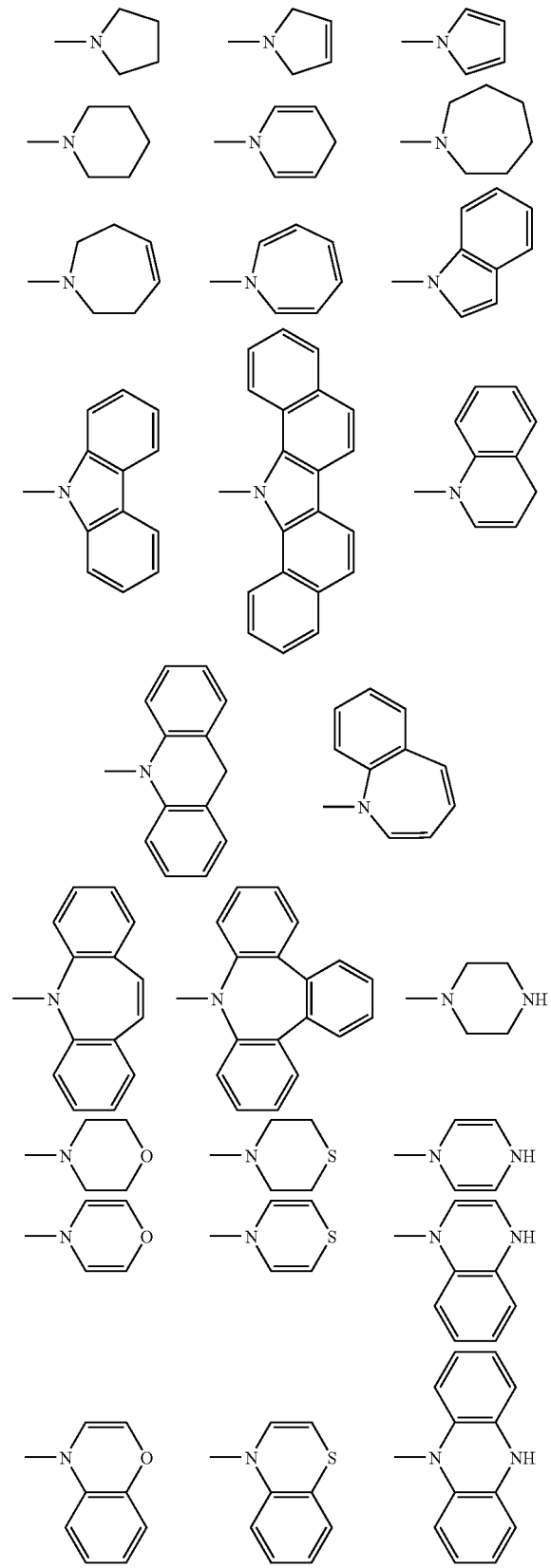

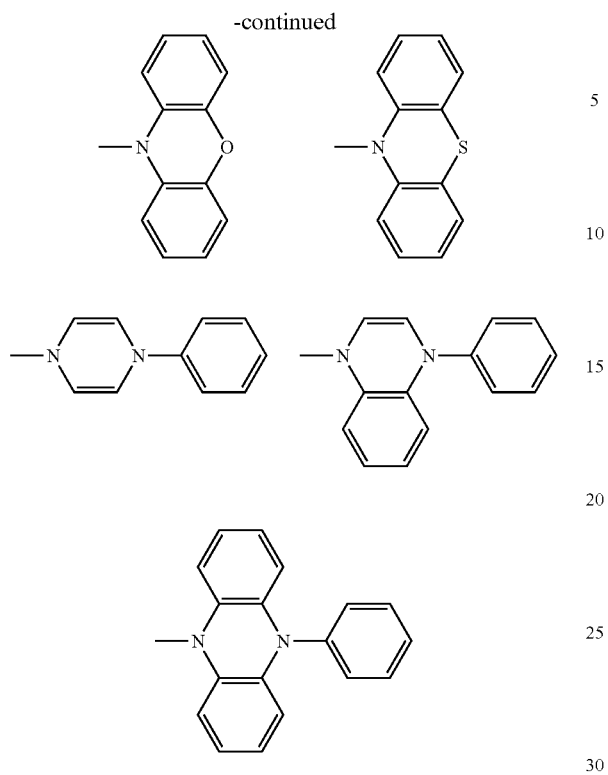

The compounds represented by general formulas (IA) and (IIA) may be either low molecular weight compounds, or high molecular weight compounds in which residues are connected to main chains of polymers (the weight-average molecular weight of the compounds is preferably from 1,000 to 5,000,000, more preferably from 5,000 to 2,000,000, and still more preferably from 10,000 to 1,000,000) or high molecular weight compounds having the compounds of the invention as main chains (the weight-average molecular weight of the compounds is preferably from 1,000 to 5,000,000, more preferably from 5,000 to 2,000,000, and still more preferably from 10,000 to 1,000,000). In the case of the high molecular weight compounds, they may be either homopolymers or copolymers with other polymers. In the case of the copolymers, they may be either random copolymers or block copolymers. The compounds used in the invention are preferably the low molecular weight compounds.

Specific examples of the compounds of the invention represented by general formula (IA) are shown below, but it is to be understood that the invention is not limited thereto.

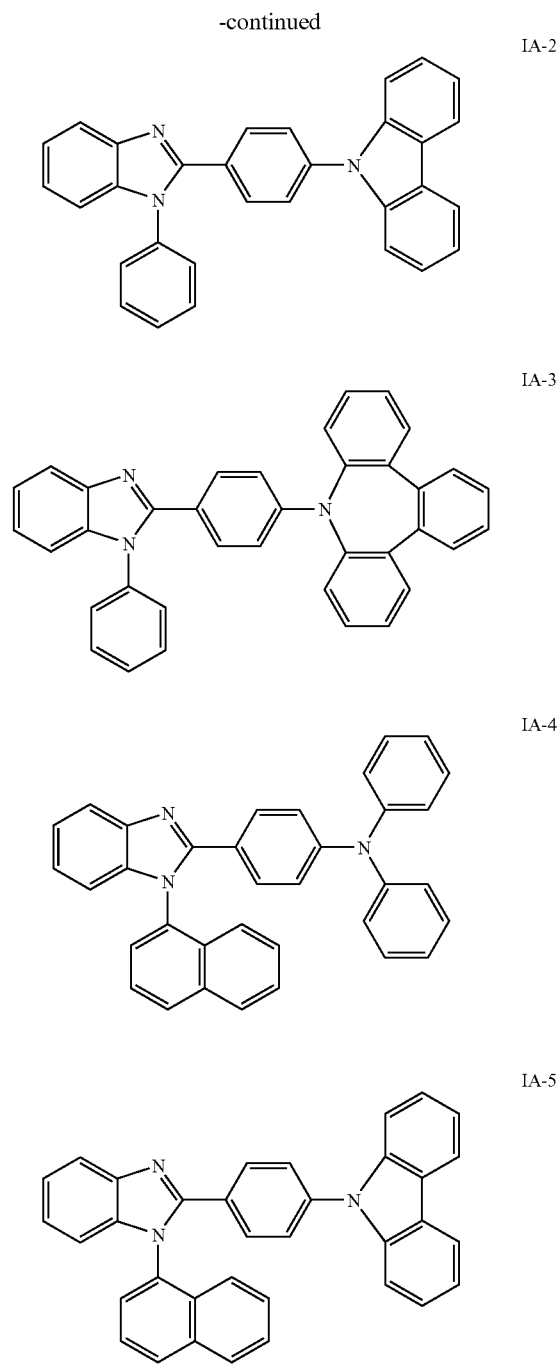

-continued
IA-7
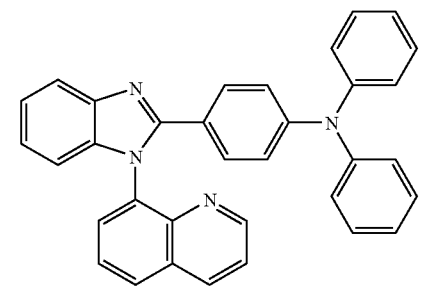
IA-8
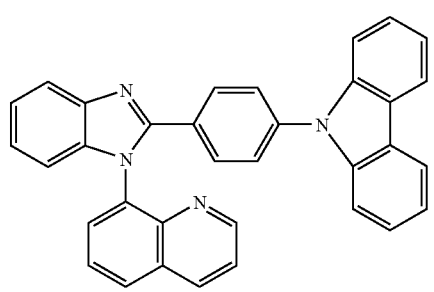
IA-9
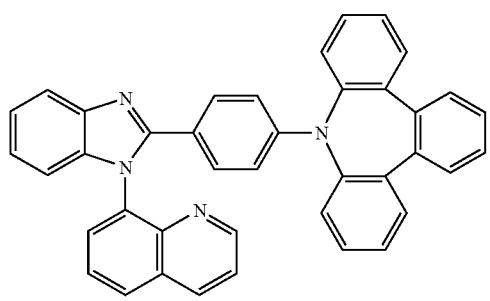
IA-10
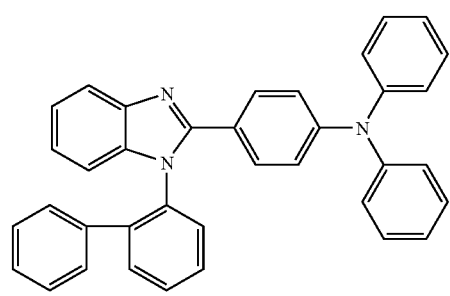
IA-11
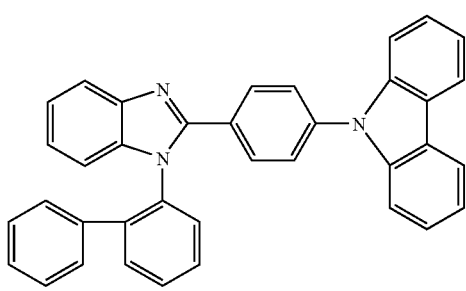
-continued
IA-12
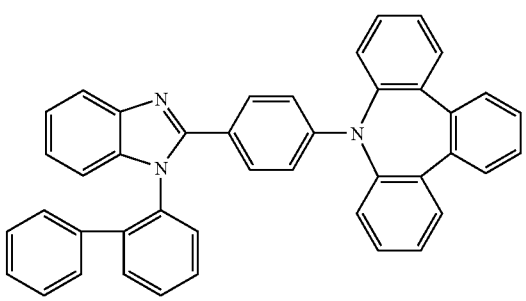
IA-13
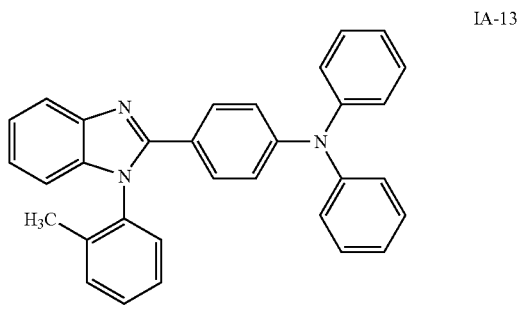
IA-14
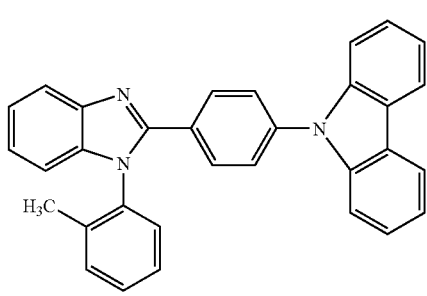
IA-15
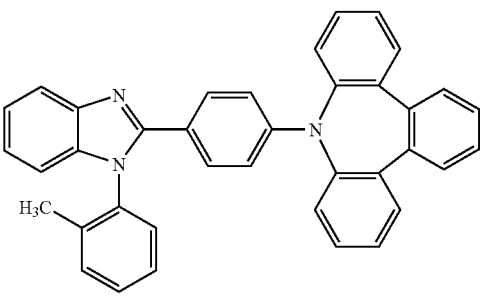
IA-16
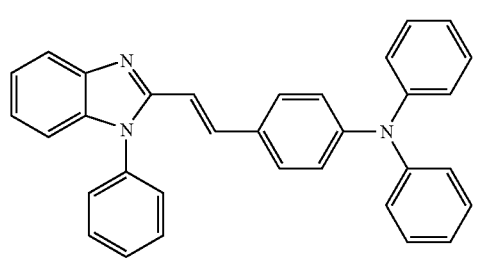

IA-17
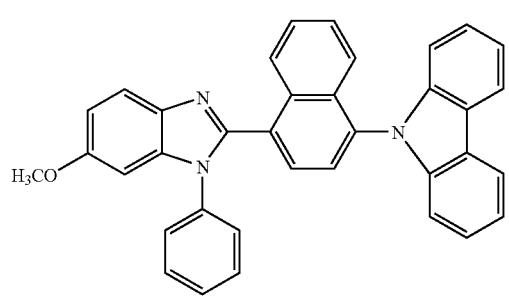
IA-18
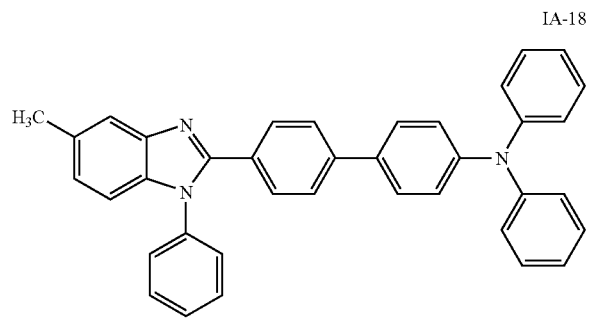
IA-19
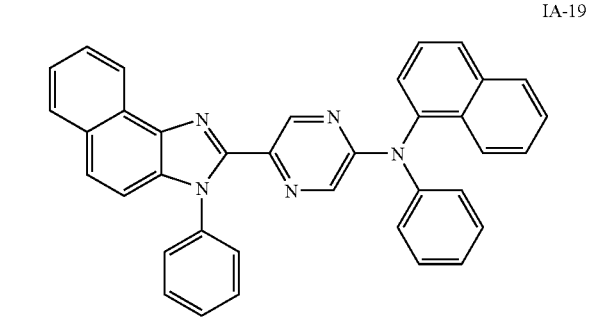
IA-20
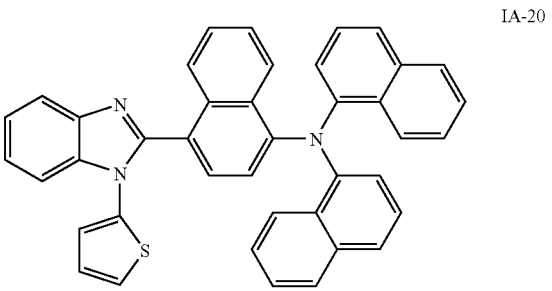
IA-21
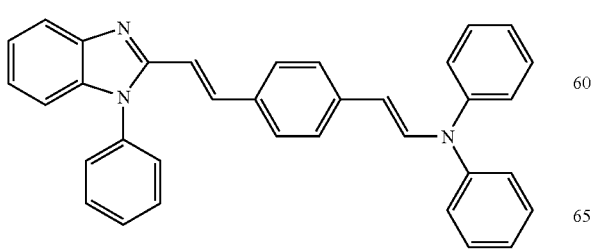
IA-22
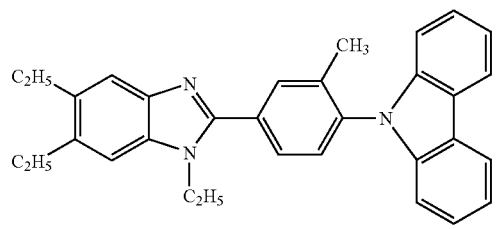
IA-23
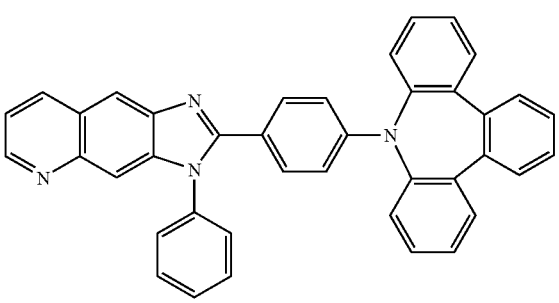
IA-24
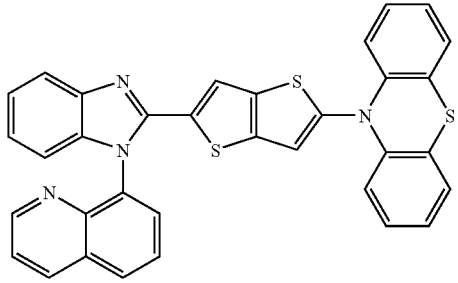
IA-25
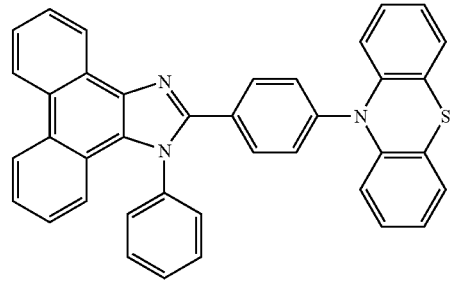
IA-26
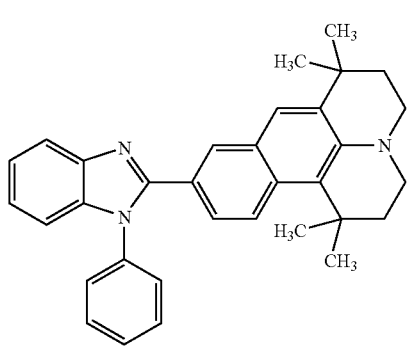

-continued
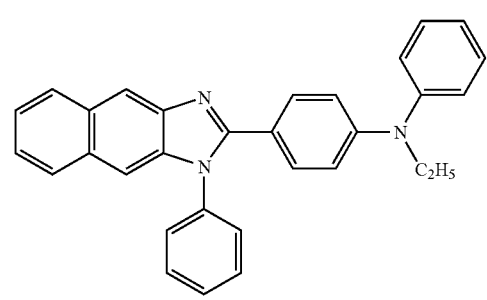
IA-27
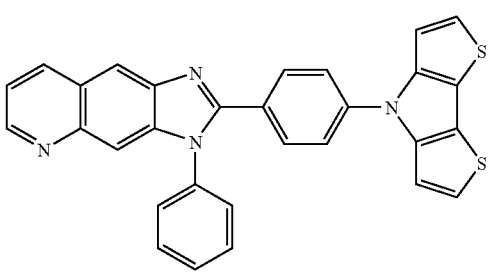
IA-32
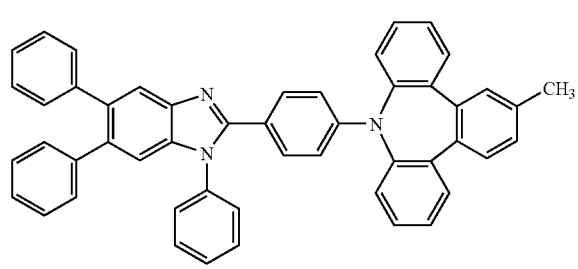
IA-28
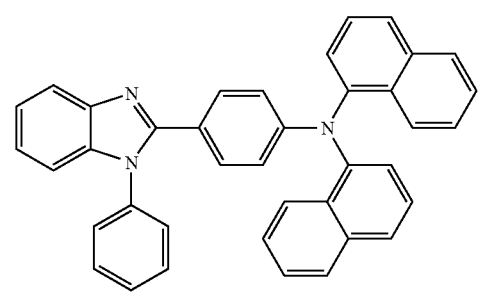
IA-33
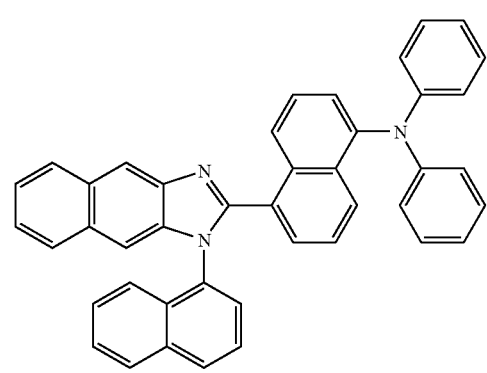
IA-29
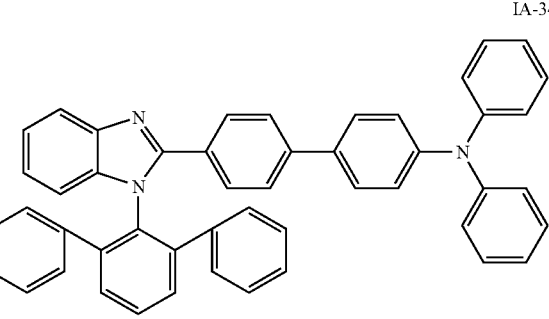
IA-34
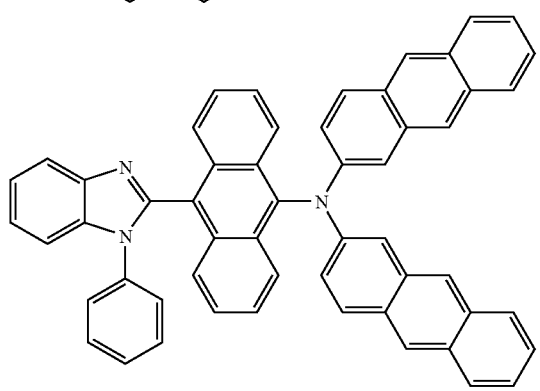
IA-30
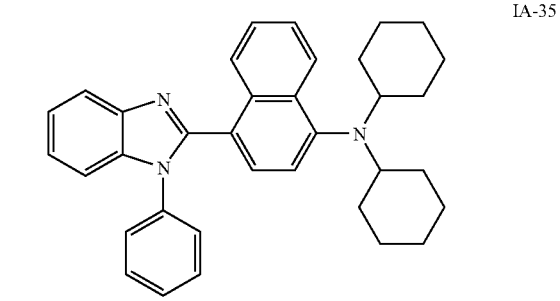
IA-35
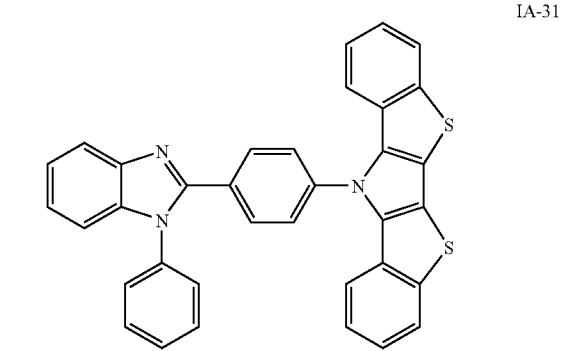
IA-31
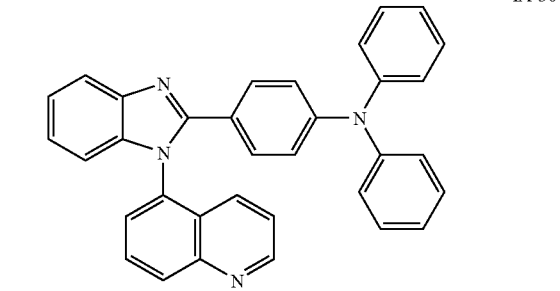
IA-36

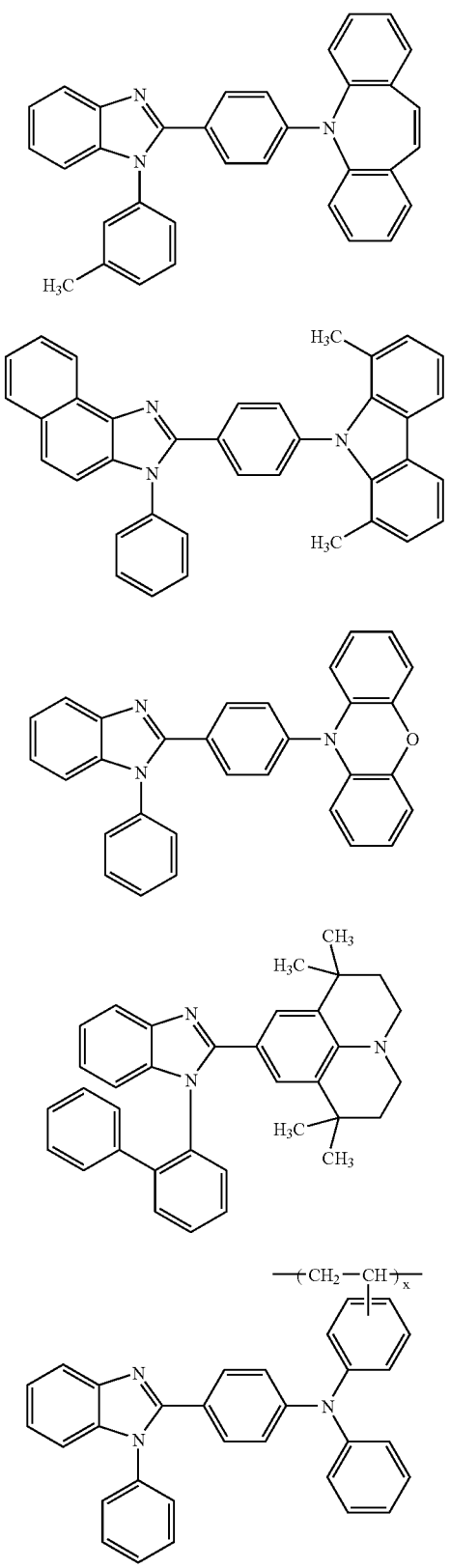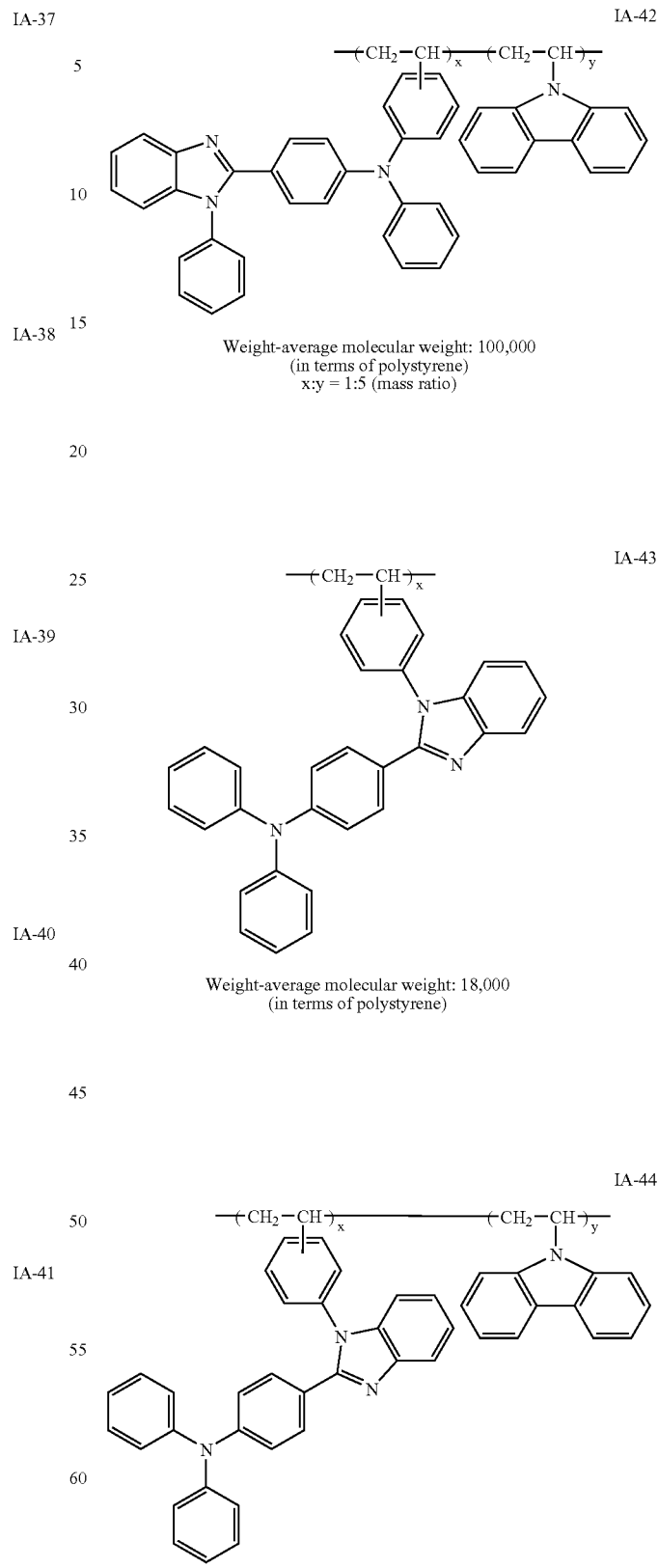

29
-continued

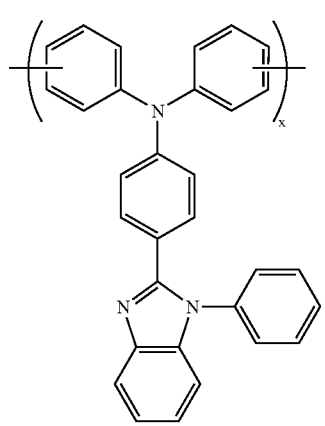

IA-45

Weight-average molecular weight: 18,000
(in terms of polystyrene)

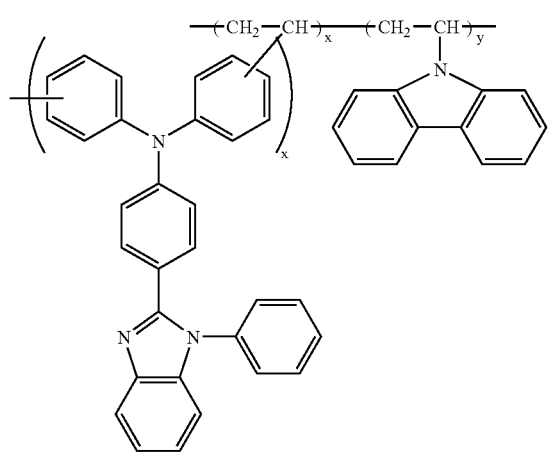

IA-46

Weight-average molecular weight: 20,000
(in terms of polystyrene)
x:y = 1:50 (mass ratio)

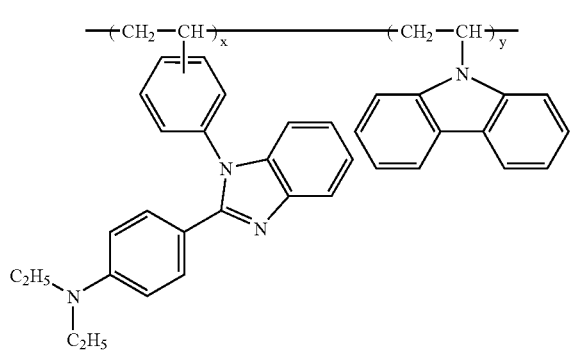

IA-47

Weight-average molecular weight: 100,000
(in terms of polystyrene)
x:y = 1:50 (mass ratio)

The above-mentioned compounds may be their tautomers.

Synthesis methods of the compounds of the invention represented by general formula (IA) are illustrated below, showing specific examples thereof.

30

SYNTHESIS EXAMPLE 1

Synthesis of Example Compound IA-1

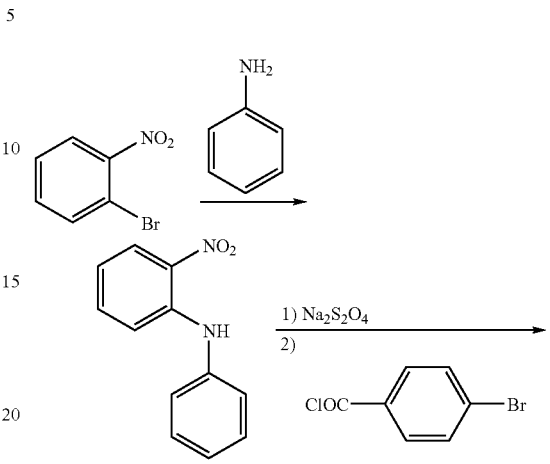

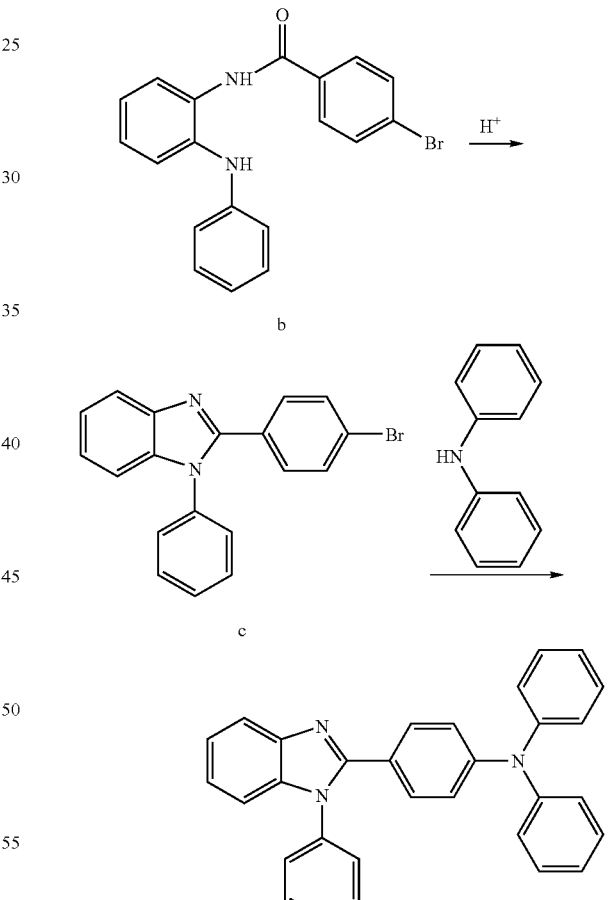

Example Compound IA-1

1-1. Synthesis of Compound a

Aniline (86.4 g (0.928 mol)) was added to 75.1 g (0.371 mol) of o-bromonitrobenzene, 205 g (1.48 mol) of potassium carbonate, 10.6 g (0.0557 mol) of copper(I) iodide and 450 ml of toluene with stirring at room temperature in an atmosphere of nitrogen. After heating under reflux for 5 hours, the reaction solution was filtered, and the filtrate was concentrated under reduced pressure. After purification by silica gel column chromatography (developing solvent: chloroform:hexane=1:1 (vol/vol)), recrystallization from chloroform/hexane was conducted to obtain 35.8 g (0.17 mol) of compound a. The yield was 45%.

1-2. Synthesis of Compound b

A solution of 100 g (0.560 mol) of sodium hydrosulfite in 280 ml of water was added dropwise to a solution of 24.0 g (0.112 mol) of compound a in 200 ml of tetrahydrofuran with stirring at room temperature in an atmosphere of nitrogen. Methanol (20 ml) was further added thereto, followed by stirring for 1 hour. Then, 200 ml of ethyl acetate was added, and a solution of 20 g (0.224 mol) of sodium hydrogencarbonate in 160 ml of water was added. A solution of 24.6 g (0.112 mol) of 4-bromobenzoyl chloride in 70 ml of ethyl acetate was further added dropwise, followed by stirring at room temperature for 3 hours. After extraction with ethyl acetate, the extract was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 34.0 g (0.092 mol) of compound b. The yield was 83%.

1-3. Synthesis of Compound c

Compound b (34 g (0.092 mol)) was dissolved in 500 ml of xylene, and 5 g (0.03 mol) of p-toluenesulfonic acid monohydrate was added thereto, followed by azeotropic dehydration with heating under reflux in an atmosphere of nitrogen for 5 hours. After the reaction solution was cooled to room temperature, the precipitated solid was collected by filtration, and recrystallized from ethanol/chloroform, thereby obtaining 27.8 g (0.080 mol) of compound c. The yield was 86%.

1-4. Synthesis of Example Compound IA-1

Diphenylamine (0.48 g (0.0029 mol)) was dissolved in 20 ml of xylene, and 0.33 g (0.0034 mol) of sodium methoxide and catalytic amounts of palladium (II) acetate (0.025 mol %) and tri-t-butylphosphine (0.1 mol %) were added thereto, followed by stirring. Then, 1.0 g (0.0029 mol) of compound c was added thereto, followed by heating under reflux for 3 hours. After the reaction solution was cooled to room temperature, the insoluble matter was removed by filtration, and the filtrate was extracted from ethyl acetate. The organic phase was washed with successive water and saturated brine, and dried on anhydrous magnesium sulfate. Then, the solvent was removed by distillation under reduced pressure. After purification by silica gel column chromatography (developing solvent: chloroform) recrystallization from chloroform/hexane was conducted to obtain 0.63 g (0.0014 mol) of example compound IA-1. The yield was 48%.

Then, the compounds of the invention represented by general formula (IB) will be described.

$R_1$ and $R_2$, which may the same or different, each represents a hydrogen atom, an aliphatic hydrocarbon group, an aryl group or a heterocyclic group. Further, $R_1$ and $R_2$, $R_1$ and L, and $R_2$ and L may each combine with each other to form a ring when possible.

The aliphatic hydrocarbon groups represented by $R_1$ and $R_2$ include a straight-chain, branched or cyclic alkyl group (having preferably from 1 to 30 carbon atoms, more preferably from 1 to 20 carbon atoms, and still more preferably from 1 to 12 carbon atoms, e.g., methyl, ethyl, iso-propyl, n-butyl, tert-butyl, n-octyl, n-decyl, n-hexadecyl, cyclopropyl, cyclopentyl or cyclohexyl), an alkenyl group (having preferably from 2 to 30 carbon atoms, more preferably from 2 to 20 carbon atoms, and still more preferably from 2 to 12 carbon atoms, e.g., vinyl, allyl, 2-butenyl or 3-pentenyl) and an alkynyl group (having preferably from 2 to 30 carbon atoms, more preferably from 2 to 20 carbon atoms, and still more preferably from 2 to 12 carbon atoms, e.g., propargyl or 3-pentynyl). Preferred are the alkyl group and the alkenyl group, and more preferred is methyl, ethyl, propyl, butyl, allyl or a condensed ring formed by bonding of $R_1$ and $R_2$ with L (e.g., a julolidine ring).

The aryl groups represented by $R_1$ and $R_2$ are preferably monocyclic to tetracyclic aryl groups each having from 6 to 30 carbon atoms (e.g., phenyl, naphthyl, anthryl, phenanthryl and pyrenyl). More preferred are phenyl having from 6 to 20 carbon atoms and naphthyl having from 10 to 24 carbon atoms, and still more preferred are phenyl having from 6 to 12 carbon atoms and naphthyl having from 10 to 16 carbon atoms.

The heterocyclic groups represented by $R_1$ and $R_2$ are 3- to 10-membered saturated or unsaturated heterocyclic groups each having at least one of N, O and S atoms. They may be monocyclic or may form condensed rings with other rings.

The heterocyclic groups are preferably 3- to 10-membered aromatic heterocyclic groups each having at least one of nitrogen, oxygen, sulfur and selenium atoms, more preferably 5- or 6-membered aromatic heterocyclic groups, and still more preferably 5- or 6-membered aromatic heterocyclic groups each having an N atom or an S atom.

Examples of the heterocyclic groups include pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzthiazole, benzotriazole, tetraazaindene, carbazole, azepine, dibenzoazepine and tribenzoazepine. Preferred are thiophene, triazole, oxazole, pyridine, triazine and quinoline, more preferred are thiophene, pyridine, triazine and quinoline, and still more preferred is thiophene.

The aliphatic hydrocarbon groups, aryl groups and heterocyclic groups represented by $R_1$ and $R_2$ may have substituents. Examples of the substituents include an alkyl group (having preferably from 1 to 20 carbon atoms, more preferably from 1 to 12 carbon atoms, and particularly preferably from 1 to 8 carbon atoms, e.g. methyl, ethyl, iso-propyl, tert-butyl, n-octyl, n-decyl, n-hexadecyl, cyclopropyl, cyclopentyl or cyclohexyl), an alkenyl group (having preferably from 2 to 20 carbon atoms, more preferably from 2 to 12 carbon atoms, and particularly preferably from 2 to 8 carbon atoms, e.g., vinyl, allyl, 2-butenyl or 3-pentenyl), an alkynyl group (having preferably from 2 to 20 carbon atoms, more preferably from 2 to 12 carbon atoms, and particularly preferably from 2 to 8 carbon atoms, e.g., propargyl or 3-pentynyl), an aryl group (having preferably from 6 to 30 carbon atoms, more preferably from 6 to 20 carbon atoms, and particularly preferably from 6 to 12 carbon atoms, e.g., phenyl, p-methylphenyl or naphthyl), an amino group (having preferably from 0 to 20 carbon atoms, more preferably from 0 to 12 carbon atoms, and particularly preferably from 0 to 6 carbon atoms, e.g., amino, methylamino, dimethylamino, diethylamino, diphenylamino or dibenzylamino), an alkoxyl group (having preferably from 1 to 20 carbon atoms, more preferably from 1 to 12 carbon atoms, and particularly preferably from 1 to 8 carbon atoms, e.g., methoxy, ethoxy or butoxy), an aryloxy group (having preferably from 6 to 20 carbon atoms, more preferably from 6 to 16 carbon atoms, and particularly preferably from 6 to 12 carbon atoms, e.g., phenyloxy or 2-naphtyloxy), an acyl group (having preferably from 1 to 20 carbon atoms, more preferably from 1 to 16 carbon atoms, and particularly preferably from 1 to 12 carbon atoms, e.g., acetyl, benzoyl, formyl or pivaloyl), an alkoxycarbonyl groups (having preferably from 2 to 20 carbon atoms, more preferably from 2 to 16 carbon atoms, and particularly preferably from 2 to 12 carbon atoms, e.g., methoxycarbonyl or ethoxycarbonyl), an aryloxycarbonyl group (having preferably from 7 to 20 carbon atoms, more preferably from 7 to 16 carbon atoms, and particularly preferably from 7 to 10 carbon atoms, e.g., phenyloxycarbonyl), an acyloxy group (having preferably from 2 to 20 carbon atoms, more preferably from 2 to 16 carbon atoms, and particularly preferably from 2 to 10 carbon atoms, e.g., acetoxy or benzoyloxy), an acylamino group (having preferably from 2 to 20 carbon atoms, more preferably from 2 to 16 carbon atoms, and particularly preferably from 2 to 10 carbon atoms, e.g., acetylamio or benzoylamino), an alkoxycarbonylamino group (having preferably from 2 to 20 carbon atoms, more preferably from 2 to 16 carbon atoms, and particularly preferably from 2 to 12 carbon atoms, e.g., methoxy-carbonylamino), an aryloxycarbonylamino group (having preferably from 7 to 20 carbon atoms, more preferably from 7 to 16 carbon atoms, and particularly preferably from 7 to 12 carbon atoms, e.g., phenyloxycarbonylamino), a sulfonylamino group (having preferably from 1 to 20 carbon atoms, more preferably from 1 to 16 carbon atoms, and particularly preferably from 1 to 12 carbon atoms, e.g., methanesulfonylamino or benzenesulfonylamino), a sulfamoyl group (having preferably from 0 to 20 carbon atoms, more preferably from 0 to 16 carbon atoms, and particularly preferably from 0 to 12 carbon atoms, e.g., sulfamoyl, methylsulfamoyl, dimethylsulfamoyl or phenylsulfamoyl), a carbamoyl group (having preferably from 1 to 20 carbon atoms, more preferably from 1 to 16 carbon atoms, and particularly preferably from 1 to 12 carbon atoms, e.g., carbamoyl, methylcarbamoyl, diethylcarbamoyl or phenylcarbamoyl), an alkylthio group (having preferably from 1 to 20 carbon atoms, more preferably from 1 to 16 carbon atoms, and particularly preferably from 1 to 12 carbon atoms, e.g., methylthio or ethylthio), an arylthio group (having preferably from 6 to 20 carbon atoms, more preferably from 6 to 16 carbon atoms, and particularly preferably from 6 to 12 carbon atoms, e.g., phenylthio), a sulfonyl group (having preferably from 1 to 20 carbon atoms, more preferably from 1 to 16 carbon atoms, and particularly preferably from 1 to 12 carbon atoms, e.g., mesyl or tosyl), a sulfinyl group (having preferably from 1 to 20 carbon atoms, more preferably from 1 to 16 carbon atoms, and particularly preferably from 1 to 12 carbon atoms, e.g., methanesulfinyl or benzenesulfinyl), a ureido group (having preferably from 1 to 20 carbon atoms, more preferably from 1 to 16 carbon atoms, and particularly preferably from 1 to 12 carbon atoms, e.g., ureido, methylureido or phenylureido), a phosphoric acid amide group (having preferably from 1 to 20 carbon atoms, more preferably from 1 to 16 carbon atoms, and particularly preferably from 1 to 12 carbon atoms, e.g., diethylphosphoric acid amide or phenylphosphoric acid amide), a hydroxyl group, a mercapto group, a halogen atom (e.g., fluorine, chlorine, bromine or iodine), a cyano group, a sulfo group, a carboxyl group, a nitro group, a hydroxamic acid group, a sulfino group, a hydrazine group, an imino group, a heterocyclic group (having preferably from 1 to 30 carbon atoms, and more preferably from 1 to 12 carbon atoms, having a heteroatom, e.g., nitrogen, oxygen or sulfur, and specifically including imidazolyl, pyridyl, quinolyl, furyl, thienyl, piperidyl, morpholino, benzoxazolyl, benzimidazolyl, benzthiazolyl or carbazolyl), and a silyl group (having preferably from 3 to 40 carbon atoms, more preferably from 3 to 30 carbon atoms, and particularly preferably from 3 to 24 carbon atoms, e.g., trimethylsilyl or triphenylsilyl). These substituents may be further substituted. When there are two or more substituents, they may be the same or different. Further, they may combine with each other to form a ring when possible.

$R_1$ and $R_2$ are each preferably a hydrogen atom, an alkyl group, an aryl group and an aromatic heterocyclic group. When the compounds are used as charge transfer materials and concurrently light emitting materials (non-dope type), $R_1$ and $R_2$ are each preferably an aryl group and an aromatic heterocyclic group, and more preferably an aryl group (preferably a monocyclic or bicyclic aryl group having from 6 to 30 carbon atoms, more preferably phenyl having from 6 to 20 carbon atoms, and still more preferably phenyl having from 6 to 20 carbon atoms). When the compounds are used as dope type light emitting materials, $R_1$ and $R_2$ are each preferably a hydrogen atom, an alkyl group or an alkylene group combining with L to form a ring, more preferably an alkyl group or an alkylene group combining with L to form a ring, and still more preferably an alkyl group having from 1 to 8 carbon toms or an alkylene group combining with L to form a 6-membered ring. Particularly preferred are methyl, ethyl and the alkylene group combining with L to form a 6-membered ring (e.g., trimethylene and 3,3-dimethyltrimethylene).

X represents O, S, Se, Te or N—R. R represents a hydrogen atom, an aliphatic hydrocarbon group, an aryl group or a heterocyclic group.

Preferred examples of the aliphatic hydrocarbon groups represented by R include an alkyl group (having preferably from 1 to 20 carbon atoms, more preferably from 1 to 12 carbon atoms, and particularly preferably from 1 to 8 carbon atoms, e.g., methyl, ethyl, iso-propyl, tert-butyl, n-octyl, n-decyl, n-hexadecyl, cyclopropyl, cyclopentyl or cyclohexyl), an alkenyl group (having preferably from 2 to 20 carbon atoms, more preferably from 2 to 12 carbon atoms, and particularly preferably from 2 to 8 carbon atoms, e.g., vinyl, allyl, 2-butenyl or 3-pentenyl) and an alkynyl group (having preferably from 2 to 20 carbon atoms, more preferably from 2 to 12 carbon atoms, and particularly preferably from 2 to 8 carbon atoms, such as propargyl or 3-pentynyl). More preferred is the alkyl group.

The aryl group represented by R has preferably 6 to 30 carbon atoms, more preferably 6 to 20 carbon atoms, and particularly preferably 6 to 12 carbon atoms. Examples thereof include phenyl, 2-methylphenyl, 3-methylphenyl, 4-methylphenyl, 4-methoxyphenyl, 3-trifluoromethylphenyl, 2-phenylphenyl, pentafluorophenyl, 1-naphthyl and 2-naphthyl, and preferred are phenyl, 2-methylphenyl and 2-phenylphenyl.

The heterocyclic group represented by R is a monocyclic or condensed heterocyclic group (a heterocyclic group having from 1 to 20 carbon atoms, more preferably from 1 to 12 carbon atoms, and still more preferably from 2 to 10 carbon atoms), and preferably an aromatic heterocyclic group containing at least one of nitrogen, oxygen, sulfur and selenium atoms. Specific examples of the heterocyclic group represented by R include pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzthiazole, benzotriazole, tetraazaindene and carbazole. Preferred are furan, thiophene, pyridine, pyrazine, pyrimidine, pyridazine, triazine, quinoline, phthalazine, naphthyridine, quinoxaline, and quinazoline, and more preferred are furan, thiophene, pyridine and quinoline.

The aliphatic hydrocarbon groups, aryl groups and heterocyclic groups group represented by R may have substituents. As the substituents, the substituents described above for the groups represented by $R_1$ and $R_2$ in general formula (IB) can be applied, and preferred substituents are also the same as given therefor.

R is preferably an alkyl group, an aryl group or an aromatic heterocyclic group, more preferably an aryl group or an aromatic heterocyclic group, and still more preferably an aryl group.

X is preferably O, S or N—R, more preferably O or N—R, still more preferably N—R, and particularly preferably N—Ar, wherein Ar represents an aryl group, which has preferably from 6 to 30 carbon atoms, more preferably from 6 to 20 carbon atoms, and particularly preferably from 6 to 12 carbon atoms.

L represents a connecting group. The connecting group represented by L is preferably a connecting group formed by a single bond, C, N, O, S, Se, Te, Si or Ge, more preferably a group comprising a single bond, alkylene, alkenylene, alkynylene, arylene, a divalent heterocycle (preferably an aromatic heterocycle, and more preferably an aromatic heterocycle formed by an azole, thiophene or furan ring) or a combination thereof with N, and still more preferably a group comprising arylene, a divalent aromatic heterocycle or a combination thereof with N.

Specific examples of the connecting groups represented by L include the following groups as well as a single bond.

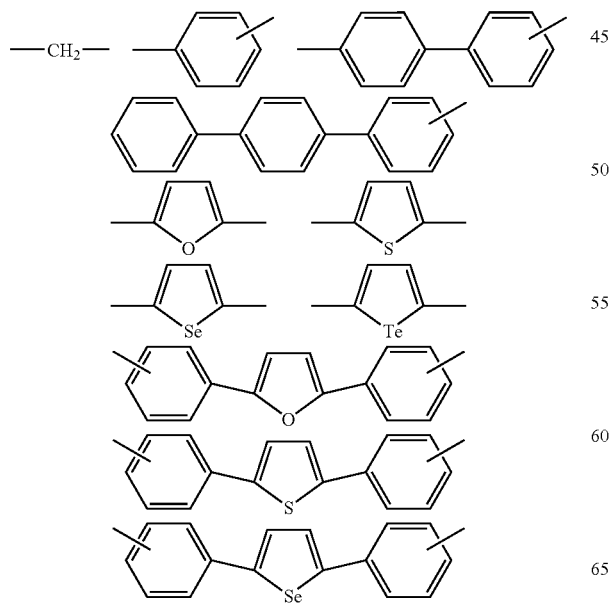

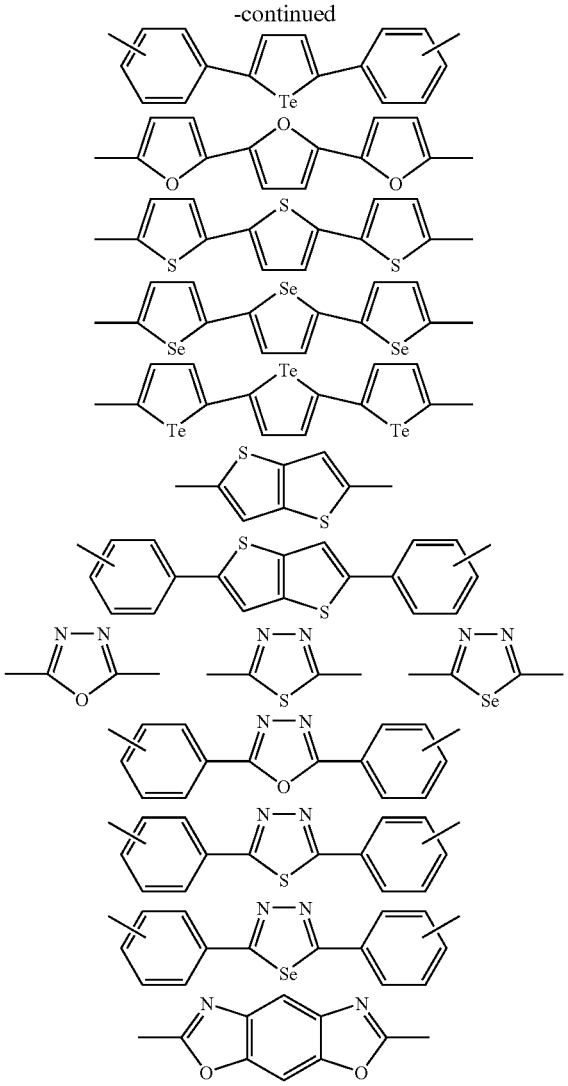

-continued

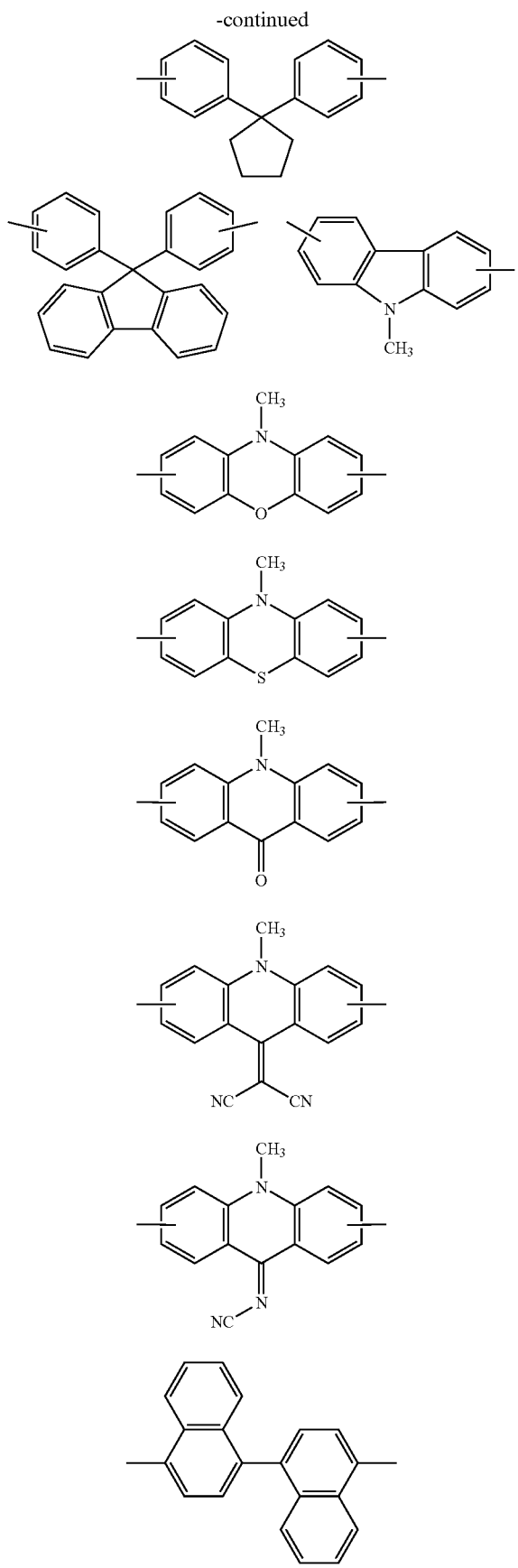

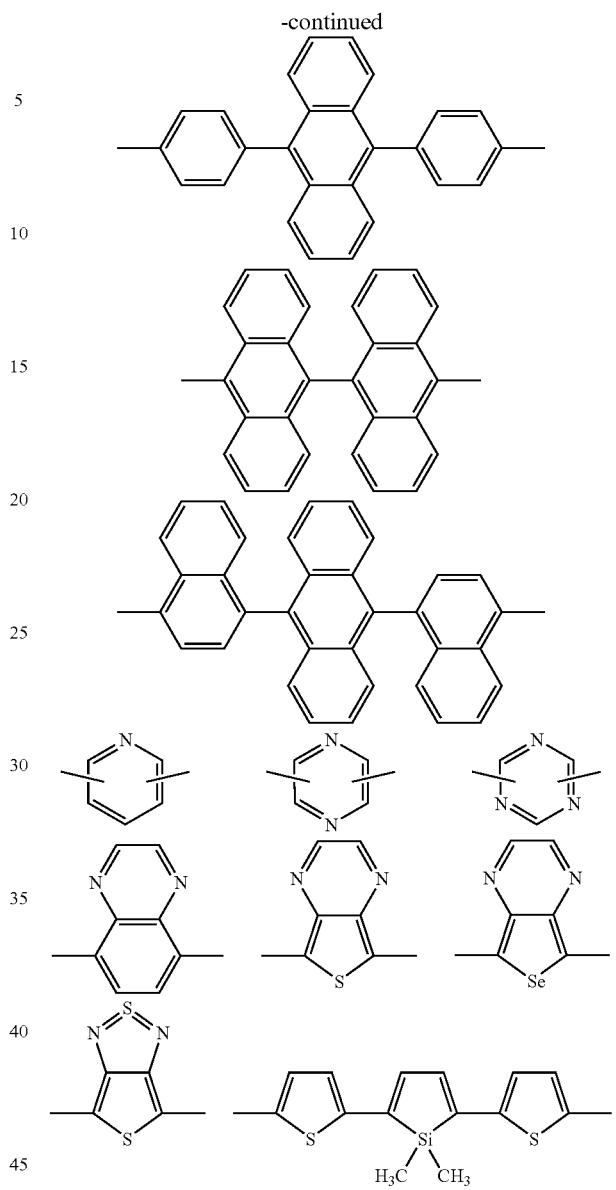

The connecting groups represented by L may have substituents. As the substituents, for example, the substituents described above for the groups represented by $R_1$ and $R_2$ can be applied. Preferred examples of the substituents for L include an alkyl group, an alkenyl group, an alkynyl group, an aryl group, an alkoxyl group, an aryloxy group, an acyl group, a halogen atom, a cyano group, a heterocyclic group and a silyl group. More preferred are an alkyl group, an alkenyl group, an alkynyl group, an aryl group, an alkoxyl group, an aryloxy group, a halogen atom, a cyano group and an aromatic heterocyclic group, and still more preferred are an alkyl group, an aryl group and an aromatic heterocyclic group.

$Z_1$ represents an atomic group necessary to form a heterocycle. The heterocycles formed by $Z_1$ are preferably aromatic heterocycles, more preferably nitrogen-containing aromatic heterocycles, and particularly preferably 6-membered nitrogen-containing aromatic heterocycles.

Examples of the heterocycles formed by $Z_1$ include a pyrazoline ring, a pyrrole ring, a furan ring, a thiophene ring, a selenophene ring, a tellurophene ring, an imidazoline ring, an imidazole ring, a thiazole ring, an isothiazole ring, an oxazoline ring, an oxazole ring, an isoxazole ring, a selenazole ring, a thiadiazole ring, an oxadiazole ring, a selenadiazole ring, a pyridine ring, a pyrazole ring, a pyrazine ring, a pyrimidine ring, a pyridazine ring, a triazine ring, a dithiin ring and a dihydrodithiin ring. Preferred are a pyridine ring, a pyrazine ring, a pyrimidine ring and a pyridazine ring, more preferred are a pyridine ring and a pyrazine ring, and still more preferred is a pyridine ring.

The heterocycles formed by $Z_1$ may further form condensed rings with other rings, and may also have substituents. As the substituents, for example, the substituents described above for the groups represented by $R_1$ and $R_2$ can be applied. Preferred examples of the substituents for $Z_1$ include an alkyl group, an alkenyl group, an alkynyl group, an aryl group, an amino group, an alkoxyl group, an aryloxy group, an acyl group, a alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group and a heterocyclic group. More preferred are an alkyl group, an alkenyl group, an aryl group, an alkoxyl group, an aryloxy group, a halogen atom, a cyano group and a heterocyclic group, still more preferred are an alkyl group, an aryl group, an alkoxyl group, an aryloxy group and an aromatic heterocyclic group, and particularly preferred are an alkyl group, an aryl group, an alkoxyl group and an aromatic heterocyclic group.

Of the compounds represented by general formula (IB), preferred is the compound represented by the following general formula (IIB):

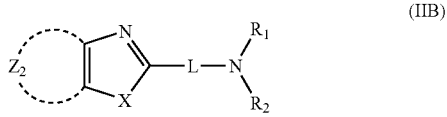

(IIB)

wherein $R_1$, $R_2$, X and L each has the same meaning as given for general formula (IB), and each preferred range is also the same as given therefor. $Z_2$ represents an atomic group necessary to form an aromatic heterocycle.

The aromatic heterocycles formed by $Z_2$ are preferably nitrogen-containing aromatic heterocycles, and more preferably 6-membered nitrogen-containing aromatic heterocycles. Examples of the aromatic heterocycles formed by $Z_2$ include a pyrrole ring, a furan ring, a thiophene ring, a selenophene ring, a tellurophene ring, an imidazole ring, a thiazole ring, an isothiazole ring, an oxazole ring, an isoxazole ring, a selenazole ring, a thiadiazole ring, an oxadiazole ring, a selenadiazole ring, a pyridine ring, a pyrazole ring, a pyrazine ring, a pyrimidine ring, a pyridazine ring and a triazine ring. More preferred are a pyridine ring, a pyrazine ring, a pyrimidine ring and a pyridazine ring, still more preferred are a pyridine ring and a pyrazine ring, and yet still more preferred is a pyridine ring.

The aromatic heterocycles formed by $Z_2$ may further form condensed rings with other rings, and may also have substituents. As the substituents, for example, the substituents described above for the groups represented by $R_1$ and $R_2$ in general formula (IB) can be applied, and a preferred range is also the same as given for the substituents for $Z_1$ in general formula (IB).

Of the compounds represented by general formula (IB), more preferred is the compound represented by the following general formula (III):

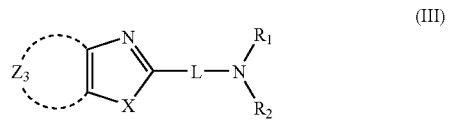

(III)

wherein $R_1$, $R_2$, X and L each has the same meaning as given for general formula (IB), and each preferred range is also the same as given therefor. $Z_3$ represents an atomic group necessary to form a nitrogen-containing aromatic heterocycle.

The nitrogen-containing aromatic heterocycles formed by $Z_3$ are preferably 6-membered nitrogen-containing aromatic heterocycles. Examples of the nitrogen-containing aromatic heterocycles formed by $Z_3$ include a pyrrole ring, an imidazole ring, a thiazole ring, an isothiazole ring, an oxazole ring, an isoxazole ring, a selenazole ring, a thiadiazole ring, an oxadiazole ring, a selenadiazole ring, a pyridine ring, a pyrazole ring, a pyrazine ring, a pyrimidine ring, a pyridazine ring and a triazine ring. More preferred are a pyridine ring, a pyrazine ring, a pyrimidine ring and a pyridazine ring, still more preferred are a pyridine ring and a pyrazine ring, and yet still more preferred is a pyridine ring.

The aromatic heterocycles formed by $Z_3$ may further form condensed rings with other rings, and may also have substituents. As the substituents, for example, the substituents described above for the groups represented by $R_1$ and $R_2$ in general formula (IB) can be applied, and a preferred range is also the same as given for the substituents for $Z_1$ in general formula (IB).

Of the compounds represented by general formula (IB), still more preferred is the compound represented by the following general formula (IV):

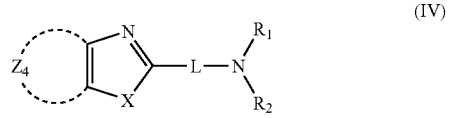

(IV)

wherein $R_1$, $R_2$, X and L each has the same meaning as given for general formula (IB), and each preferred range is also the same as given therefor. $Z_4$ represents an atomic group necessary to form a 6-membered nitrogen-containing aromatic heterocycle.

Examples of the 6-membered nitrogen-containing aromatic heterocycles formed by $Z_4$ include a pyridine ring, a pyrazine ring, a pyrimidine ring, a pyridazine ring and a triazine ring. More preferred are a pyridine ring, a pyrazine ring, a pyrimidine ring and a pyridazine ring, still more preferred are a pyridine ring and a pyrazine ring, and yet still more preferred is a pyridine ring.

The aromatic heterocycles formed by $Z_4$ may further form condensed rings with other rings, and may also have substituents. As the substituents, for example, the substituents described above for the groups represented by $R_1$ and $R_2$ in general formula (IB) can be applied, and a preferred range is also the same as given for the substituents for $Z_1$ in general formula (IB).

Of the compounds represented by general formula (IB), yet still more preferred is the compound represented by the following general formula (V):

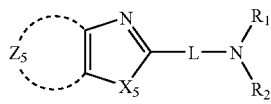

(V)

wherein $R_1$, $R_2$ and L each has the same meaning as given for general formula (IB), and each preferred range is also the same as given therefor. $X_5$ represents O, S or N—R. R has the same meaning as given for general formula (IB), and a preferred range is also the same as given therefor. $Z_5$ has the same meaning as $Z_4$ in general formula (IV), and a preferred range is also the same as given therefor.

Of the compounds represented by general formula (IB), more preferred is the compound represented by the following general formula (VI):

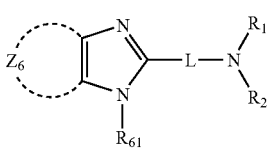

(VI)

wherein $R_1$, $R_2$ and L each has the same meaning as given for general formula (IB), and each preferred range is also the same as given therefor. $R_{61}$ has the same meaning as R in general formula (IB), and a preferred range is also the same as given therefor. $Z_6$ has the same meaning as $Z_4$ in general formula (IV), and a preferred range is also the same as given therefor.

Of the compounds represented by general formula (IB), still more preferred is the compound represented by the following general formula (VII):

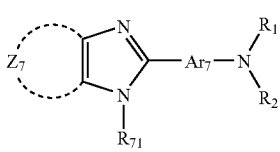

(VII)

wherein $R_1$ and $R_2$ each has the same meaning as given for general formula (IB), and each preferred range is also the same as given therefor. $Z_7$ has the same meaning as $Z_4$ in general formula (IV), and a preferred range is also the same as given therefor. $R_{71}$ has the same meaning as R in general formula (IB), and a preferred range is also the same as given therefor. $Ar_7$ represents arylene or a divalent aromatic heterocyclic group. Arylene or the divalent aromatic heterocyclic group represented by $Ar_7$ may have a substituent. As the substituents, the substituents described above for the groups represented by $R_1$ and $R_2$ can be applied. Preferred examples of the substituents for $Ar_7$ include an alkyl group, an alkenyl group, an alkynyl group, an aryl group, an alkoxyl group, an aryloxy group, an acyl group, a halogen atom, a cyano group, a heterocyclic group and a silyl group. More preferred are an alkyl group, an alkenyl group, an alkynyl group, an aryl group, an alkoxyl group, an aryloxy group, a halogen atom, a cyano group and an aromatic heterocyclic group, still more preferred are an alkyl group, an aryl group and an aromatic heterocyclic group.

Of the compounds represented by general formula (IB), yet still more preferred is the compound represented by the following general formula (VIII):

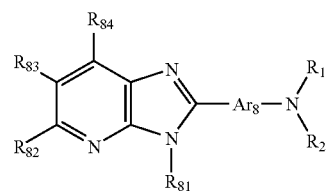

(VIII)

wherein $R_1$ and $R_2$ each has the same meaning as given for general formula (IB), and each preferred range is also the same as given therefor. $R_{81}$ has the same meaning as R in general formula (IB), and a preferred range is also the same as given therefor. $R_{82}$, $R_{83}$ and $R_{84}$ each represents a hydrogen atom or a substituent. As the substituents, the substituents described above for the groups represented by $R_1$ and $R_2$ in general formula (IB) can be applied. Preferred examples of $R_{82}$, $R_{83}$ and $R_{84}$ include a hydrogen atom, an alkyl group, an alkenyl group, an alkynyl group, an aryl group, an alkoxyl group, an aryloxy group, an acyl group, a halogen atom, a cyano group, a heterocyclic group, and a silyl group. More preferred are a hydrogen atom, an alkyl group, an alkenyl group, an alkynyl group, an aryl group, an alkoxyl group, an aryloxy group, a halogen atom, a cyano group and an aromatic heterocyclic group, still more preferred are a hydrogen atom, an alkyl group, an aryl group and an aromatic heterocyclic group, and particularly preferred is a hydrogen atom. Further, the substituents may combine with each other to form a ring when possible. $Ar_8$ has the same meaning as $Ar_7$ in general formula (VII), and a preferred range is also the same as given therefore.

Of the compounds represented by general formula (IB), most preferred are the compounds represented by the following general formulas (IX), (X) and (XI):

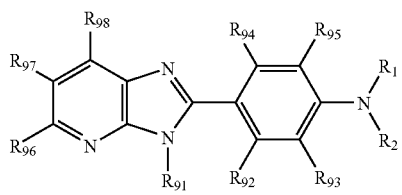

(IX)

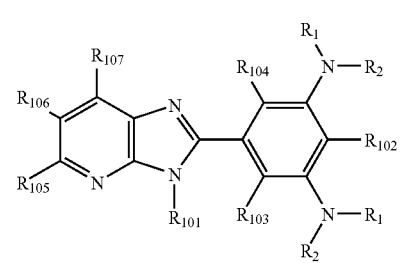

(X)

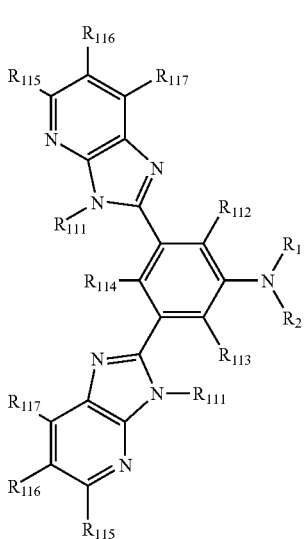
(XI)

In general formula (IX), $R_1$ and $R_2$ each has the same meaning as given for general formula (IB), and each preferred range is also the same as given therefor. $R_{91}$ has the same meaning as R in general formula (IB), and a preferred range is also the same as given therefor. $R_{92}$, $R_{93}$, $R_{94}$, $R_{95}$, $R_{96}$, $R_{97}$ and $R_{98}$ each represents a hydrogen atom or a substituent. As the substituents, the substituents described above for the groups represented by $R_1$ and $R_2$ in general formula (IB) can be applied. Preferred examples of $R_{92}$, $R_{93}$, $R_{94}$, $R_{95}$, $R_{96}$, $R_{97}$ and $R_{98}$ include a hydrogen atom, an alkyl group, an alkenyl group, an alkynyl group, an aryl group, an alkoxyl group, an aryloxy group, an acyl group, a halogen atom, a cyano group, a heterocyclic group and a silyl group. More preferred are a hydrogen atom, an alkyl group, an alkenyl group, an alkynyl group, an aryl group, an alkoxyl group, an aryloxy group, a halogen atom, a cyano group and an aromatic heterocyclic group, still more preferred are a hydrogen atom, an alkyl group, an aryl group and an aromatic heterocyclic group, and particularly preferred is a hydrogen atom. Further, the substituents may combine with each other to form a ring when possible.

In general formula (X), $R_1$ and $R_2$ each has the same meaning as given for general formula (IB), and each preferred range is also the same as given therefor. $R_{101}$ has the same meaning as R in general formula (IB), and a preferred range is also the same as given therefor. $R_{102}$, $R_{103}$, $R_{104}$, $R_{105}$, $R_{106}$ and $R_{107}$ each represents a hydrogen atom or a substituent. As the substituents, the substituents described above for the groups represented by $R_1$ and $R_2$ in general formula (IB) can be applied. Preferred examples of $R_{102}$, $R_{103}$, $R_{104}$, $R_{105}$, $R_{106}$ and $R_{107}$ include a hydrogen atom, an alkyl group, an alkenyl group, an alkynyl group, an aryl group, an alkoxyl group, an aryloxy group, an acyl group, a halogen atom, a cyano group, a heterocyclic group and a silyl group. More preferred are a hydrogen atom, an alkyl group, an alkenyl group, an alkynyl group, an aryl group, an alkoxyl group, an aryloxy group, a halogen atom, a cyano group and an aromatic heterocyclic group, still more preferred are a hydrogen atom, an alkyl group, an aryl group and an aromatic heterocyclic group, and particularly preferred is a hydrogen atom. Further, the substituents may combine with each other to form a ring when possible.

In general formula (XI), $R_1$ and $R_2$ each has the same meaning as given for general formula (IB), and each preferred range is also the same as given therefor. $R_{111}$ has the same meaning as R in general formula (IB), and a preferred range is also the same as given therefor. $R_{112}$, $R_{113}$, $R_{114}$, $R_{115}$, $R_{116}$ and $R_{117}$ each represents a hydrogen atom or a substituent. As the substituents, the substituents described above for the groups represented by $R_1$ and $R_2$ in general formula (IB) can be applied. Preferred examples of $R_{112}$, $R_{113}$, $R_{114}$, $R_{115}$, $R_{116}$ and $R_{117}$ include a hydrogen atom, an alkyl group, an alkenyl group, an alkynyl group, an aryl group, an alkoxyl group, an aryloxy group, an acyl group, a halogen atom, a cyano group, a heterocyclic group and a silyl group. More preferred are a hydrogen atom, an alkyl group, an alkenyl group, an alkynyl group, an aryl group, an alkoxyl group, an aryloxy group, a halogen atom, a cyano group and an aromatic heterocyclic group, still more preferred are a hydrogen atom, an alkyl group, an aryl group and an aromatic heterocyclic group, and particularly preferred is a hydrogen atom. Further, the substituents may combine with each other to form a ring when possible.

The compounds represented by general formulas (IB) (IIB) and (III) to (XI) may be either low molecular weight compounds, or high molecular weight compounds in which residues are connected to main chains of polymers (the weight-average molecular weight of the compounds is preferably from 1,000 to 5,000,000, more preferably from 5,000 to 2,000,000, and still more preferably from 10,000 to 1,000,000) or high molecular weight compounds having the compounds of the invention as main chains (the weight-average molecular weight of the compounds is preferably from 1,000 to 5,000,000, more preferably from 5,000 to 2,000,000, and still more preferably from 10,000 to 1,000,000). In the case of the high molecular weight compounds, they may be either homopolymers or copolymers with other polymers. In the case of the copolymers, they may be either random copolymers or block copolymers.

Specific examples of the compounds of the invention represented by general formula (IB) are shown below, but it is to be understood that the invention is not limited thereto.

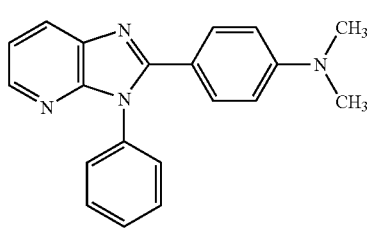

IB-1

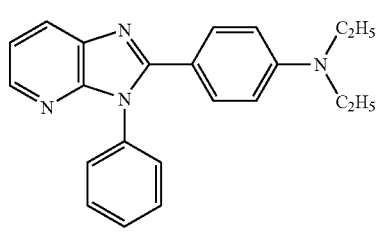

IB-2

-continued
IB-3
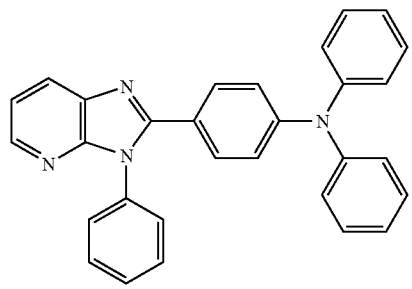
IB-4
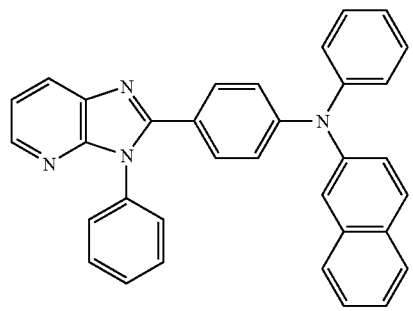
IB-5
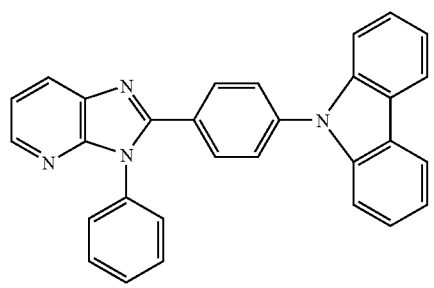
IB-6
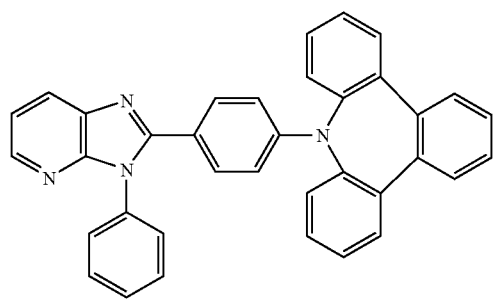
IB-7
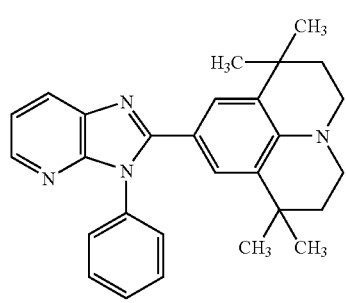
IB-8
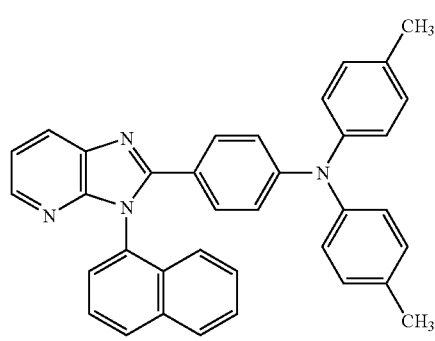
IB-9
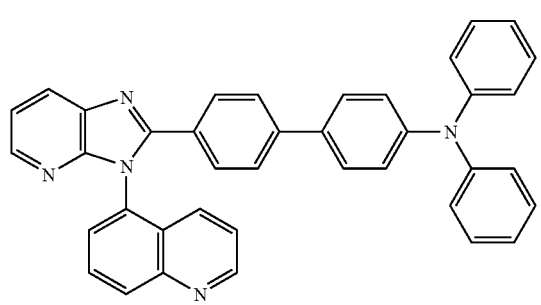
IB-10
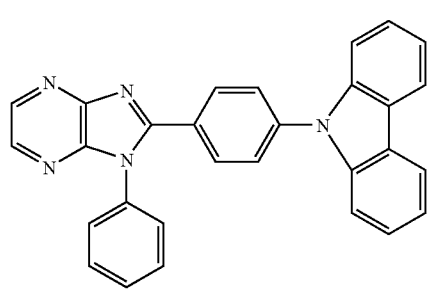
IB-11
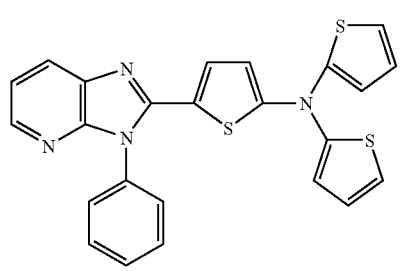
IB-12
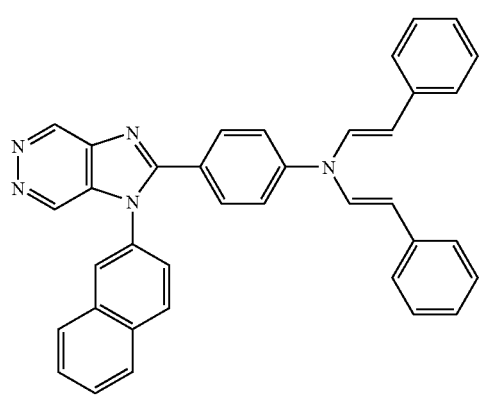

-continued
IB-13
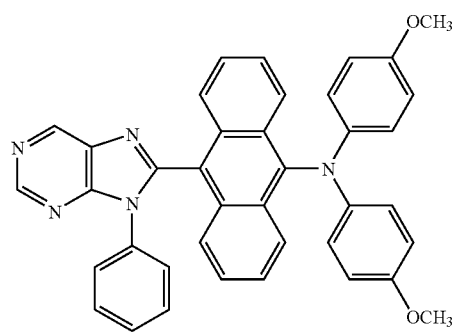
IB-14
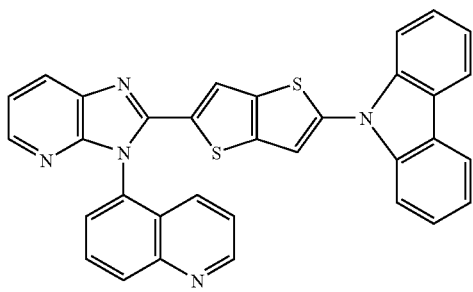
IB-15
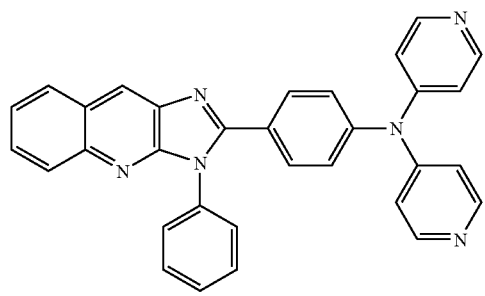
IB-16
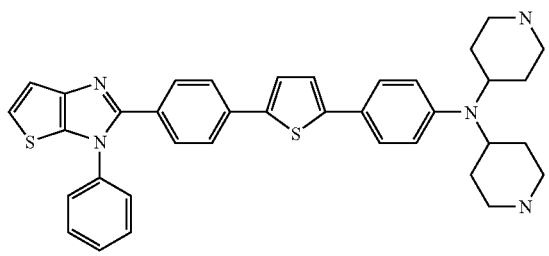
IB-17
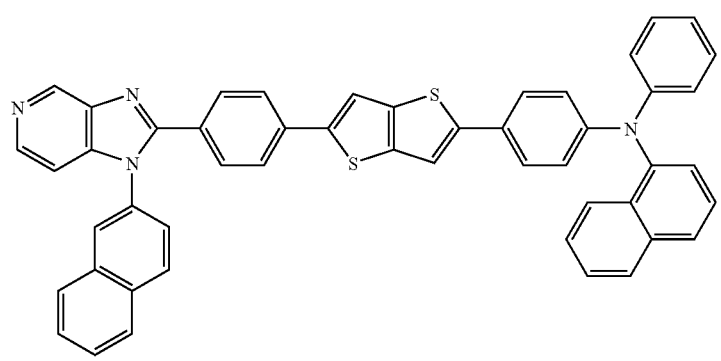
IB-18
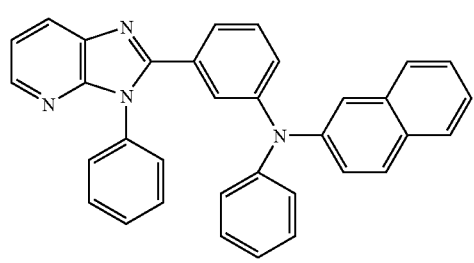
IB-19
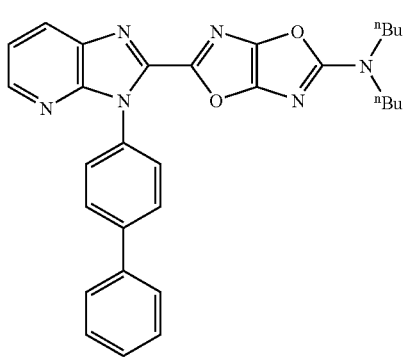
IB-20
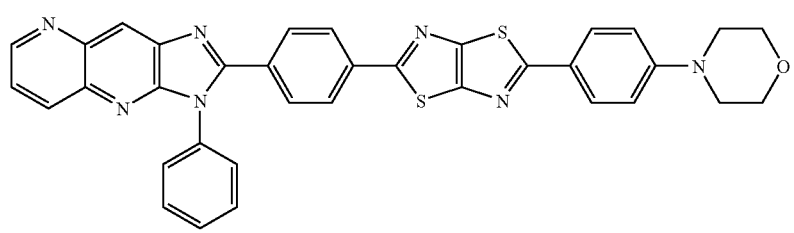

-continued
IB-21
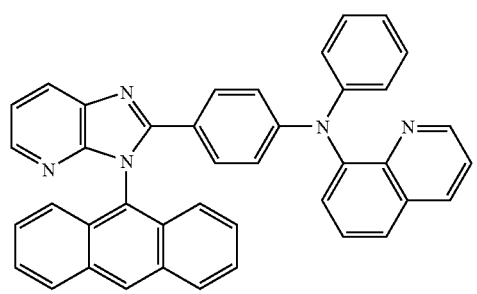
IB-22
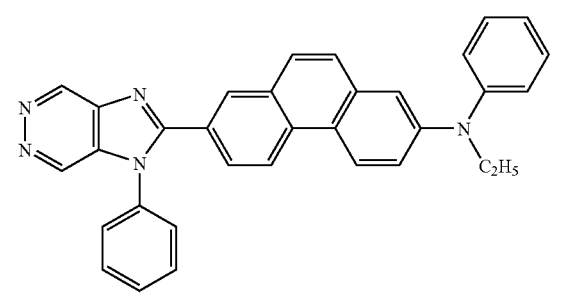
IB-23
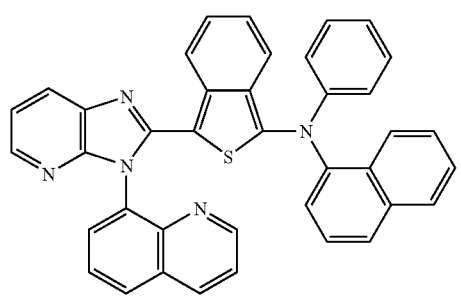
IB-24
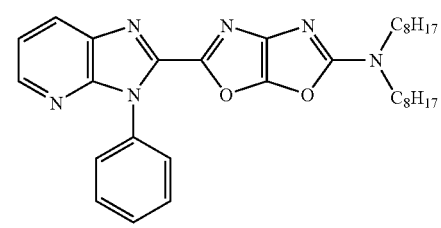
IB-25
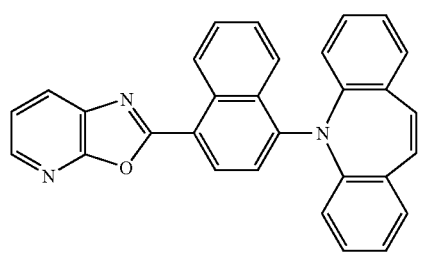
IB-26
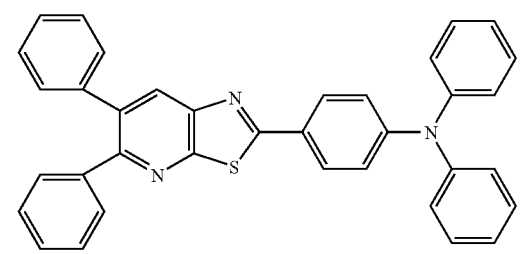
IB-27
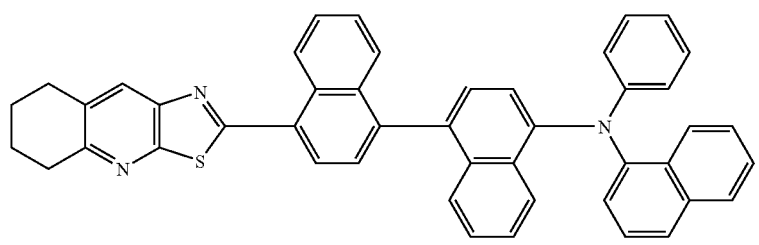
IB-28
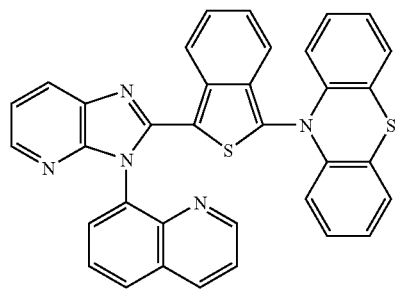
IB-29
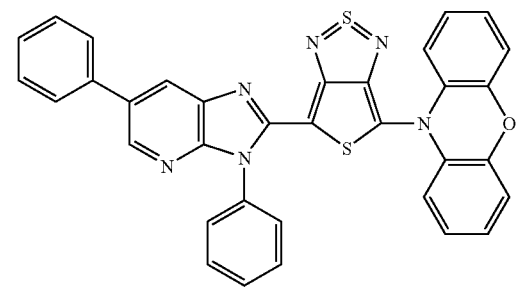

-continued
IB-30
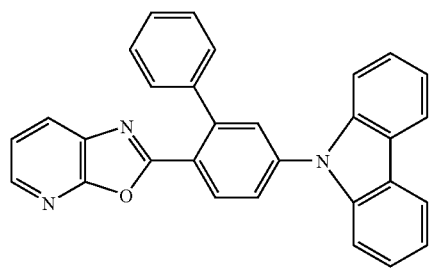
IB-31
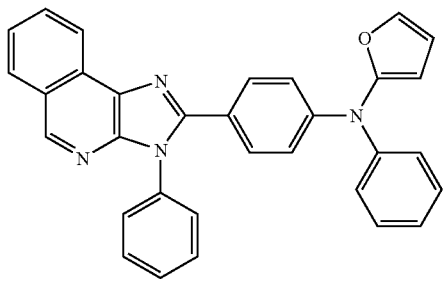
IB-32
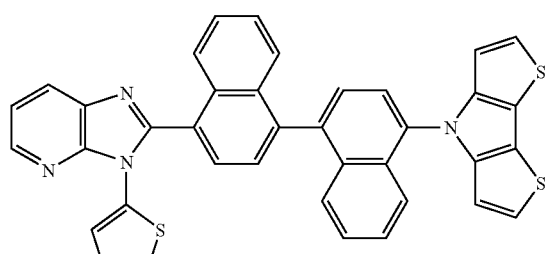
IB-33
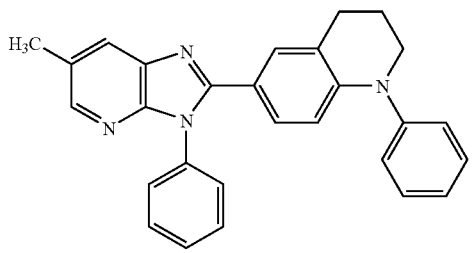
IB-34
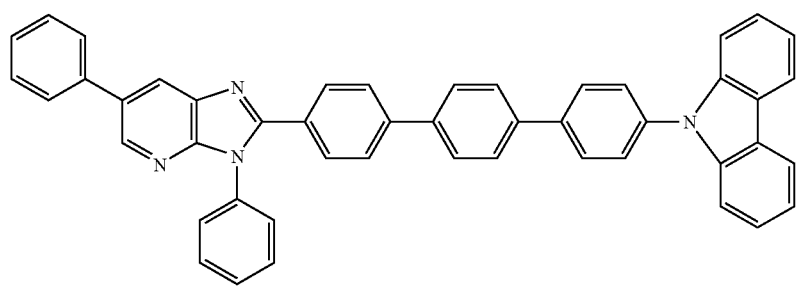
IB-35
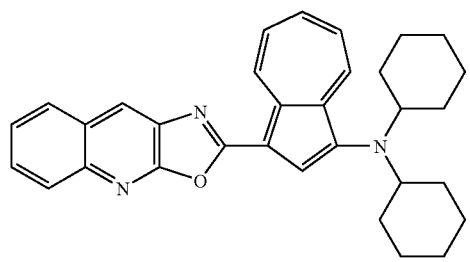
IB-36
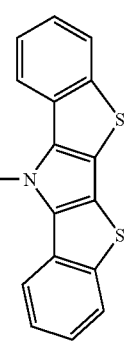
IB-37
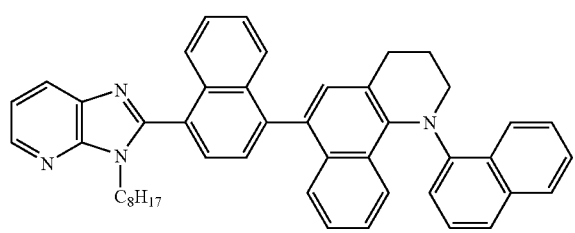
IB-38
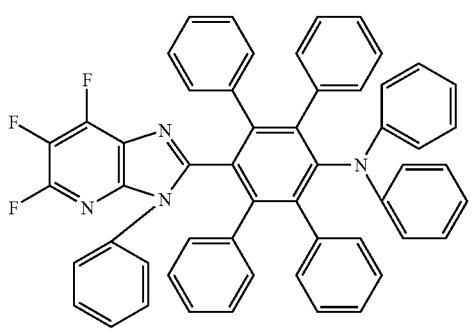

-continued
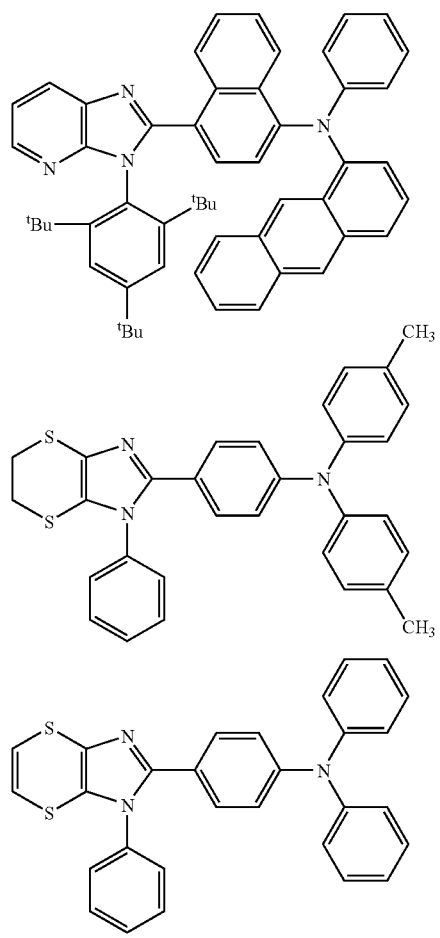
IB-41
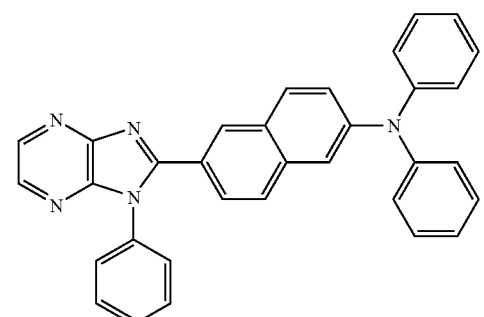
IB-39
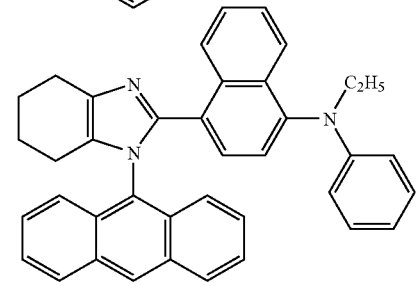
IB-40
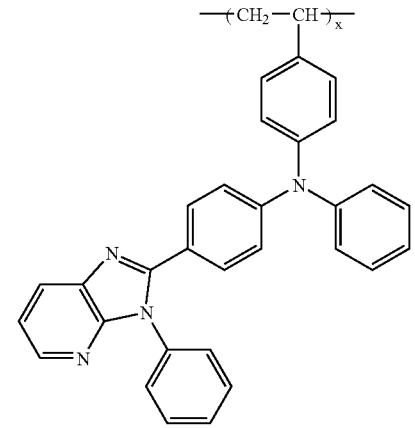
IB-42
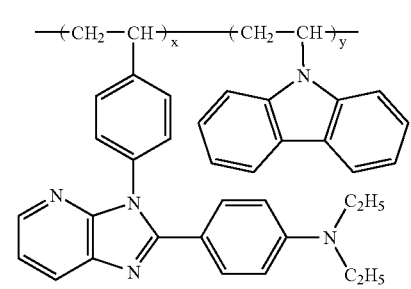
Weight-average molecular weight: 18,000
(in terms of polystyrene)
IB-43
IB-44
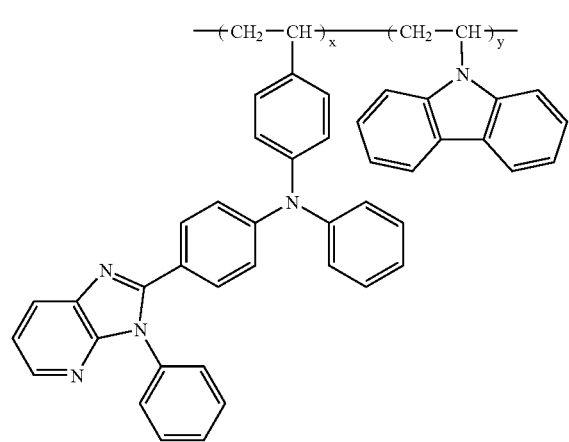
Weight-average molecular weight: 20,000
x:y = 1:5 (weight ratio)
(in terms of polystyrene)
IB-45
IB-46
Weight-average molecular weight: 20,000
x:y = 1:5 (weight ratio)
(in terms of polystyrene)

-continued
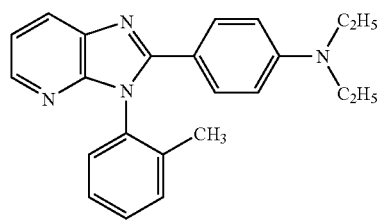
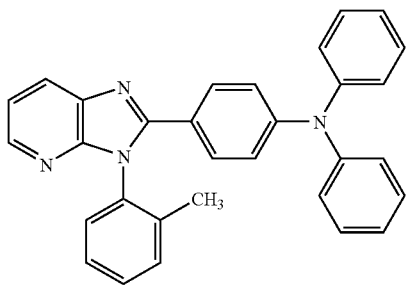
IB-47                IB-48
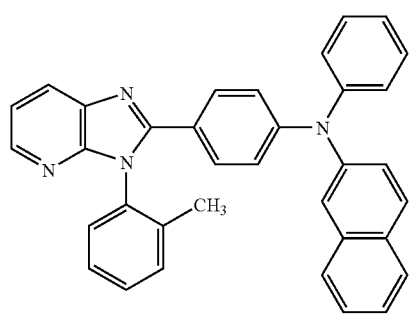
IB-49                IB-50
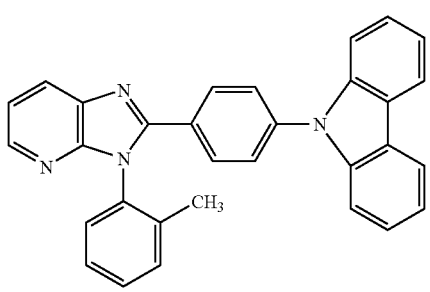
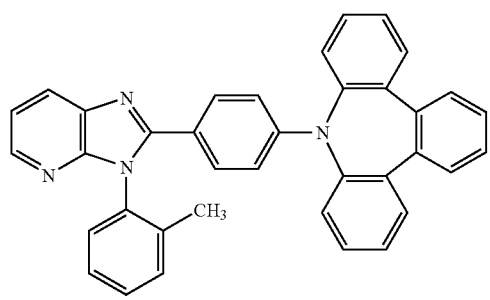
IB-51                IB-52
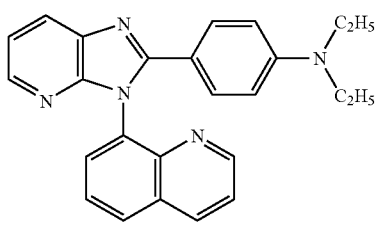
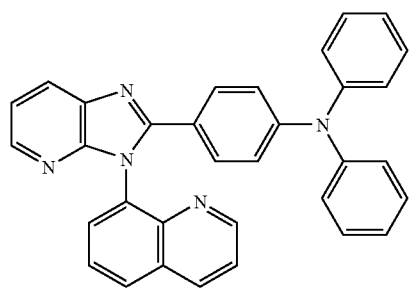
IB-53                IB-54
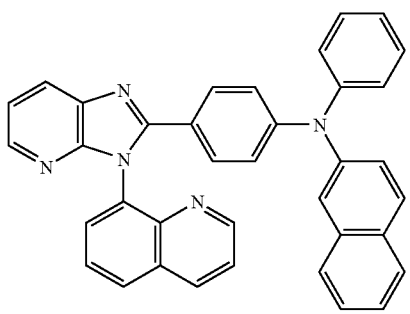
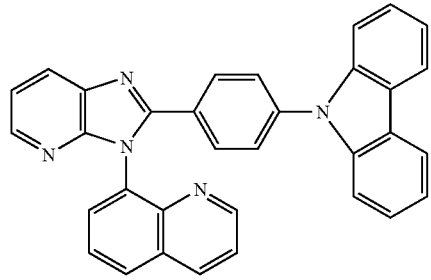
IB-55                IB-56
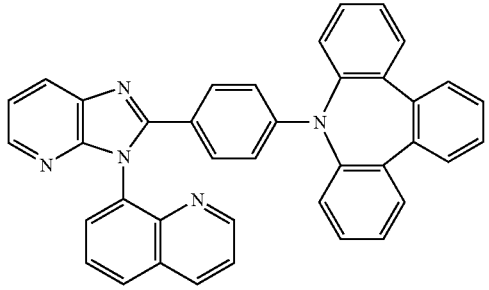

-continued
IB-57
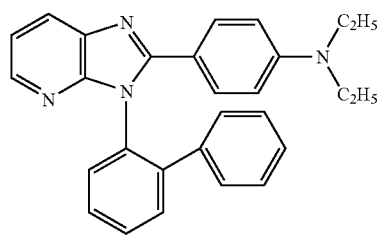
IB-58
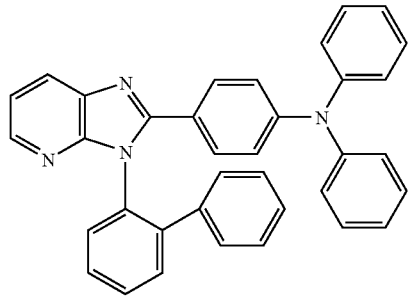
IB-59
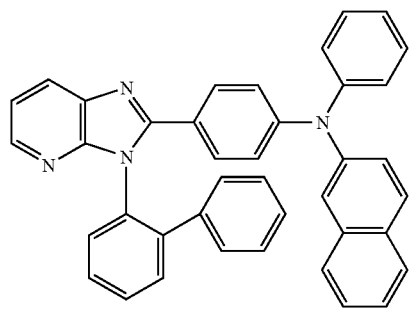
IB-60
IB-61
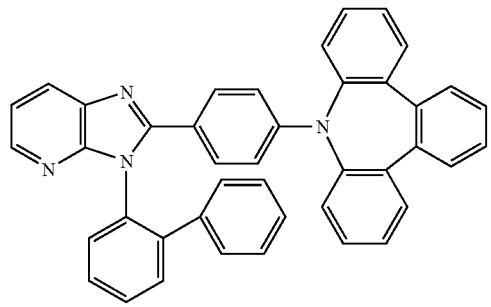
IB-62
IB-63
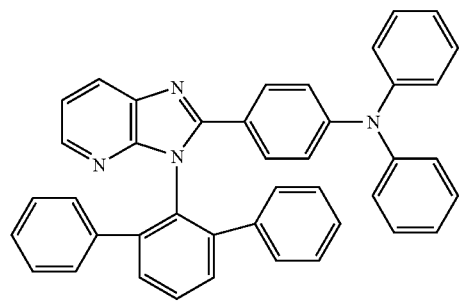
IB-64
IB-65
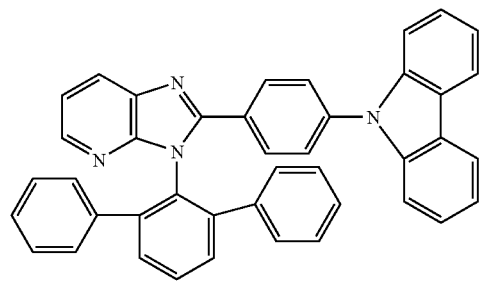
IB-66
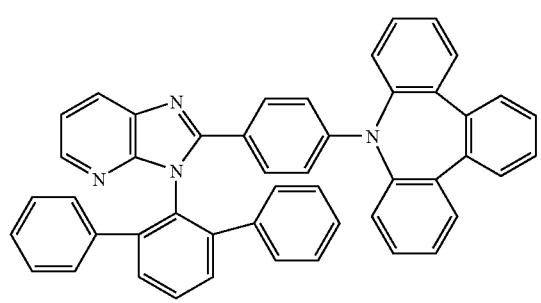

-continued
IB-67
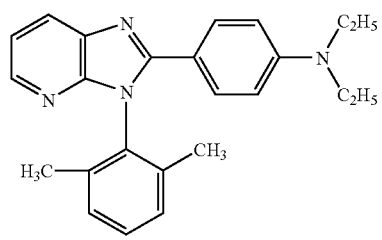
IB-68
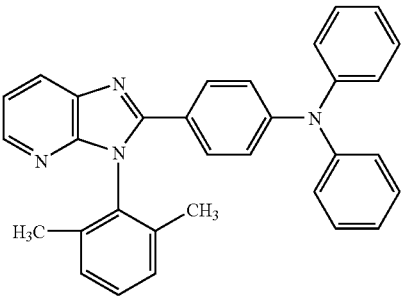
IB-69
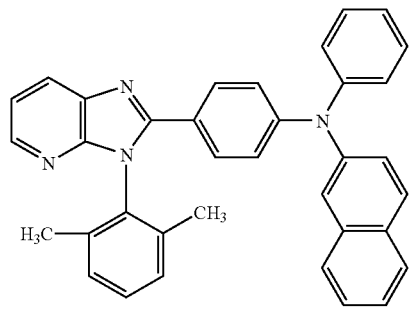
IB-70
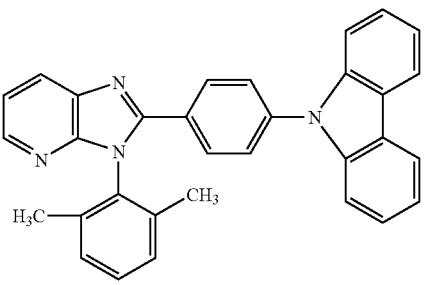
IB-71
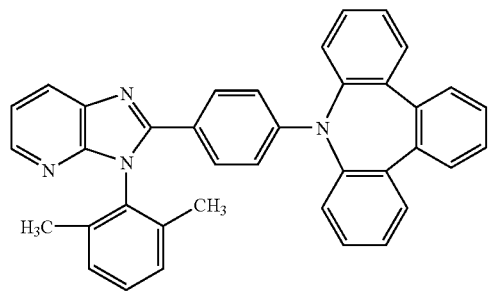
IB-72
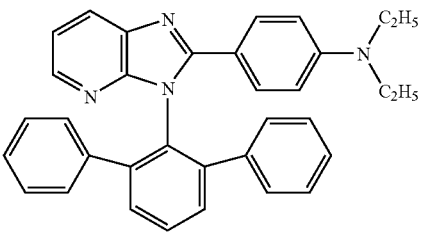
IB-73
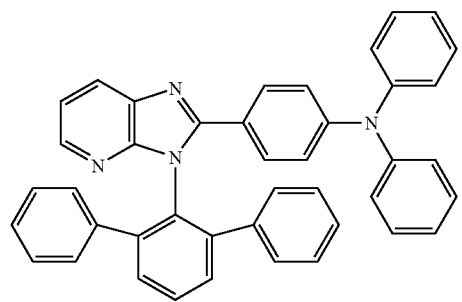
IB-74
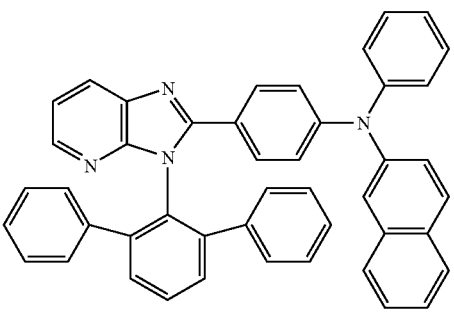
IB-75
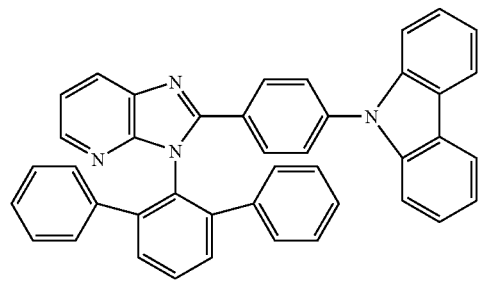
IB-76
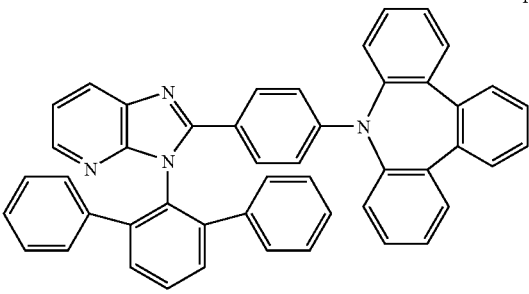

-continued
IB-77
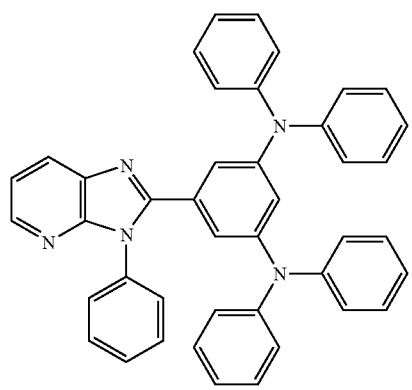
IB-78
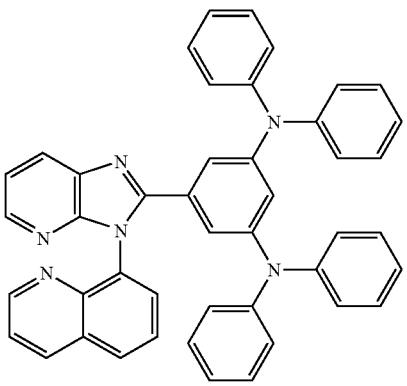
IB-79
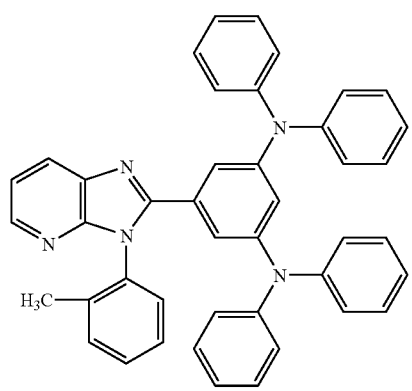
IB-80
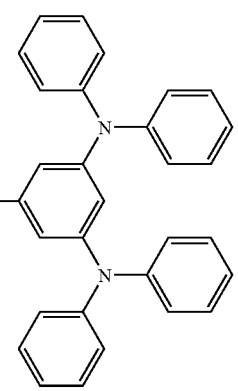
IB-81
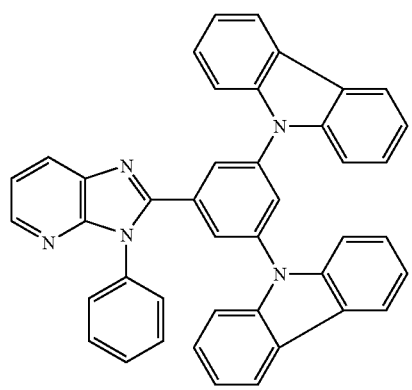
IB-82
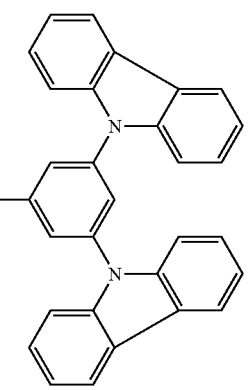
IB-83
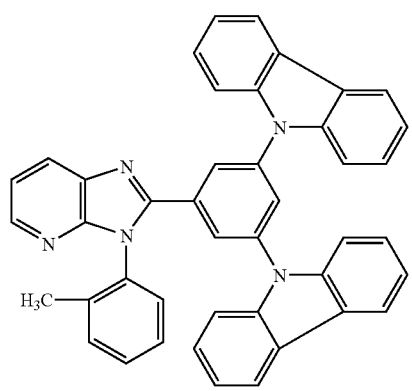
IB-84
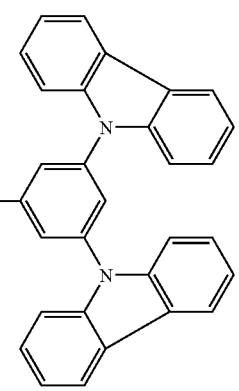

-continued
IB-85
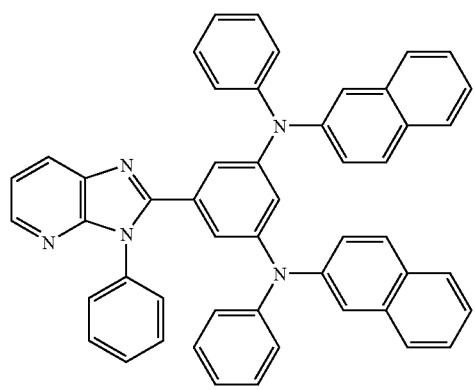
IB-86
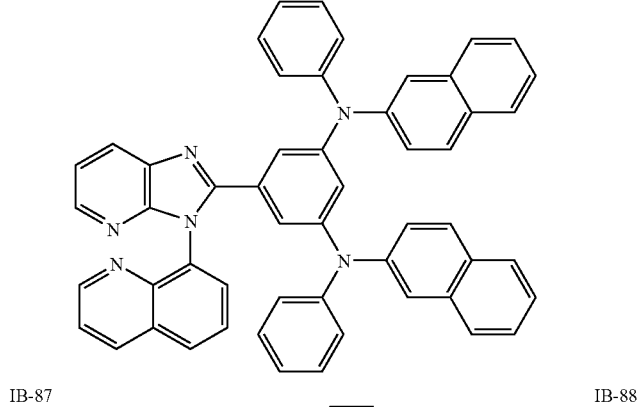
IB-87
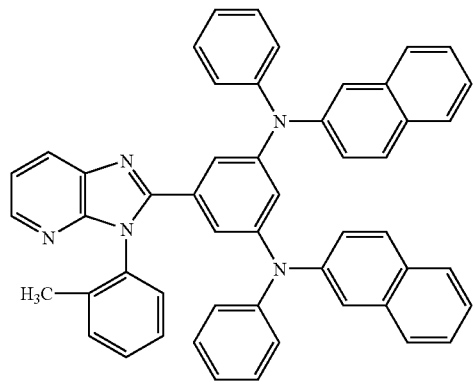
IB-88
IB-89
IB-90
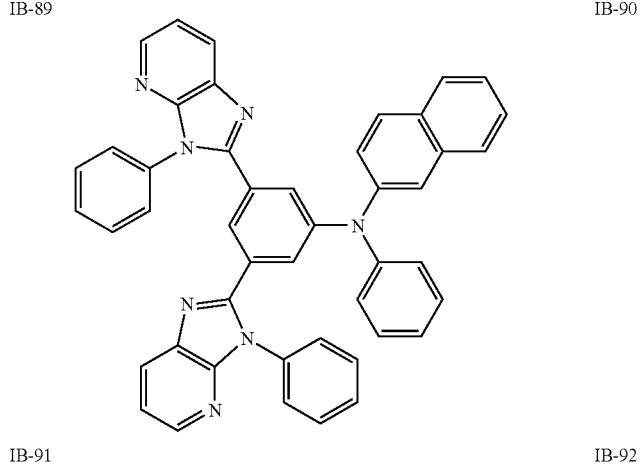
IB-91
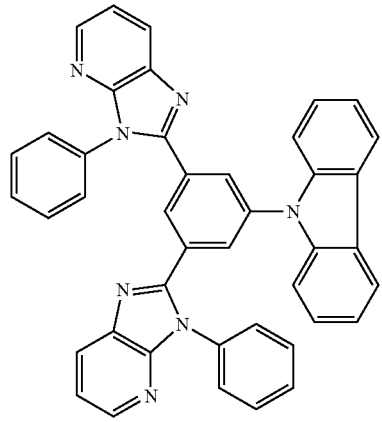
IB-92
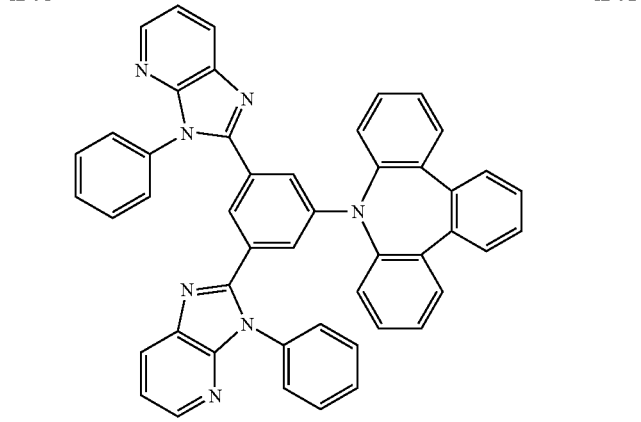

IB-93

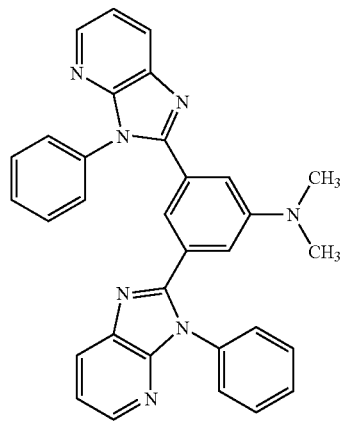

IB-94

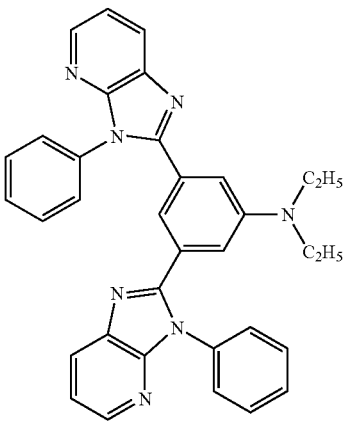

The above-mentioned compounds may be their tautomers.

Synthesis methods of the compounds of the invention represented by general formula (IB) are illustrated below, showing specific examples thereof.

SYNTHESIS EXAMPLE 1

Synthesis of Example Compound IB-2

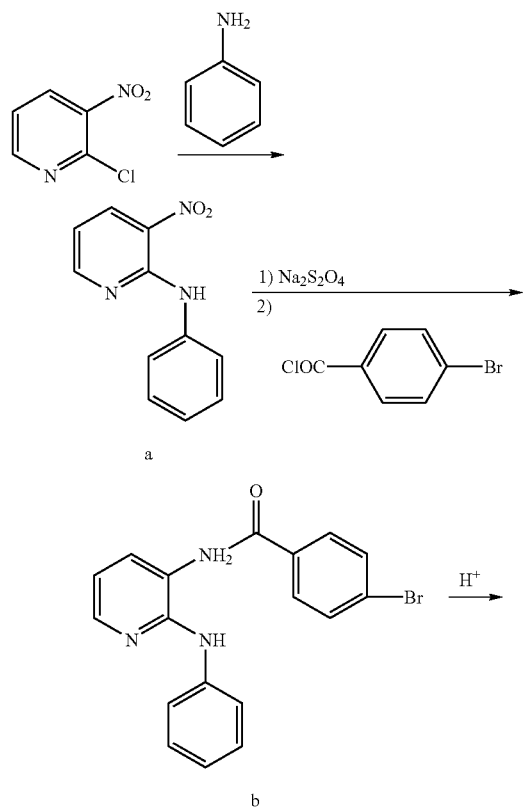

-continued

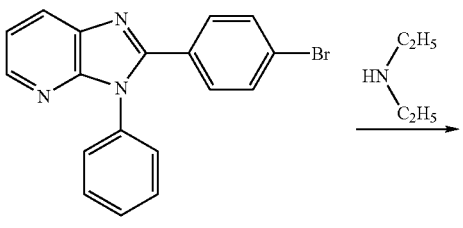

c

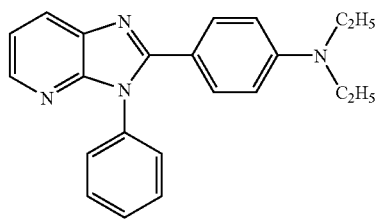

Example Compound IB-2

1-1. Synthesis of Compound a

Aniline (45.7 g (0.490 mol)) was added to 50.8 g (0.320 mol) of 2-chloro-3-nitropyridine, 90.8 g (0.657 mol) of potassium carbonate, 7.90 g (0.0416 mol) of copper(I) iodide and 300 ml of toluene with stirring at room temperature in an atmosphere of nitrogen. After heating under reflux for 5 hours, the reaction solution was filtered, and the filtrate was concentrated under reduced pressure. After purification by silica gel column chromatography (developing solvent: chloroform), recrystallization from chloroform/hexane was conducted to obtain 45.7 g (0.21 mol) of compound a. The yield was 66%.

1-2. Synthesis of Compound b

A solution of 200 g (1.149 mol) of sodium hydrosulfite in 700 ml of water was added dropwise to a solution of 60.0 g (0.232 mol) of compound a in 500 ml of tetrahydrofuran with stirring at room temperature in an atmosphere of nitrogen. Methanol (50 ml) was further added thereto, followed by stirring for 1 hour. Then, 500 ml of ethyl acetate was added, and a solution of 40 g (0.476 mol) of sodium hydrogencarbonate in 400 ml of water was added. A solution of 61 g (0.232 mol) of 4-bromobenzoyl chloride in 170 ml of ethyl acetate was further added dropwise, followed by stirring at room temperature for 5 hours. After extraction with ethyl acetate, the extract was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 58.9 g (0.16 mol) of compound b. The yield was 69%.

1-3. Synthesis of Compound c

Compound b (59.5 g (0.16 mol)) was dissolved in 1 liter of xylene, and 9.5 g (0.05 mol) of p-toluenesulfonic acid monohidrate was added thereto, followed by azeotropic dehydration with heating under reflux in an atmosphere of nitrogen for 5 hours. After the reaction solution was cooled to room temperature, the precipitated solid was collected by filtration, and recrystallized from ethanol/chloroform, thereby obtaining 42.8 g (0.12 mol) of compound c. The yield was 76%.

1-4. Synthesis of Example Compound IB-2

Diethylamine (1.02 g (0.014 mol)) was dissolved in 50 ml of xylene, and 1.6 g (0.017 mol) of sodium methoxide, 75 mg (0.336 mmol) of palladium (II) acetate and 280 mg (0.0014 mol) of tri-t-butylphosphine were added thereto, followed by stirring. Then, 5.0 g (0.014 mol) of compound c was added thereto, followed by heating under reflux for 4 hours. After the reaction solution was cooled to room temperature, the insoluble matter was removed by filtration, and the filtrate was extracted from ethyl acetate. The organic phase was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 1.5 g (0.0044 mol) of example compound IB-2. The yield was 31%, and the melting point thereof was 152° C.

SYNTHESIS EXAMPLE 2

Synthesis of Example Compound IB-3

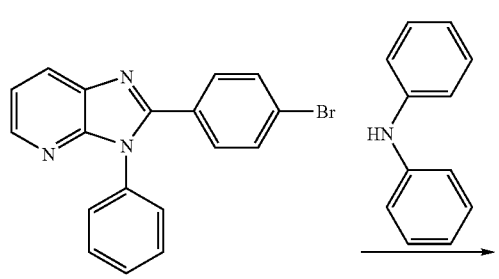

c

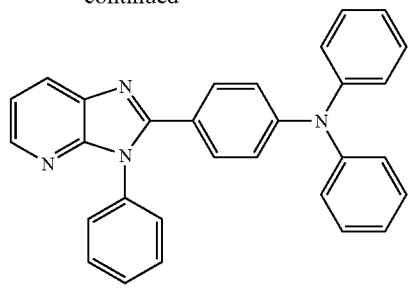

Example Compound IB-3

Diphenylamine (2.4 g (0.014 mol)) was dissolved in 50 ml of xylene, and 1.6 g (0.017 mol) of sodium methoxide, 75 mg (0.336 mmol) of palladium (II) acetate and 280 mg (0.0014 mol) of tri-t-butylphosphine were added thereto, followed by stirring. Then, 5.0 g (0.014 mol) of compound c was added thereto, followed by heating under reflux for 8 hours. After the reaction solution was cooled to room temperature, the insoluble matter was removed by filtration, and the filtrate was extracted from ethyl acetate. The organic phase was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 2.8 g (0.0064 mol) of example compound IB-3. The yield was 46%, and the melting point thereof was 215° C.

SYNTHESIS EXAMPLE 3

Synthesis of Example Compound IB-4

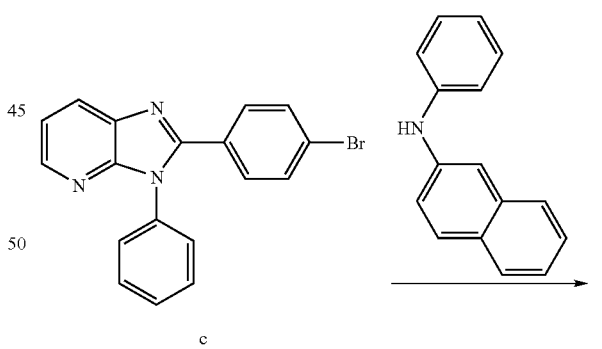

c

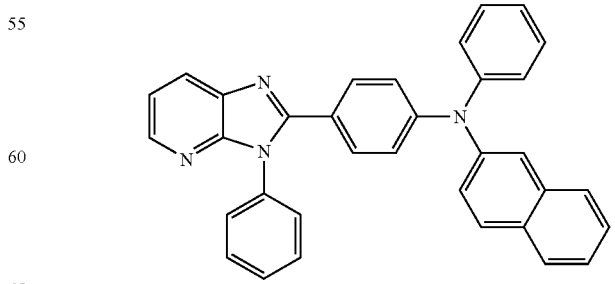

Example Compound IB-4

2-Naphthylphenylamine (3.1 g (0.014 mol)) was dissolved in 50 ml of xylene, and 1.6 g (0.017 mol) of sodium methoxide, 75 mg (0.336 mmol) of palladium (II) acetate and 280 mg (0.0014 mol) of tri-t-butylphosphine were added thereto, followed by stirring. Then, 5.0 g (0.014 mol) of compound c was added thereto, followed by heating under reflux for 6 hours. After the reaction solution was cooled to room temperature, the insoluble matter was removed by filtration, and the filtrate was extracted from ethyl acetate. The organic phase was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 2.4 g (0.0049 mol) of example compound IB-4. The yield was 35%, and the melting point thereof was 212° C.

SYNTHESIS EXAMPLE 4

Synthesis of Example Compound IB-5

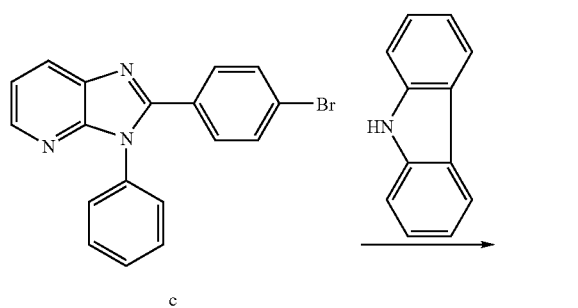

Example Compound IB-5

Carbazole (2.3 g (0.014 mol)) was dissolved in 50 ml of xylene, and 1.6 g (0.017 mol) of sodium methoxide, 75 mg (0.336 mmol) of palladium (II) acetate and 280 mg (0.0014 mol) of tri-t-butylphosphine were added thereto, followed by stirring. Then, 5.0 g (0.014 mol) of compound c was added thereto, followed by heating under reflux for 8 hours. After the reaction solution was cooled to room temperature, the insoluble matter was removed by filtration, and the filtrate was extracted from ethyl acetate. The organic phase was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 2.6 g (0.0060 mol) of example compound IB-5. The yield was 43%, and the melting point thereof was 193° C.

SYNTHESIS EXAMPLE 5

Synthesis of Example Compound IB-6

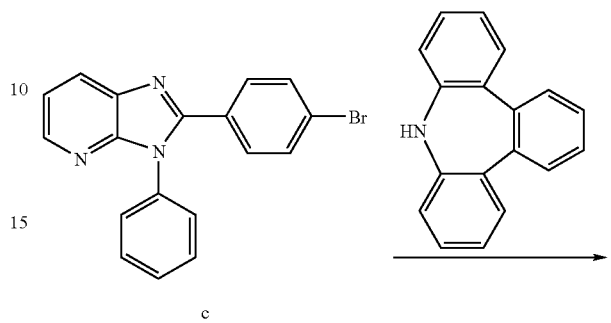

Example Compound IB-6

Tribenzoazepine (1.4 g (0.0057 mol)) was dissolved in 50 ml of xylene, and 0.7 g (0.0069 mol) of sodium methoxide, 31 mg (0.14 mmol) of palladium (II) acetate and 115 mg (0.00057 mol) of tri-t-butylphosphine were added thereto, followed by stirring. Then, 2.0 g (0.0057 mol) of compound c was added thereto, followed by heating under reflux for 8 hours. After the reaction solution was cooled to room temperature, the insoluble matter was removed by filtration, and the filtrate was extracted from ethyl acetate. The organic phase was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 0.79 g (0.0015 mol) of example compound IB-6. The yield was 27%, and the melting point thereof was 275° C.

SYNTHESIS EXAMPLE 6

Synthesis of Example Compound IB-77

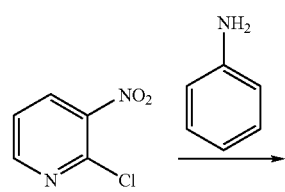

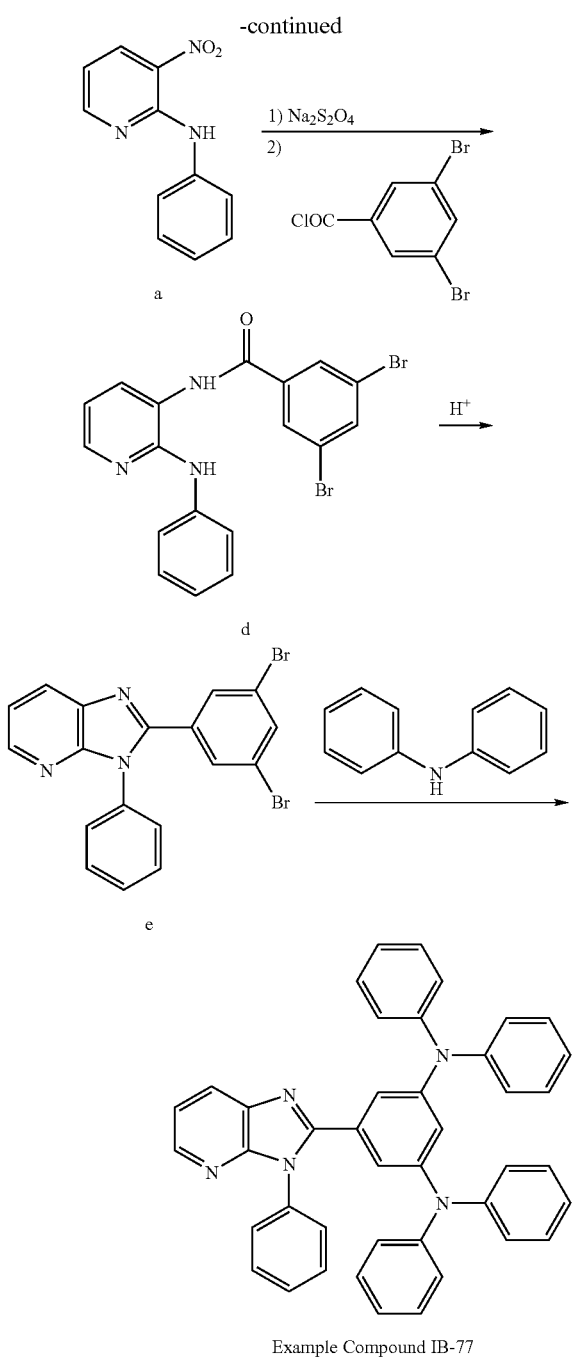

Example Compound IB-77

6-1. Synthesis of Compound d

A solution of 62.3 g (0.358 mol) of sodium hydrosulfite in 175 ml of water was added dropwise to a solution of 15.4 g (0.072 mol) of compound a in 125 ml of tetrahydrofuran with stirring at room temperature in an atmosphere of nitrogen. Methanol (25 ml) was further added thereto, followed by stirring for 1 hour. Then, 125 ml of ethyl acetate was added, and a solution of 12 g (0.143 mol) of sodium hydrogencarbonate in 100 ml of water was added. A solution of 21.3 g (0.072 mol) of 3,5-dibromobenzoyl chloride in 45 ml of ethyl acetate was further added dropwise, followed by stirring at room temperature for 5 hours. After extraction with ethyl acetate, the extract was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 9.8 g (0.022 mol) of compound d. The yield was 31%.

6-2. Synthesis of Compound e

Compound d (8.5 g (0.019 mol)) was dissolved in 150 ml of xylene, and 1.08 g (0.0057 mol) of p-toluenesulfonic acid monohidrate was added thereto, followed by azeotropic dehydration with heating under reflux in an atmosphere of nitrogen for 5 hours. After the reaction solution was cooled to room temperature, the precipitated solid was collected by filtration, and recrystallized from ethanol/chloroform, thereby obtaining 5.6 g (0.013 mol) of compound e. The yield was 71%.

6-3. Synthesis of Example Compound IB-77

Diphenylamine (118 mg (0.70 mmol)) was dissolved in 10 ml of xylene, and 81 mg (0.84 mmol) of sodium t-butoxide, 0.038 mg (0.17 pmol) of palladium (II) acetate and 0.14 mg (0.7 mmol) of tri-t-butylphosphine were added thereto, followed by stirring. Then, 300 mg (0.70 mmol) of compound c was added thereto, followed by heating under reflux for 4 hours. After the reaction solution was cooled to room temperature, the insoluble matter was removed by filtration, and the filtrate was extracted from ethyl acetate. The organic phase was washed with successive water and saturated brine, and dried on anhydrous magnesium sulfate. Then, the solvent was removed by distillation under reduced pressure. After purification by silica gel column chromatography (developing solvent: chloroform) recrystallization from chloroform/hexane was conducted to obtain 60 mg (0.099 mmol) of example compound IB-77. The yield was 14%.

SYNTHESIS EXAMPLE 7

Synthesis of Example Compound IB-89

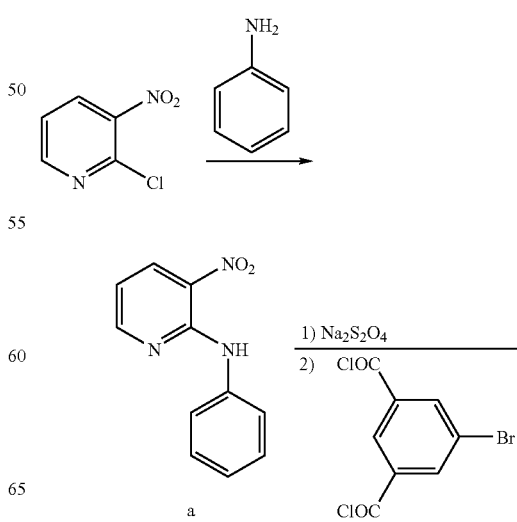

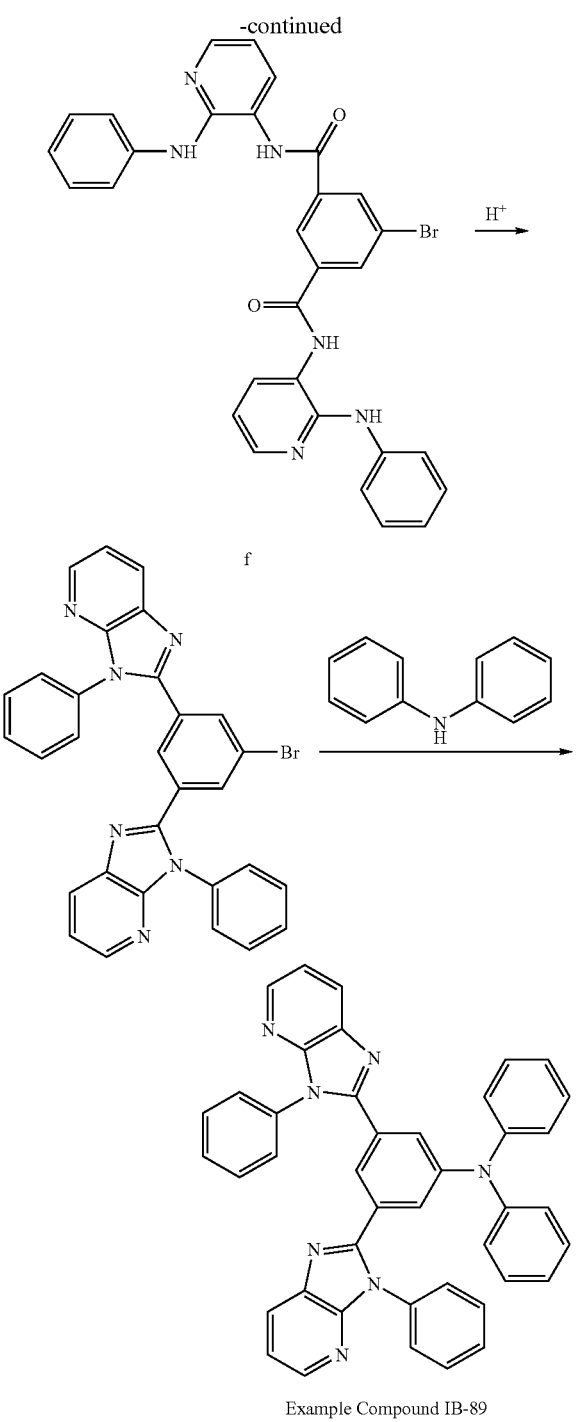

Example Compound IB-89 lowed by stirring at room temperature for 4 hours. After extraction with ethyl acetate, the extract was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 14.9 g (0.026 mol) of compound f. The yield was 22%.

7-2. Synthesis of Compound g

Compound f (14.9 g (0.026 mol)) was dissolved in 150 ml of xylene, and 0.5 g (0.0026 mol) of p-toluenesulfonic acid monohidrate was added thereto, followed by azeotropic dehydration with heating under reflux in an atmosphere of nitrogen for 6 hours. After the reaction solution was cooled to room temperature, the precipitated solid was collected by filtration, and recrystallized from ethanol/chloroform, thereby obtaining 9.2 g (0.017 mol) of compound g. The yield was 66%.

7-3. Synthesis of Example Compound IB-89

Diphenylamine (405 mg (2.39 mmol)) was dissolved in 20 ml of xylene, and 276 mg (2.87 mmol) of sodium t-butoxide, 0.13 mg (0.00057 mmol) of palladium (II) acetate and 0.48 mg (0.0024 mmol) of tri-t-butylphosphine were added thereto, followed by stirring. Then, 1000 mg (1.84 mmol) of compound g was added thereto, followed by heating under reflux for 3 hours. After the reaction solution was cooled to room temperature, the insoluble matter was removed by filtration, and the filtrate was extracted from ethyl acetate. The organic phase was washed with successive water and saturated brine, and dried on anhydrous magnesium sulfate. Then, the solvent was removed by distillation under reduced pressure. After purification by silica gel column chromatography (developing solvent: chloroform), recrystallization from chloroform/hexane was conducted to obtain 234 mg (0.37 mmol) of example compound IB-89. The yield was 20%.

The light emitting devices containing the compounds of the invention are described below. Although there is no particular limitation on methods for forming organic layers of the light emitting devices containing the compounds of the invention, methods such as resistance heating vapor deposition, electron beam processing, sputtering, molecular lamination, coating, ink jet processing and printing are used. In terms of their characteristics and production, resistance heating vapor deposition and coating are preferred.

When the compounds of the invention are used as the materials for the light emitting devices, they may be used as any of hole injection-transfer layers, electron injection-transfer layers and light emitting layers. However, they are preferably used as light emitting layers.

The light emitting device of the invention is a device in which a light emitting layer or a plurality of organic compound films including a light emitting layer are formed between a pair of electrodes, an anode and a cathode, and may have a hole injection layer, a hole transfer layer, an electron injection layer, an electron transfer layer and/or a protective layer, in addition to the light emitting layer. Each of these layers may be provided with another function. Various materials can be used for the formation of the respective layers.

The anodes supply holes to the hole injection layers, the hole transfer layers and the light emitting layers, and can be formed of metals, alloys, metal oxides, conductive compounds or mixtures thereof, preferably materials having a work function of 4 eV or more. Specific examples thereof 7-1. Synthesis of Compound f A solution of 102 g (0.585 mol) of sodium hydrosulfite in 300 ml of water was added dropwise to a solution of 25.2 g (0.117 mol) of compound a in 200 ml of tetrahydrofuran with stirring at room temperature in an atmosphere of nitrogen. Methanol (45 ml) was further added thereto, followed by stirring for 1 hour. Then, 200 ml of ethyl acetate was added, and a solution of 20 g (0.234 mol) of sodium hydrogencarbonate in 100 ml of water was added. A solution of 66.0 g (0.234 mol) of 5-bromo-m-phthaloyl chloride in 100 ml of ethyl acetate was further added dropwise, folinclude conductive metal oxides such as tin oxide, zinc oxide, indium oxide and indium tin oxide (ITO), metals such as gold, silver, chromium and nickel, further mixtures or laminates of the metals with the conductive metal oxides, inorganic conductive materials such as copper iodide and copper sulfide, organic conductive materials such as polyaniline, polythiophene and polypyrrole, and laminates thereof with ITO. Preferred are conductive metal oxides, and ITO is particularly preferred in terms of productivity, high conductivity and transparency. The thickness of the anode is usually preferably from 10 nm to 5 μm, more preferably from 50 nm to 1 μm, and still more preferably from 100 nm to 500 nm.

As the anode, one in which layer formation is carried out on soda-lime glass, non-alkali glass or a transparent resin substrate is usually used. When glass is used, non-alkali glass is preferably used for decreasing ions eluted from glass. When soda lime-glass is used, it is preferable to use one provided with a barrier coat of silica or the like. There is no particular limitation on the thickness of the substrate, as long as it is sufficient to keep its mechanical strength. When glass is used, the thickness is usually 0.2 mm or more, and preferably 0.7 mm or more.

Various methods are used for the preparation of the anodes depending on the kind of material. For example, in the case of ITO, film formation is carried out by methods such as electron beam processing, sputtering, resistance heating vapor deposition, chemical reaction (sol-gel processing) and coating of a dispersion of ITO.

The anodes are also capable of decreasing the driving voltage of the devices and increasing the light emitting efficiency by washing or other treatment. For example, in the case of ITO, UV-ozone treatment and plasma treatment are effective.

The cathodes supply electrons to the electron injection layers, the electron transfer layers and the light emitting layers, and are selected considering adhesion to layers adjacent to the negative electrodes, such as the electron injection layers, the electron transfer layers and the light emitting layers, ionization potential and stability. As materials for the cathodes, metals, alloys, metal oxides, conductive compounds or mixtures thereof can be used. Specific examples thereof include alkali metals (for example, Li, Na, K and Cs), fluorides thereof or oxides thereof; alkali earth metals (for example, Mg and Ca), fluorides thereof or oxides thereof; gold, silver, lead, aluminum, sodium-potassium alloys or mixed metals thereof; lithium-aluminum alloys or mixed metals thereof; magnesium-silver alloys or mixed metals thereof; and rare earth metals such as indium and ytterbium. Preferred are materials having a work function of 4 eV or less, and more preferred are aluminum, lithium-aluminum alloys or mixed metals thereof and magnesium-silver alloys or mixed metals thereof. The thickness of the cathode is usually preferably from 10 nm to 5 μm, more preferably from 50 nm to 1 μm, and still more preferably from 100 nm to 1 μm.

For the preparation of the cathodes, methods such as electron beam processing, sputtering, resistance heating vapor deposition and coating are used. The metals can be vapor deposited as simple substances, or two or more components can be vapor deposited at the same time. Further, it is also possible to vapor deposit the plurality of metals at the same time to form an alloy electrode, or an alloy previously prepared may also vapor deposited. It is preferred that the sheet resistance of the anodes and the cathodes is so low as several hundred Ω/square(□) or less.

Materials for the light emitting layers may be any, as long as they can form layers having the function of being able to inject holes from the anodes, the hole injection layers or the hole transfer layers and electrons from the cathodes, the electron injection layers or the electron transfer layers, upon electric field application, the function of transferring injected charges, or the function of providing the field of recombination of holes with electrons to emit light. Examples of the compounds used in the light emitting layers include benzoxazole derivatives, benzimidazole derivatives, benzthiazole derivatives, styrylbenzene derivatives, polyphenyl derivatives, diphenylbutadiene derivatives, tetraphenyl-butadiene derivatives, naphthalimide derivatives, coumarin derivatives, perylene derivatives, perynone derivatives, oxadiazole derivatives, aldazine derivatives, cyclopentadiene derivatives, bis(styryl)anthracene derivatives, quinacridone derivatives, pyrrolopyridine derivatives, thiadiazolopyridine derivatives, styrylamine derivatives, aromatic dimethylidyne compounds, various metal complexes represented by metal complexes of 8-quinolinol derivatives, orthometalated complex and rare earth complexes, and polymers such as polythiophene, polyphenylene and polyphenylenevinylene, as well as the compounds of the invention. Although there is no particular limitation on the thickness of the light emitting layer, it is usually preferably from 1 nm to 5 μm, more preferably from 5 nm to 1 μm, and still more preferably from 10 nm to 500 nm.

Although there is no particular limitation on methods for forming the light emitting layers, methods such as resistance heating vapor deposition, electron beam processing, sputtering, molecular lamination, coating (spin coating, casting and dip coating), LB processing, ink jet processing and printing are used. Preferred are resistance heating vapor deposition and coating.

Materials for the hole injection layers and the hole transfer layers may be any, as long as they have any of the function of injecting holes from the anodes, the function of transferring holes and the function of blocking electrons injected from the cathodes. Specific examples thereof include carbazole derivatives, imidazole derivatives, triazole derivatives, oxazole derivatives, oxadiazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, poly(N-vinylcarbazole) derivatives, aniline copolymers, and conductive high molecular oligomers such as thiophene oligomers and polythiophene, as well as the compounds of the invention. Although the thickness of the hole injection layer and the hole transfer layer is not particularly limited by the material, it is usually preferably from 1 nm to 5 μm, more preferably from 5 nm to 1 μm, and still more preferably from 10 nm to 500 nm. The hole injection layer and the hole transfer layer may have either a monolayer structure comprising one kind or two or more kinds of the above-mentioned materials, or a multilayer structure having a plurality of layers each comprising the same composition or different compositions.

As methods for forming the hole injection layers and the hole transfer layers, vacuum vapor deposition, LB processing, ink jet processing, printing and coating (spin coating, casting and dip coating) of the above-mentioned materials for the hole injection layers and the hole transfer layers dissolved or dispersed in solvents are used. In the case of coating, the materials can be dissolved or dispersed together with resin components. The resin components include, for example, polyvinyl chloride, polycarbonates, polystyrene, polymethyl methacrylate, polyesters, polysulfones, polyphenylene oxide, polybutadiene, poly(N-vinylcarbazole), hydrocarbon resins, ketone resins, phenoxy resins, polyamides, ethyl cellulose, vinyl acetate, ABS resins, polyurethane, melamine resins, unsaturated polyester resins, alkyd resins, epoxy resins and silicone resins.

Materials for the electron injection layers and the electron transfer layers may be any, as long as they have any of the function of injecting electrons from the cathodes, the function of transferring electrons and the function of blocking holes injected from the anodes. Specific examples thereof include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, aromatic tetracarboxylic anhydrides of naphthalene, perylene and the like, phthalocyanine derivatives, and various metal complexes represented by metal complexes of 8-quinolinol derivatives, metallophthalocyanine, and metal complexes each having benzoxazole or benzothiazole as a ligand, as well as the compounds of the invention. Although there is no particular limitation on the thickness of the electron injection layer and the electron transfer layer, it is usually preferably from 1 nm to 5 μm, more preferably from 5 nm to 1 μm, and still more preferably from 10 nm to 500 nm. The electron injection layer and the electron transfer layer may have either a monolayer structure comprising one kind or two or more kinds of the above-mentioned materials, or a multilayer structure having a plurality of layers each comprising the same composition or different compositions.

As methods for forming the electron injection layers and the electron transfer layers, vacuum vapor deposition, LB processing, ink jet processing, printing and coating (spin coating, casting and dip coating) of the above-mentioned materials for the hole injection layers and the hole transfer layers dissolved or dispersed in solvents are used. In the case of coating, the materials can be dissolved or dispersed together with resin components. As the resin components, for example, ones illustrated in the case of the hole injection layers and the hole transfer layers can be applied.

Materials for the protective layers may be any, as long as they have the function of inhibiting promoters of device deterioration such as water and oxygen from entering the devices. Specific examples thereof include metals such as In, Sn, Pb, Au, Cu, Ag, Al, Ti and Ni, metal oxides such as MgO, SiO, $SiO_2$, $Al_2O_3$, GeO, NiO, CaO, BaO, $Fe_2O_3$, $Y_2O_3$ and $TiO_2$, metal fluorides such as $MgF_2$, LiF, $AlF_3$ and $CaF_2$, polyethylene, polypropylene, polymethyl methacrylate, polyimides, polyureas, polytetrafluoroethylene, polychlorotrifluoroethylene, polydichlorodifluoroethylene, copolymers of chlorotrifluoroethylene and dichlorodifluoroethylene, copolymers obtained by copolymerizing monomer mixtures each containing tetrafluoroethylene and at least one kind of comonomer, fluorine-containing copolymers having cyclic structures on main chains of the copolymers, water-absorptive substances having a water absorption of 1% or more, and moisture-proof substances having a water absorption of 1% or less.

There is no particular limitation on methods for forming the protective layers. For example, vacuum vapor deposition, sputtering, reactive sputtering, MBE (molecular beam epitaxy), cluster ion beam processing, ion plating, plasma polymerization (high-frequency excitation ion plating), plasma CVD, laser CVD, thermal CVD, gas source CVD, coating and ink jet processing can be applied.

The invention will be further illustrated in detail below with reference to the following examples, which are, however, not to be construed as limiting the invention.

COMPARATIVE EXAMPLE 1

A 25-mm×25-mm×0.7-mm glass substrate on which a 150-nm thick ITO film was formed (manufactured by Tokyo Sanyo Shinku Co., Ltd.) was used as a transparent support substrate. After etching and washing of the transparent support substrate, an N,N'-bis(1-naphthyl)-N,N'-diphenylbenzidine (NPD) layer having a thickness of about 40 nm, a blue light emitting material B1 layer having a thickness of about 20 nm and an electron transfer material ETM1 layer having a thickness of about 40 nm were formed on the substrate in this order by vapor deposition in a vacuum of $10^{-3}$ to $10^{-4}$ Pa at a vapor deposition rate of about 0.4 nm/second, with the substrate kept at room temperature. A patterned mask (a mask giving a light emitting area of 5 mm×5 mm) was placed on the organic thin layer, and magnesium/silver of 10/1 were concurrently vapor deposited over it to a thickness of 250 nm in a vapor deposition apparatus, followed by vapor deposition of silver to a thickness of 300 nm. Thus, a device was prepared. With a 2400 type source measure unit manufactured by Toyo Technica Corp., a direct current constant voltage was applied to the EL device to allow the device to emit light, using ITO as an anode and Mg/Ag as a cathode. The luminance was measured with a BM-8 luminance meter manufactured by Topcon Corp., and the light emitting wavelength and the CIE chromaticity coordinates were measured with a PMA-11 spectrum analyzer manufactured by Hamamatsu Photonics K. K. As a result, blue-green luminescence having CIE chromaticity coordinates of (0.19, 0.30) was obtained, and a luminance of 2520 $cd/m^2$ was obtained at 13 V.

Blue Light Emitting Material B1

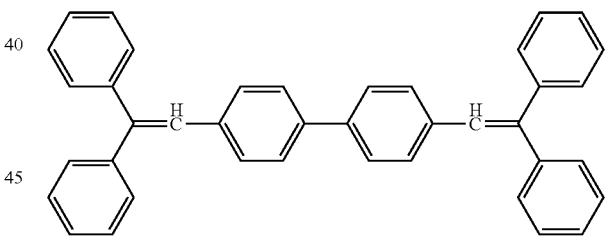

Electron Transfer Material ETM1

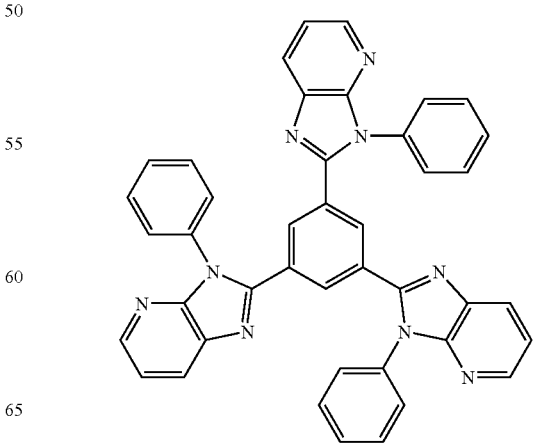

EXAMPLE 1

A device was prepared in the same manner as with Comparative Example 1 with the exception that example compound IA-3 was substituted for blue light emitting material B1, and evaluated in the same manner as with Comparative Example 1. As a result, blue luminescence having a maximum light emitting wavelength of 432 nm and CIE chromaticity coordinates of (0.16, 0.10) was obtained, and a luminance of 2640 cd/m$^2$ was obtained at 14 V.

EXAMPLE 2

For the device prepared in Example 1, the luminance and chromaticity at driving voltages of 8 V and 15 V were measured. As a result, the coordinates were (0.16, 0.10) at a driving voltage of 8 V, and (0.16, 0.11) at 15 V, showing no substantial change in chromaticity.

As apparent from the results, the device containing the compound of the invention showed blue luminescence extremely excellent in color purity, compared with the conventional device, and degradation of blue color purity with an increase in driving voltage was scarcely observed, thus being able to emit blue light high in color purity in a wide driving voltage range.

These results revealed that the use of the compound of the invention as the light emitting material in the device provided blue luminescence having high luminance even in the non-dope type device, and particularly provided the light emitting device extremely excellent in color purity. The results also showed that the device in which the compound of the invention was used could emit blue light high in color purity in a wide driving voltage range.

EXAMPLE 3

An ITO substrate washed in the same manner as with Comparative Example 1 was coated by the spin coat method with a solution in which 40 mg of poly(N-vinylcarbazole), 12 mg of 2-(4-biphenylyl)-5-(4-tert-butylphenyl)-1,3,4-oxadiazole (PBD) and 0.5 mg of example compound IA-1 were dissolved in 3 ml of 1,2-dichloroethane. An organic thin layer formed had a thickness of about 120 nm. A patterned mask (a mask giving a light emitting area of 5 mm×5 mm) was placed on the organic thin layer, and magnesium/silver of 10/1 were concurrently vapor deposited over it to a thickness of 250 nm in a vapor deposition apparatus, followed by vapor deposition of silver to a thickness of 300 nm. Thus, a device was prepared. The device was evaluated in the same manner as with Comparative Example 1. As a result, blue luminescence having a maximum light emitting wavelength of 448 nm and CIE chromaticity coordinates of (0.16, 0.12) was obtained, and a luminance of 1222 cd/m$^2$ was obtained at 14 V.

The results revealed that the use of the compound of the invention in the device allowed high luminance luminescence even in the coating type device usually low in light emitting luminance, and provided the blue light emitting device extremely high in color purity.

EXAMPLE 4

NPD was vapor deposited over an ITO substrate washed in the same manner as with Comparative Example 1 to a thickness of 40 nm, and then example compound IA-40 and NPD were each vapor deposited at a ratio of 1:100 so as to give a thickness of about 20 nm. Then, electron transfer material ETM1 was vapor deposited to a thickness of about 40 nm, and a cathode was vapor deposited to prepare a device. The device was evaluated in the same manner as with Comparative Example 1. As a result, blue luminescence having a maximum light emitting wavelength of 436 nm and CIE chromaticity coordinates of (0.15, 0.12) was obtained, and a luminance of 3130 cd/m$^2$ was obtained at 12 V.

The results revealed that the use of the compound of the invention in the device allowed high luminance luminescence even in the dope type device, and provided the blue light emitting device extremely high in color purity.

According to the invention, the non-dope type and dope type blue light emitting devices could be obtained which were particularly excellent in color purity and exhibited high luminance luminescence, compared with the conventional devices.

COMPARATIVE EXAMPLE 2

A 25-mm×25-mm×0.7-mm glass substrate on which a 150-nm thick ITO film was formed (manufactured by Tokyo Sanyo Shinku Co., Ltd.) was used as a transparent support substrate. After etching and washing of the transparent support substrate, an N,N'-bis(1-naphthyl)-N,N'-diphenylbenzidine (NPD) layer having a thickness of about 40 nm, a blue light emitting material B1 layer having a thickness of about 20 nm and an electron transfer material Alq (tris (8-hydroxyquinolinate) aluminum complex) layer having a thickness of about 40 nm were formed on the substrate in this order by vapor deposition in a vacuum of $10^{-3}$ to $10^{-4}$ Pa at a vapor deposition rate of about 0.4 nm/second, with the substrate kept at room temperature. A patterned mask (a mask giving a light emitting area of 5 mm×5 mm) was placed on the organic thin layer, and magnesium/silver of 10/1 were concurrently vapor deposited over it to a thickness of 250 nm in a vapor deposition apparatus, followed by vapor deposition of silver to a thickness of 300 nm. Thus, a device was prepared. With a 2400 type source measure unit manufactured by Toyo Technica Corp., a direct current constant voltage was applied to the EL device to allow the device to emit light, using ITO as an anode and Mg/Ag as a cathode. The luminance was measured with a BM-8 luminance meter manufactured by Topcon Corp., and the light emitting wavelength and the CIE chromaticity coordinates were measured with a PMA-11 spectrum analyzer manufactured by Hamamatsu Photonics K. K. As a result, blue-green luminescence having CIE chromaticity coordinates of (0.19, 0.30) was obtained, and a luminance of 2400 cd/m$^2$ was obtained at 13 V.

Blue Light Emitting Material B1

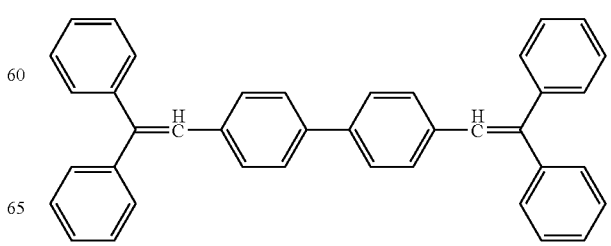

Electron Transfer Material ETM1

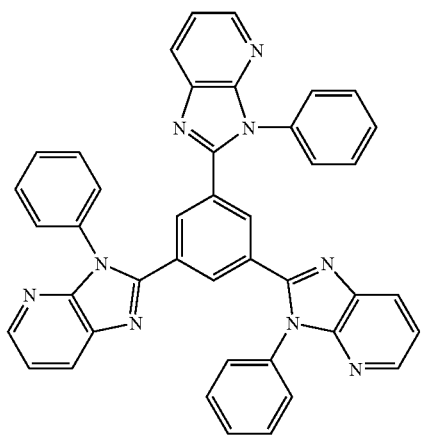

Electron Transfer Material ETM2

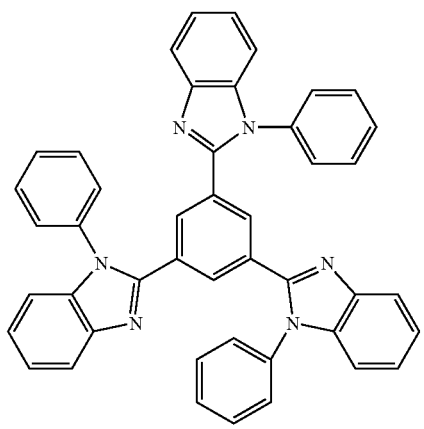

COMPARATIVE EXAMPLE 3

A device was prepared in the same manner as with Comparative Example 2 with the exception that electron transfer material ETM2 was substituted for electron transfer material Alq. The device was evaluated in the same manner as with Comparative Example 2. As a result, blue luminescence having a maximum light emitting wavelength of 432 nm and CIE chromaticity coordinates of (0.19, 0.31) was obtained, and a luminance of 1950 cd/m² was obtained at 14 V.

EXAMPLE 5

A device was prepared in the same manner as with Comparative Example 2 with the exception that example compound IB-3 and electron transfer material ETM1 were substituted for blue light emitting material B1 and electron transfer material Alq, respectively. The device was evaluated in the same manner as with Comparative Example 2. As a result, blue luminescence having a maximum light emitting wavelength of 432 nm and CIE chromaticity coordinates of (0.16, 0.12) was obtained, and a luminance of 2640 cd/m² was obtained at 12 V.

EXAMPLE 6

A device was prepared in the same manner as with Comparative Example 2 with the exception that example compound IB-4 and electron transfer material ETM1 were substituted for blue light emitting material B1 and electron transfer material Alq, respectively. The device was evaluated in the same manner as with Comparative Example 2. As a result, blue luminescence having a maximum light emitting wavelength of 443 nm and CIE chromaticity coordinates of (0.15, 0.11) was obtained, and a luminance of 2800 cd/m² was obtained at 12 V.

EXAMPLE 7

A device was prepared in the same manner as with Comparative Example 2 with the exception that example compound IB-5 and electron transfer material ETM1 were substituted for blue light emitting material B1 and electron transfer material Alq, respectively. The device was evaluated in the same manner as with Comparative Example 2. As a result, blue luminescence having a maximum light emitting wavelength of 435 nm and CIE chromaticity coordinates of (0.16, 0.11) was obtained, and a luminance of 3832 cd/m² was obtained at 14 V.

EXAMPLE 8

A device was prepared in the same manner as with Comparative Example 2 with the exception that example compound IB-6 and electron transfer material ETM1 were substituted for blue light emitting material B1 and electron transfer material Alq, respectively. The device was evaluated in the same manner as with Comparative Example 2. As a result, blue luminescence having a maximum light emitting wavelength of 411 nm and CIE chromaticity coordinates of (0.17, 0.13) was obtained, and a luminance of 3230 cd/m² was obtained at 14 V.

EXAMPLE 9

For the devices prepared in Examples 5 to 8, the luminance and chromaticity at driving voltages of 8 V and 15 V were measured. As a consequence, results shown in Table 1 were obtained.

TABLE 1

| Sample No. | Compound | Max. Luminance (cd/m²) | | CIE Chromaticity Coordinates (x, y) | |
|---|---|---|---|---|---|
| | | When Driven at 8 V | When Driven at 12 V | When Driven at 8 V | When Driven at 12 V |
| 1 | Example Compound IB-3 | 111 | 2640 | (0.16, 0.12) | (0.16, 0.12) |
| 2 | Example Compound IB-4 | 93 | 2800 | (0.15, 0.11) | (0.15, 0.12) |
| 3 | Example Compound IB-5 | 11 | 717 | (0.16, 0.11) | (0.16, 0.12) |
| 4 | Example Compound IB-6 | 18 | 1224 | (0.17, 0.13) | (.16, 0.13) |

As apparent from the results shown in Table 1, in the devices containing the compounds of the invention, degradation of blue color purity with an increase in driving voltage was scarcely observed, thus being able to emit blue light high in color purity in a wide driving voltage range.

EXAMPLE 10

A device was prepared in the same manner as with Comparative Example 2 with the exception that electron transfer material IB-6 and electron transfer material ETM2 were substituted for blue light emitting material B1 and electron transfer material Alq, respectively. The device was evaluated in the same manner as with Comparative Example 2. As a result, blue luminescence having a maximum light emitting wavelength of 411 nm and CIE chromaticity coordinates of (0.17, 0.13) was obtained, and a luminance of 2320 cd/m² was obtained at 12 V.

EXAMPLE 11

The devices prepared in Comparative Example 3 and Example 10 were placed in a glove box the inside of which was replaced with argon gas, and sealed in a sealing vessel made of glass, using a ultraviolet-ray curing type adhesive (XNR 5493 manufactured by Nagase-CIBA Ltd.). The devices were stored in a thermostat having an external temperature of 85° C. for 20 days, and the driving voltages (at a luminance of 200 cd/m²) thereof before and after the storage were measured. As a consequence, results shown in Table 2 were obtained.

TABLE 2

| | Driving Voltage Just after Preparation of Element | Driving Voltage After Storage at 85° C. for 20 Days | Increase in Voltage ΔV |
|---|---|---|---|
| Device of Comparative Example 3 | 12.0 V | 16.5 V | 4.5 V |
| Device of Example 10 | 10.5 V | 11.4 V | 0.9 V |

As apparent from the results shown in Table 2, according to the device containing the compound of the invention, significant improvement in high temperature storage durability was observed, and stable driving was possible for a long period of time.

These results revealed that the use of the compound of the invention as the light emitting material in the device provided blue luminescence having high luminance even in the non-dope type device, and particularly provided the light emitting device extremely excellent in color purity. The results also showed that the device in which the compound of the invention was used could emit blue light high in color purity in a wide driving voltage range, in contrast with a reduction in blue color purity with an increase in driving voltage for the conventional device. Further, according to the device in which the compound of the invention was used, significant improvement in high temperature storage durability was also observed.

EXAMPLE 12

An ITO substrate washed in the same manner as with Comparative Example 2 was coated by the spin coat method with a solution in which 40 mg of poly(N-vinylcarbazole), 12 mg of 2-(4-biphenylyl)-5-(4-tert-butylphenyl)-1,3,4-oxadiazole (PBD) and 0.5 mg of example compound IB-2 were dissolved in 3 ml of 1,2-dichloroethane. An organic thin layer formed had a thickness of about 120 nm. A patterned mask (a mask giving a light emitting area of 5 mm×5 mm) was placed on the organic thin layer, and magnesium/silver of 10/1 were concurrently vapor deposited over it to a thickness of 250 nm in a vapor deposition apparatus, followed by vapor deposition of silver to a thickness of 300 nm. Thus, a device was prepared. The device was evaluated in the same manner as with Comparative Example 2. As a result, blue luminescence having a maximum light emitting wavelength of 450 nm and CIE chromaticity coordinates of (0.16, 0.12) was obtained, and a luminance of 1480 cd/m² was obtained at 15 V.

The results revealed that the use of the compound of the invention in the device allowed high luminance luminescence even in the coating type device usually low in light emitting luminance, and provided the blue light emitting device extremely high in color purity.

According to the invention, the non-dope type blue light emitting devices could be obtained which were particularly excellent in color purity, also excellent in storage durability, and exhibited high luminance luminescence, compared with the conventional devices.

While the invention has been described in detail and with reference to specific embodiments thereof, it will be apparent to one skilled in the art that various changes and modifications can be made therein without departing from the spirit and scope thereof.

This application is based on Japanese patent applications No. Hei-11-305733 filed on Oct. 27, 1999, No. 2000-62472 filed on Mar. 7, 2000 and No. 2000-89632 filed on Mar. 28, 2000, the entire contents of which incorporated herein by reference.

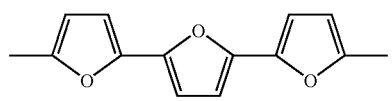

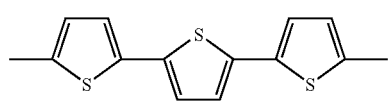

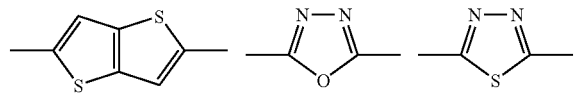

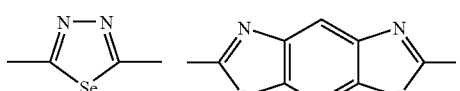

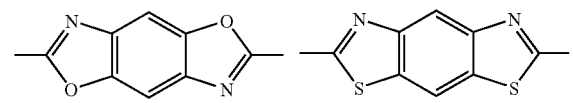

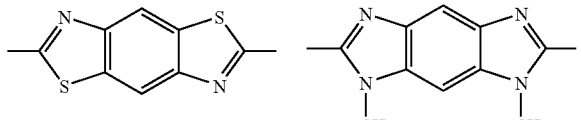

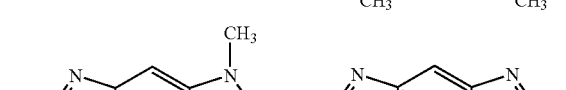

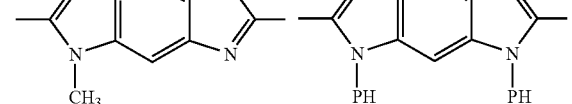

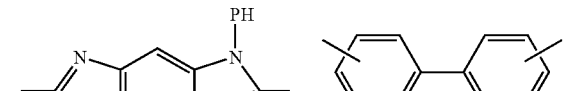

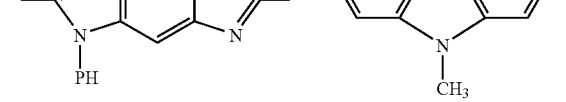

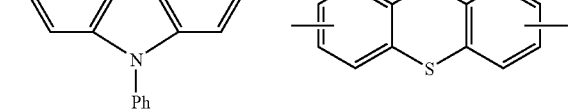

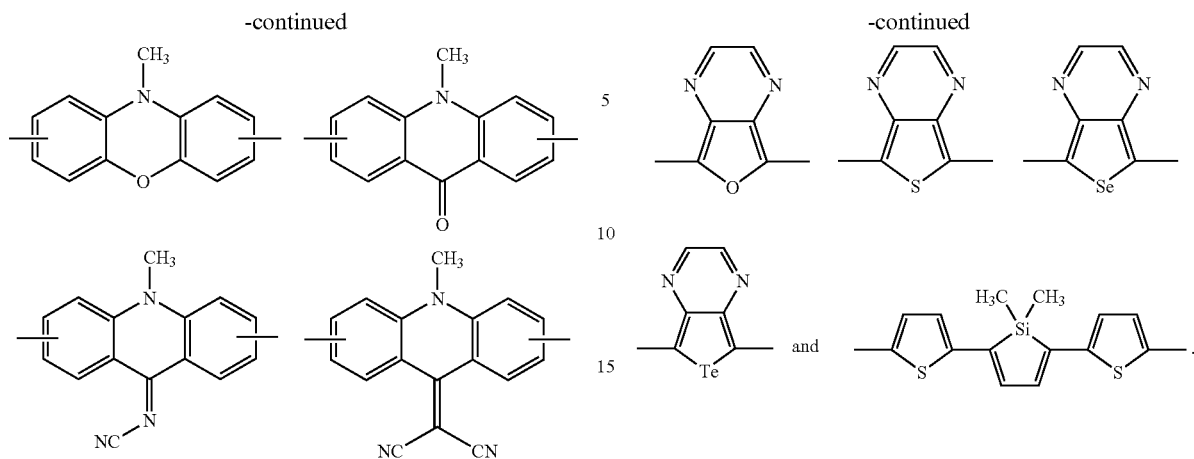

What is claimed is:

1. A light emitting device comprising a light emitting layer or a plurality of thin organic compound layers containing a light emitting layer formed between a pair of electrodes, wherein at least one layer is a layer containing at least one compound represented by the following formula (IA):

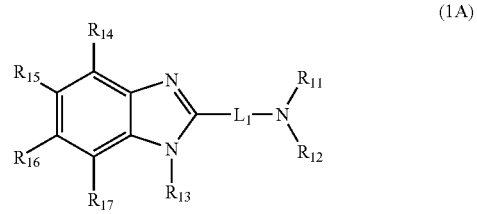

wherein $R_{11}$, $R_{12}$ and $R_{13}$ each represents a hydrogen atom, an aliphatic hydrocarbon group, an aryl group or a heterocyclic group; $L_1$ is selected from the group consisting of a single bond, alkylene, alkenylene, alkynylene, arylene and a divalent aromatic heterocyclic group selected from the group consisting of:

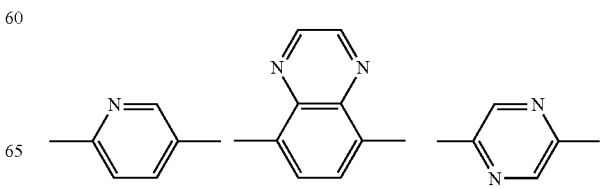

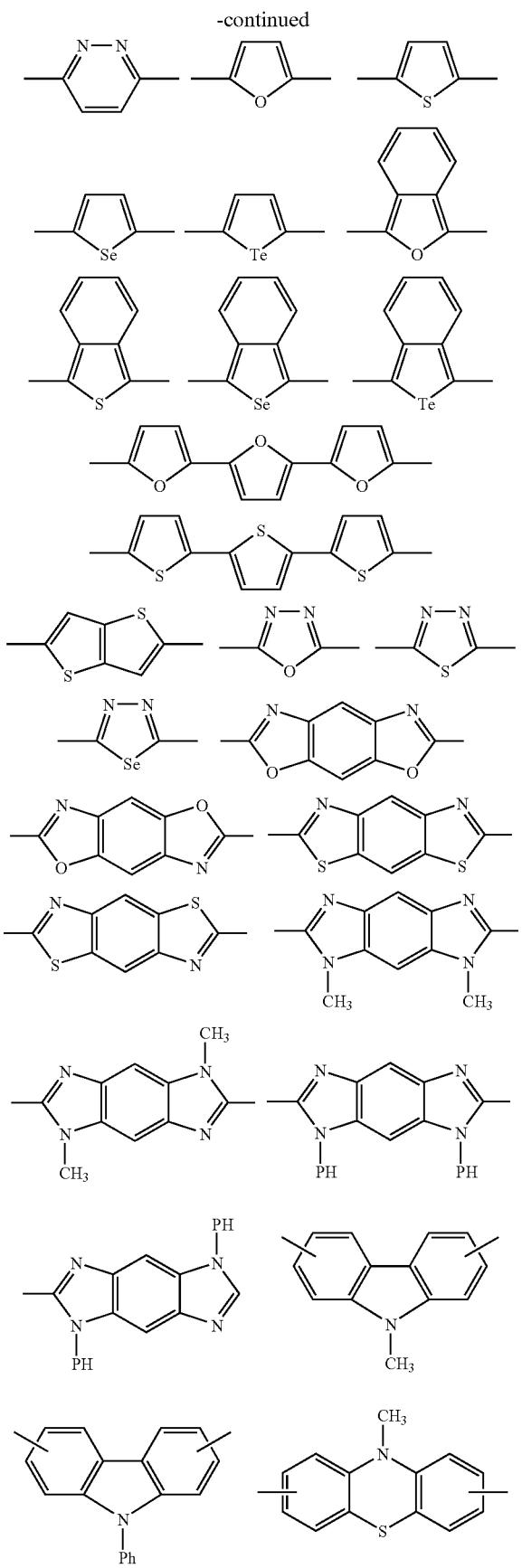
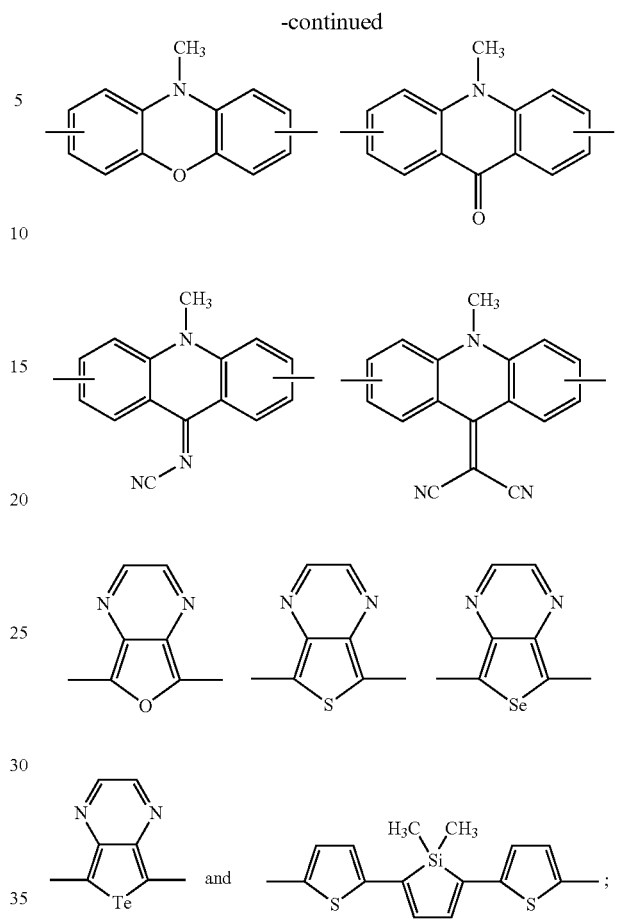

$R_{11}$ and $R_{12}$, $R_{11}$ and $L_1$ and $R_{12}$ and $L_1$ may each combine with each other to form a ring when possible; $R_{14}$, $R_{15}$, $R_{16}$ and $R_{17}$ each represents a hydrogen atom or a substituent; and $R_{13}$ to $R_{17}$ may each combine with each of $R_{11}$ to $R_{17}$ or $L_1$ to form a ring when possible.

2. The light emitting device of claim 1, further comprising a polymer in the at least one layer.

3. The light emitting device of claim 1, wherein $R_{11}$ and $R_{12}$ combine with each other to form a 5- to 7-membered ring with N.

4. The light emitting device of claim 3, wherein the 5- to 7-membered ring with N is selected from the group consisting of a pyrrole, azepine, piperidine, pyrrolidine, a piperazine, morpholine, thiomorpholine and hexamethyleneimine.

5. The light emitting device of claim 1, wherein $L_1$ is an arylene or divalent aromatic heterocyclic group.

6. The light emitting device of claim 1, wherein $R_{13}$ represents an alkyl, aryl or aromatic heterocyclic group.

7. The light emitting device of claim 1, wherein $R_{14}$, $R_{15}$, $R_{16}$ and $R_{17}$ each represents a hydrogen, alkyl, alkenyl, alkynyl, aryl, alkoxy, aryloxy, acyl, halogen, cyano, heterocyclic or silyl.

8. The light emitting device of claim 7, wherein $R_{14}$, $R_{15}$, $R_{16}$ and $R_{17}$ each represents a hydrogen, alkyl, aryl, or heterocyclic.

9. A compound represented by the following formula (IIA):

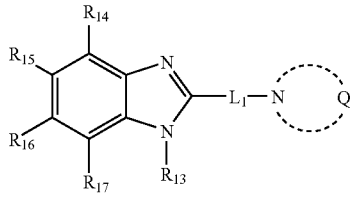

(IIA)

wherein $R_{13}$ represents an aliphatic hydrocarbon group, an aryl group or a heterocyclic group; $L_1$ represents a single bond, alkenylene, alkynylene, arylene or a divalent aromatic heterocyclic group Q represents an atomic group necessary for forming a 5-, 6- or 7-membered ring with N; $R_{14}$, $R_{15}$, $R_{16}$ and $R_{17}$ each represents a hydrogen atom or a substituent; and $R_{14}$, $R_{15}$, $R_{16}$ and $R_{17}$ may each combine with each of $R_{14}$ to $R_{17}$, $L_1$ or the atomic group Q to form a ring.

10. The compound of claim 9, wherein the 5- to 7-membered ring with N is selected from the group consisting of a pyrrole, azepine, piperidine, pyrrolidine, a piperazine, morpholine, thiomorpholine and hexamethyleneimine.

11. The compound of claim 10, wherein the 5- to 7-membered ring with N is a pyrrole or azepine.

12. The compound of claim 10, wherein $L_1$ is an arylene or divalent aromatic heterocyclic group.

13. The compound of claim 9, wherein $R_{13}$ represents an alkyl, aryl or aromatic heterocyclic group.

14. The compound of claim 13, wherein $R_{13}$ represents an aryl or aromatic heterocyclic group.

15. The compound of claim 9, wherein $R_{14}$, $R_{15}$, $R_{16}$ and $R_{17}$ each represents a hydrogen, alkyl, alkenyl, alkynyl, aryl, alkoxy, aryloxy, acyl, halogen, cyano, heterocyclic or silyl.

16. The compound of claim 15, wherein $R_{14}$, $R_{15}$, $R_{16}$ and $R_{17}$ each represents a hydrogen, alkyl, aryl, or heterocyclic.

17. The compound of claim 16, wherein $R_{14}$, $R_{15}$, $R_{16}$ and $R_{17}$ each represents a hydrogen.

18. The compound of claim 9, wherein $L_1$ is a divalent aromatic heterocyclic group selected from the group consisting of:

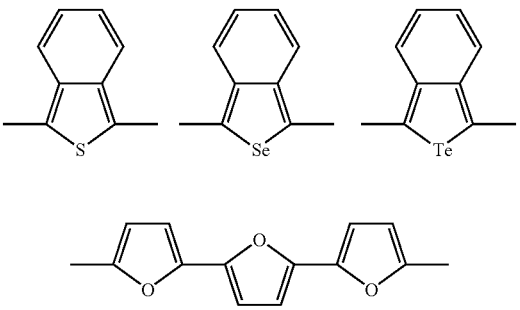

-continued